US010076566B2

(12) United States Patent
Audonnet et al.

(10) Patent No.: US 10,076,566 B2
(45) Date of Patent: *Sep. 18, 2018

(54) RECOMBINANT CDV COMPOSITIONS AND USES THEREOF

(71) Applicant: MERIAL, INC., Duluth, GA (US)

(72) Inventors: Jean-Christophe Audonnet, Lyons (FR); Jules Minke, Corbas (FR)

(73) Assignee: Merial Inc., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/084,108

(22) Filed: Mar. 29, 2016

(65) Prior Publication Data

US 2016/0199483 A1 Jul. 14, 2016

Related U.S. Application Data

(63) Continuation of application No. 13/035,904, filed on Feb. 25, 2011, now Pat. No. 9,327,137.

(60) Provisional application No. 61/308,620, filed on Feb. 26, 2010.

(51) Int. Cl.

| | |
|---|---|
| ***A61K 39/175*** | (2006.01) |
| ***C12N 7/00*** | (2006.01) |
| ***A61K 39/12*** | (2006.01) |
| ***C07K 14/005*** | (2006.01) |
| ***C07K 14/535*** | (2006.01) |
| ***A61N 5/06*** | (2006.01) |
| *A61K 39/00* | (2006.01) |

(52) U.S. Cl.

CPC ............ *A61K 39/175* (2013.01); *A61K 39/12* (2013.01); *A61N 5/0613* (2013.01); *C07K 14/005* (2013.01); *C07K 14/535* (2013.01); *C12N 7/00* (2013.01); *A61K 2039/53* (2013.01); *A61K 2039/545* (2013.01); *A61K 2039/552* (2013.01); *A61K 2039/55522* (2013.01); *C12N 2710/24043* (2013.01); *C12N 2750/14334* (2013.01); *C12N 2760/18422* (2013.01); *C12N 2760/18434* (2013.01); *C12N 2760/18471* (2013.01); *C12N 2800/22* (2013.01)

(58) Field of Classification Search

None

See application file for complete search history.

(56) References Cited

U.S. PATENT DOCUMENTS

| | | | |
|---|---|---|---|
| 5,606,024 | A | 2/1997 | Boone |
| 5,702,919 | A | 12/1997 | Nash |
| 5,756,102 | A | 5/1998 | Paoletti |
| 6,228,846 | B1 | 5/2001 | Audonnet |
| 6,309,647 | B1 | 10/2001 | Paoletti |
| 7,250,161 | B2 | 7/2007 | Bublot |
| 7,294,338 | B2 | 11/2007 | Audonnet |
| 2005/0255127 | A1 | 11/2005 | Loosmore |
| 2006/0240034 | A1 | 10/2006 | Junghans |
| 2008/0008683 | A1 | 1/2008 | Renard |

FOREIGN PATENT DOCUMENTS

| | | |
|---|---|---|
| FR | 2 775 601 | 9/1999 |

OTHER PUBLICATIONS

U.S. Appl. No. 15/065,581 Recombinant CDV compositions and uses thereof, filed Mar. 9, 2016.*

Sin et al., Enhancement of protective humoral (Th2) and cellmediated (Th1) immune responses against herpes simplex virus-2 through co-delivery of granulocytemacrophage colony-stimulating factor expression cassettes, 1998, European Journal of Immunology, vol. 28, pp. 3530-3540.*

Parker et al., Genetically engineered herpes simplex viruses that express IL-12 or GM-CSF as vaccine candidates, 2006, Vaccine, vol. 24, pp. 1644-1652.*

Fenner, et al., 1987, Veterinary Virology, Academic Press, Inc., pp. 485-503.

Graves et al., "Measles Virus Polypeptide Synthesis in Infected Cells", 1978, Virology 86:254-263.

Diallo A., "Morbillivirus group" genome organization and proteins, 1990, Vet. Micro. 23: 155-163.

Burgess et al., "Purification and Properties of Colony-stimulating Factor form Mouse Lung-conditioned Medium", 1977, J. Biol. Chem.252:1998-2003.

Cantrell et al., "Cloning, Sequence, and Expression of a Human Granulocyte/Macrophage Colony-Stimulating Factor", 1985, Proc. Natl. Acad. Sci. USA 82:6250-6254.

Fischer L. et al., "vaccination of puppies born to Immune dams with a canine adenovirus-based vaccine protects against a canine distemper virus challenge", Vaccine, vol. 20. No. 29-30, Oct. 4, 2002, p. 3485-3497).

Nielsen Line et al., "Changes in the receptor binding haemagglutinin protein of wild-type morbilliviruses are not required for adaptation to Vero cells", Virus Genes, vol. 27, No. 2 Oct. 2003 p. 157-162.

Nash RA et al., "Molecular cloning and in-vivo evaluation of canine granulocyte-macrophage colony-stimulating factor", Blood, vol. 78, 1991, p. 930-937.

Jones T, et al., "Potential role of granulocyte-macrophage colony-stimulating factor as vaccine adjuvant", European Journal of Clinical Microbiology & Infectiour Disease, vol. 13, No. suppl 02, Jan. 1, 1994, p. 47-53.

(Continued)

*Primary Examiner* — Benjamin P Blumel

(74) *Attorney, Agent, or Firm* — Judy Jarecki-Black; Steffan Finnegan; Merial Inc.

(57) ABSTRACT

The present invention provides vectors that contain and express in vivo or in vitro CDV polypeptides or antigens that elicit an immune response in animal against CDV, compositions comprising said vectors and/or CDV polypeptides, and methods of vaccination against CDV. The invention further provides methods for inducing an immunogenic or protective response against CDV and other canine virus, as well as methods for preventing or treating CDV and other canine virus or disease state(s) caused by CDV and other canine virus.

6 Claims, 40 Drawing Sheets

Specification includes a Sequence Listing.

(56) References Cited

OTHER PUBLICATIONS

GenBank accession #AAQ05830, haemagglutinin [Canine distemper virus], May 4, 2004.

GenBank accession #NP_001003245, colony stimulating factor 2 [canis lupus familiaris], Jun. 26, 2007.

Puigbo et al, Nucleic Acid Research 2007 (about online software for codon-optimization).

GenBank accession #AF478545, 2004.

GenBank accession #NM_001003245.

Saldarriaga et al. "Immunogenicity of a multicomponent DNA vaccine against visceral leishmaniasis in dogs", 2006, *Vaccine* 24, 1928-1940.

* cited by examiner

Figure 1A

| SEQ ID NO | Type | Gene Description |
|---|---|---|
| 1 | DNA | Codon-optimized CDV HA gene |
| 2 | Protein | CDV HA protein (encoded by codon-optimized DNA) |
| 3 | DNA | Codon-optimized canine GM-CSF |
| 4 | Protein | Codon-optimized canine GM-CSF |
| 5 | Protein | CDV HA protein in vCP258 |
| 6 | DNA | Part of pCXL1557.1 containing arms and insert (forward strand) |
| 7 | DNA | The entire pCXL1557.1 DNA sequence |
| 8 | DNA | Part of pJSY2218.1 containing arms and insert (forward strand) |
| 9 | DNA | The entire pJSY2218.1 DNA sequence |
| 10 | oligo | 13220CXL primer for synthetic CDV HA probe |
| 11 | oligo | 13225CXL primer for synthetic CDV HA probe |
| 12 | oligo | 7931DC primer for PCR amplification |
| 13 | oligo | 7932DC primer for PCR amplification |
| 14 | DNA | Part of vCP2263 containing arms and insert (forward strand) |
| 15 | oligo | 18071BK primer for amplifying canine GM-CSF probe |
| 16 | oligo | 18073BK primer for amplifying canine GM-CSF probe |
| 17 | oligo | 8103JY primer for PCR amplification of C3L-Canine GM-CSF-C3R |
| 18 | oligo | 8104JY primer for PCR amplification of C3L-Canine GM-CSF-C3R |
| 19 | DNA | Part of vCP2391 containing C3L-H6 promoter-Canine GM-CSF-C3R |
| 20 | Protein | AAQ05828 |
| 21 | Protein | ABF55673 |
| 22 | Protein | CAA55672 |
| 23 | Protein | AAQ96308 |
| 24 | Protein | ABF55671 |
| 25 | Protein | ACS88240 |
| 26 | Protein | ABK35770 |
| 27 | Protein | ACD92997 |
| 28 | Protein | ACI28389 |
| 29 | Protein | ACI28390 |
| 30 | Protein | ACN58242 |
| 31 | Protein | ABB51156 |
| 32 | Protein | ABK35780 |
| 33 | Protein | ACJ46470 |
| 34 | Protein | ABX84040 |

Figure 1B

| | | |
|---|---|---|
| 35 | DNA | AF478545, wildtype DNA encoding CDV HA (AAQ05830) |
| 36 | DNA | AF478543 DNA encoding CDV HA AAQ05828 |
| 37 | DNA | DQ494318 DNA encoding CDV HA ABF55672 |
| 38 | DNA | AY386316 DNA encoding CDV HA AAQ96308 |
| 39 | DNA | DQ494317 DNA encoding CDV HA ABF55671 |
| 40 | DNA | GQ214376 DNA encoding CDV HAACS88240 |
| 41 | DNA | DQ889177 DNA encoding CDV HA ABK35770 |
| 42 | DNA | EU716337 DNA encoding CDV HA ACD92997 |
| 43 | DNA | FJ011004 DNA encoding CDV HA ACI28389 |
| 44 | DNA | FJ011005 DNA encoding CDV HA ACI28390 |
| 45 | DNA | FJ705233 DNA encoding CDV HA ACN58242 |
| 46 | DNA | DQ228166 DNA encoding CDV HA ABB51156 |
| 47 | DNA | DQ889187 DNA encoding CDV HA ABK35780 |
| 48 | DNA | FJ423608 DNA encoding CDV HA ACJ46470 |
| 49 | DNA | EU325730 DNA encoding CDV HA ABX84040 |
| 50 | DNA | Part of vCP2392 containing C3L-H6 promoter-Canine GM-CSF-C3R |
| 51 | DNA | Part of vCP2392 containing H6 promoter-Canine GM-CSF |

Figure 2

Comparison of synthetic CDV HA and CDV HA in vCP258

```
                          1                                                50
synthetic CDV HA    (1)   MLSYQDKVGAFYKDNARANSSKLSLVTEEQGGRRPPYLLFVLLILLVGIM
   vCP258 CDV HA    (1)   MLPYQDKVGAFYKDNARANSTKLSLVTEGHGGRRPPYLLFVLLILLVGIL

                          51                                              100
synthetic CDV HA   (51)   TLLAITGVRFHQVSTSNMEFSRLLKEDMEKSEAVHHQVIDVLTPLFKIIG
   vCP258 CDV HA   (51)   ALLAITGVRFHQVSTSNMEFSRLLKEDMEKSEAVHHQVIDVLTPLFKIIG

                          101                                             150
synthetic CDV HA  (101)   DEVGLRLPQKLNEIKQFILQKTNFFNPNREFDFRDLHWCINPPSKIKVNF
   vCP258 CDV HA  (101)   DEIGLRLPQKLNEIKQFILQKTNFFNPNREFDFRDLHWCINPPSTVKVNF

                          151                                             200
synthetic CDV HA  (151)   TNYCDTIGIRKSIASAVNPILLSALSGGRGDIFPPYRCSGATTSVGRVFP
   vCP258 CDV HA  (151)   TNYCESIGIRKAIASAANPILLSALSGGRGDIFPPHRCSGATTSVGKVFP

                          201                                             250
synthetic CDV HA  (201)   LSVSLSMSLISKTSEITNMLTAISDGVYGKTYLLVPDYIEGEFDTQKIRV
   vCP258 CDV HA  (201)   LSVSLSMSLISRTSEVINMLTAISDGVYGKTYLLVPDDIEREFDTREIRV

                          251                                             300
synthetic CDV HA  (251)   FEIGFIKRWLNNMPLLQTTNYMVLPENSKAKVCTIAVGELTLASLCVDES
   vCP258 CDV HA  (251)   FEIGFIKRWLNDMPLLQTTNYMVLPKNSKAKVCTIAVGELTLASLCVEES

                          301                                             350
synthetic CDV HA  (301)   TVLLYHDSNGSQDGILVVTLGIFGATPMDQVEEVIPVAHPSVEKIHITNH
   vCP258 CDV HA  (301)   TVLLYHDSSGSQDGILVVTLGIFWATPMDHIEEVIPVAHPSMKKIHITNH

                          351                                             400
synthetic CDV HA  (351)   RGFIKDSIATWMVPALVSEKQEEQKNCLESACQRKTYPMCNQTSWEPFGG
   vCP258 CDV HA  (351)   RGFIKDSIATWMVPALASEKQEEQKGCLESACQRKTYPMCNQASWEPFGG

                          401                                             450
synthetic CDV HA  (401)   GQLPSYGRLTLSLDPSIDLQLNISFTYGPVILNGDGMDYYGSSLSDSGWL
   vCP258 CDV HA  (401)   RQLPSYGRLTLPLDASVDLQLNISFTYGPVILNGDGMDYYESPLLNSGWL

                          451                                             500
synthetic CDV HA  (451)   TIPPKNGTVLGLINKASRGDQFTVIPHVLTFAPRESSGNCYLPIQTSQIM
   vCP258 CDV HA  (451)   TIPPKDGTISGLINKAGRGDQFTVLPHVLTFAPRESSGNCYLPIQTSQIR

                          501                                             550
synthetic CDV HA  (501)   DKDVLTESNLVVLPTQNFRYVIATYDISRGDHAIVYYVYDPIRTISYTYP
   vCP258 CDV HA  (501)   DRDVLIESNIVVLPTQSIRYVIATYDISRSDHAIVYYVYDPIRTISYTHP

                          551                                             600
synthetic CDV HA  (551)   FRLTTKGRPDFLRIECFVWDDDLWCHQFYRFEADITNSTTSVENLVRIRF
   vCP258 CDV HA  (551)   FRLTTKGRPDFLRIECFVWDDNLWCHQFYRFEADIANSTTSVENLVRIRF

                          601
synthetic CDV HA  (601)   SCDRSKP-
   vCP258 CDV HA  (601)   SCNR----
```

synthetic CDV HA: SEQ ID NO:2; vCP258 CDV HA : SEQ ID NO:5
Sequence identity between SEQ ID NO:2 and SEQ ID NO:5 is 90.0% (Vector NTI program)

Figure 3
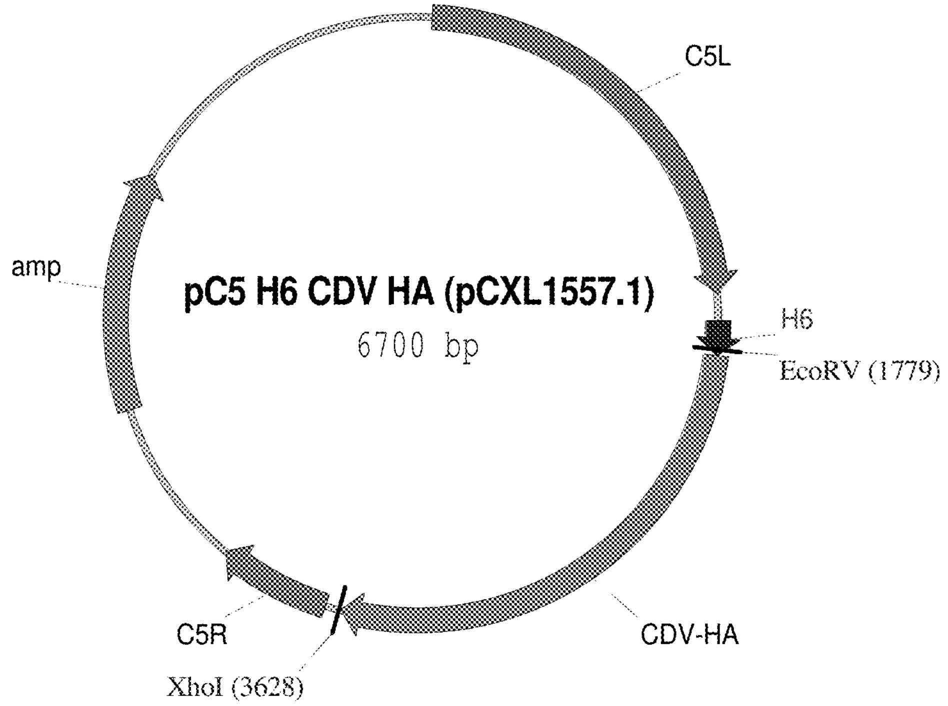
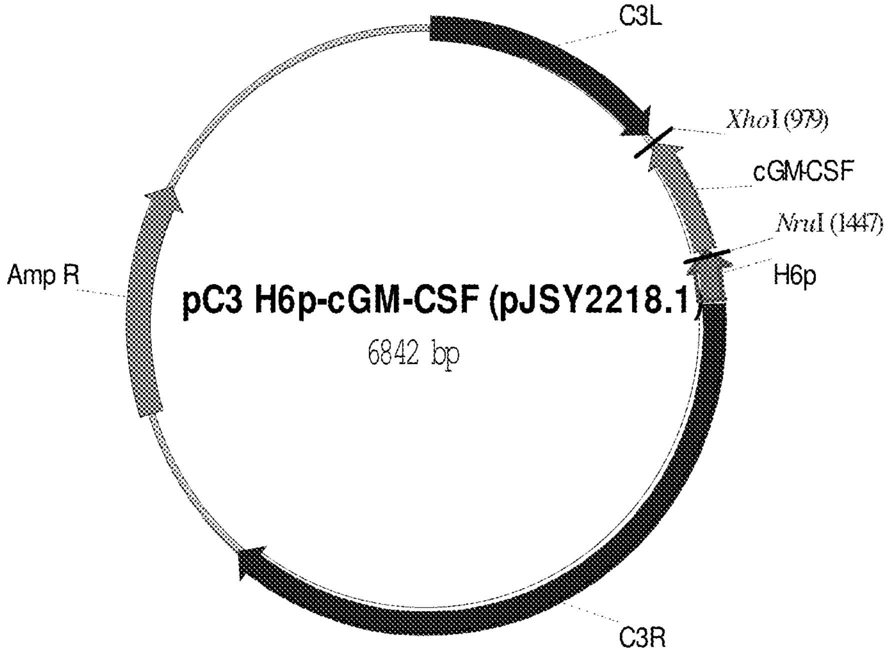

vCP2263 Southern blot analysis

Bands hybridized with CDV HA probe
VCP2263
Bam HI: 1984 bp
Hind III: 12294 bp
Pst I: 6468 and 13019 bp vCP2263 Western blot analysis 1. Fermentas Prestain protein marker
2. ALVAC cell pellet
3. vCP2263.1211 cell pellet
4. vCP2263.6111 cell pellet
5. space
6. ALVAC supernatant
7. vCP2263.1211 supernatant
8. vCP2263.6111 supernatant vCP2263 Immunoplaque assay Rabbit anti-CDV HA antibody ( Rabbit A151 and A152 at wk 23) at 1/100 dilution VCP2263.1.2.1.1 P3 stock, replica membranes, unstained, vCP2391 Western blot Lane:
1. PageRuler Protein Ladder
2. ALVAC supernatant
3. vCP2391 supernatant
4. space
5. sapce
6. space
7. space
8. ALVAC cell lysate
9. vCP2391 cell lysate vCP2392 Western blot for GM-CSF Lane:
1. Marker
2. ALVAC supernatant
3. vCP2392 supernatant
4. space
5. space
6. Marker
7. ALVAC cell lysate
8. vCP2392 cell lysate
9. space Western blot of vCP2391 and vCP2392 for GM-CSF vCP2391:
Lane 1: pellet
Lane 2: supernatant
Lane 3: crude vCP2392:
Lane 4: pellet
Lane 5: supernatant
Lane 6: crude vCP65 – negative control:
Lane 7: pellet
Lane 8: supernatant
Lane 9: crude Western blot of vCP2392 for CDV HA Lane 1: vCP2392 CEF cell lysate
Lane 2: vCP2263 CEF cell lysate
Lane 3: vCP2287 CEF Cell lysate
Lane 4: vCP2392 culture medium
Lane 5: vCP2263 culture medium
Lane 6: vCP2287 culture medium Primary antibody: goat anti-CDV antibody 1:1000 vCP2263: ALVAC C5 H6p-CDV HA
vCP2287: ALVAC C5 CDV HA/C3 H6p-CPV VP2 as positive control for western blot Serology Results

Figure 13A

```
                    1                                                     50
AAQ05828   (1)  MLSYQDKVGAFYKDNARANSSKLSLVTEEQGGRRPPYLLFVLLILLVGIM
AAQ96308   (1)  MLSYQDKVGAFYKDNARANSSKLSLVTEEQGGRRPPYLLFVLLILLVGIM
ABB51156   (1)  MLSYQDKVGAFYKDNARANSSKLSLVTEEQGGRRPPFLLFVLLVLLVGIM
ABF55671   (1)  MLSYQDKVGAFYKDNARANSSKLSLVTEEQGGRRPPYLLFVLLILLVGVM
ABF55672   (1)  MLSYQDKVGAFYKDNARANSSKLSLVTEEQGGRRPPYLLFVLLILLVGIM
ABF55673   (1)  MLSYQDKVGAFYKDNARANSSKLSLVTEEQGGRRPPYLLFVLLILLVGIM
ABK35770   (1)  MLSYQDKVGAFYKDNARANSSKLSLVTEEQGGRRPPYLLFVLLILLVGIM
ABK35780   (1)  MLSYQDKVSAFYKDNARANSSKLSLVTEEHGSRRPPYLLFILLILLVGIM
ABX84040   (1)  MLSYQDKVGAFYKDNARANSSKLSLVTEEQGGRRPPYLLFVLLILLIGIL
ACD92997   (1)  MLSYQDKVGAFYKDNARANSSKLSSVTEEQGGRRPPYLLFVLLILLVGIM
ACI28389   (1)  MLSYQDKVGAFYKDNARANSSKLSLVTEEQGGRRPPYLLFVLLILLVGIM
ACI28390   (1)  MLSYQDKVGAFYKDNARANSSKLSLVTEEQGGRRPPYLLFVLLILLVGIM
ACJ46470   (1)  MLSYQDKVGAFYKDNARANSSKLSLVTEEQGGRRPPYLFFVLLTLLIGIL
ACN58242   (1)  MLSYQDKVGAFYKDNARANSSKLSLVTEEQGGRRPPYLLFVLLILLTGIL
ACS88240   (1)  MLSYQDKVGAFYKDNARANSSKLSLVTEEQGGRRPPYLLFVLLILLVGIM
CDV HA     (1)  MLSYQDKVGAFYKDNARANSSKLSLVTEEQGGRRPPYLLFVLLILLVGIM

                    51                                                    100
AAQ05828   (51) TLLAITGVRFHQVSTSNMEFSRLLKEDMEKSEAVHHQVIDVLTPLFKIIG
AAQ96308   (51) TLLAITGVRFHQVSTSNMEFSRLLKEDMEKSEAVHHQVIDVLTPLFKIIG
ABB51156   (51) ALLAITGVRFHQVSTSNMEFSRLLKEDMEKSEAVHHQVIDVLTPLFKIIG
ABF55671   (51) TLXAITGVRIHQVSTSNMEFSRLLKEDMEKSEAVHHQVIDVLTPLFKIIG
ABF55672   (51) TLLAITGVRFHQVSTSNMEFSRLLKEDMEKSEAVHHQVIDVLTPLFKIIG
ABF55673   (51) TLLAITGVRFHQVSTSNMEFSRLLKEDMEKSEAVHHQVIDVLTPLFKIIG
ABK35770   (51) TLLAITGVRFHQVSTSNMEFSRLLKEDMEKSEAVHHQVIDVLTPLFKIIG
ABK35780   (51) ALLAITGARFHQVSTSNMEFSRLLKEDMEKSEAVHHQVIDVLTPLFKIIG
ABX84040   (51) ALLAITGVRFHQVSTSNMEFSRLLKEDMEKSEAVHHQVIDVLTPLFKIIG
ACD92997   (51) ALLAITGVRFHQVSTNNMEFSRLLKEDMEKSEAVHHQVIDVLTPLFKIIG
ACI28389   (51) TLLAITGVRFHQVSTSNMEFSRLLKEDMEKSEAVHHQVIDVLTPLFKIIG
ACI28390   (51) TLLAITGVRFHQVSTSNMEFSRLLKEDMEKSEAVHHQVMDVLTPLFKIIG
ACJ46470   (51) ALLAITGVRFHQVSTSNMEFSRLLKEDMEKSEAVHHQVIDVLTPLFKIIG
ACN58242   (51) ALLAITRVRFHQVSTSNMEFSRLLKEDMEKSEAVHHQVIDVLTPLFKIIG
ACS88240   (51) TLLAITGVRFHQVSTSNMEFSRLLKEDMEKSEAVHHQVIDVLTPLFKIIG
CDV HA     (51) TLLAITGVRFHQVSTSNMEFSRLLKEDMEKSEAVHHQVIDVLTPLFKIIG

                    101                                                   150
AAQ05828  (101) DEVGLRLPQKLNEIKQFILQKTNFFNPNREFDFRDLHWCINPPSKIKVNF
AAQ96308  (101) DEVGLQLPQKLNEIKQFILQKTNFFNPNREFDFRDLHWCINPPSKIKVNF
ABB51156  (101) DEIGLRLPQKLNEIKQFILQKTNFFNPNREFDFRDLHWCINPPSKIKVNF
ABF55671  (101) DEVGLRLPQKLNEIKQFILQKTNFFNPNREFDFRDLHWCINPPSKIKVNF
ABF55672  (101) DEVGLRLPQKLNEIKQFILQKTNFFNPNREFDFRDLHWCINPPSKIKVNF
ABF55673  (101) DEVGLRLPQKLNEIKQFILQKTNFFNPNREFDFRDLHWCINPPSKIKVNF
ABK35770  (101) DEVGLRLPQKLNEIKQFILQKTNFFNPNREFDFRDLHWCINPPSKIKVNF
ABK35780  (101) DEIGLRLPQKLNEIKQFILQKTNFFNPKREFDFRDLHWCINPPSKIKVNF
ABX84040  (101) DEIGLRLPQKLNEIKQFILQKTNFFNPNREFDFRDLHWCINPPSKIKVNF
ACD92997  (101) DEVGLRLPQKLNEIKQFILQKTNFFNPNREFDFRDLHWCINPPSKIKVNF
ACI28389  (101) DEVGLRLPQKLNEIKQFILQKTNFFNPNREFDFRDLHWCINPPSKIKVNF
```

Figure 13B

```
ACI28390(101) DEVGLRLPQKLNEIKQFILQKTNFFNPNREFDFRDLHWCINPPSKIKVNF
ACJ46470(101) DEIGLRLPQKLNEIKQFILQKTNFFNPNREFDFRDLHWCINPPSKIKVNF
ACN58242(101) DEIGLRLPQKLNEIKQFILQKTNFFNPNREFDFRDLHWCINPPSKIKVNF
ACS88240(101) DEVGLRLPQKLNEIKQFILQKTNFFNPNREFDFRDLHWCINPPSKIKVNF
  CDV HA(101) DEVGLRLPQKLNEIKQFILQKTNFFNPNREFDFRDLHWCINPPSKIKVNF

              151                                             200
AAQ05828(151) TNYCDTIGIRKSIASAVNPILLSALSGGRGDIFPPYRCSGATTSVGRVFP
AAQ96308(151) TNYCDTIGIKKSIASAANPILLSALSGGRGDIFPPYRCSGATTSVGRVFP
ABB51156(151) TNYCDTIGIRKSIASAANPILLSALSGGRGDIFPPYKCNGAATSVGRVFP
ABF55671(151) TNYCDTVGIRKSIASAANPILLSALSGGRGDIFPPYRCSGATTSVGRVFP
ABF55672(151) TNYCDTIGIRKSIASAANPILLSALSGGRGDIFPPYRCSGATTSVGRVFP
ABF55673(151) TNYCDTIGIRKSIASAANPILLSALSGGRGDIFPPYRCSGATTSVGRVFP
ABK35770(151) TNYCDTIGIRKSIASAANPILLSALSGGRGDIFPPYRCSGATTSVGRVFP
ABK35780(151) TNYCDTIGIRKSIALAANPILLSALSRGRGDIFPPYRCSGAATSVGRVFP
ABX84040(151) TNYCDTVGVKKSIASAANPIILSALSGARGDIFPPYRCSGATTSVGRVFP
ACD92997(151) TNYCDTIEIRKSIALAANPILLSALSGGRGDIFPPYSCSGATTSVGRVFP
ACI28389(151) TNYCDTIEIRKSIASAANPILLSALSGGRGDIFPPYRCSGATTSVGRVFP
ACI28390(151) SNYCDTIGIRKSIASAANPILLSALSGGRGDIFPPYRCNGAATSIGRVFP
ACJ46470(151) TNYCDTVGVKKSITSAANPIILSALSGARGDIFPPYRCSGATTSVGRVFP
ACN58242(151) TNYCDTVGVKKSIASAANPIILSALSGARGDIFPPCRCSGATTSVGRVFP
ACS88240(151) TNYCDTIGIRQSIASAANPILLSALSGGRGDIFPPYRCSGATTSVGRVFP
  CDV HA(151) TNYCDTIGIRKSIASAVNPILLSALSGGRGDIFPPYRCSGATTSVGRVFP

              201                                             250
AAQ05828(201) LSVSLSMSLISKTSEITNMLTAISDGVYGKTYLLVPDYIEGEFDTQKIRV
AAQ96308(201) LSVSLSMSLISKTSEITSMLTAISDGVYGKTYLLVPDYIEGEFDTQKIRV
ABB51156(201) LSVSLSMSLISKTSGIINMLTAISDGVYGKTYLLMPDYIEGEFDTQKIRV
ABF55671(201) LSVSLSMSLISKTSEITNMLTAISDGVYGKTYLLVPDYIEGEFDTQKIRV
ABF55672(201) LSVSLSMSLISKTSEITNMLTAISDGVYGKTYLLVPDYIEGEFDTQMIRV
ABF55673(201) LSVSLSMSLISKTSEITNMLTAISDGVYGKTYLLVPDYIEGEFDTQKIRV
ABK35770(201) LSVSLSMSLISKTSGITNMLTAISDGVYGKTYLLVPDYIEGEFDTQKIRV
ABK35780(201) LSVSLSMSLISRTSEIINMLTAISDGVYGKTYLLVPDYIEGEFDTQKIRV
ABX84040(201) LSVSLSMSLISRTSEIINMLTAISDGVYGKTYMLVPDYIEGEFDSQKIRV
ACD92997(201) LSVSLSMSLISKTSEIINMLTAISDGVYGKTYLLVPDYIEGGFDTQKIRV
ACI28389(201) LSVSLSMSLISRTSEITNMLTAISDGVYGKTYLLVPDYFEGEFDTQKIRV
ACI28390(201) LSVSLSMSLISRTAEIINMLTAISDGVDGKTYLLVPDYIEGEFETQKIRV
ACJ46470(201) LSVSLSMSLISRTSEIINMLTAISDGVYGKTYLLVPDYIEGEFDSQKIRV
ACN58242(201) LSVSLSMSLISRTSEIINMLTAISDGMYGKTYLLVPDYIEGEFDSQKIRV
ACS88240(201) LSVSLSMSVISKTSEITNMLTAISDGVYGKTYLLVPDYIEGEFDTQKIRV
  CDV HA(201) LSVSLSMSLISKTSEITNMLTAISDGVYGKTYLLVPDYIEGEFDTQKIRV

              251                                             300
AAQ05828(251) FEIGFIKRWLNNMPLLQTTNYMVLPENSKAKVCTIAVGELTLASLCVDES
AAQ96308(251) FEIGFIKRWLNNMPLLQTTNYMVLPENSKAKVCTIAVGELTLASLCVDES
ABB51156(251) FEIGFIKRWLNDMPLLQTTNYIVLPENSKAKVCTIAVGELTLASLCVDES
ABF55671(251) FEIGFIRRWLNNMPLLQTTNYMVLPENSKAKVCTIAVGELTLASLCVDES
ABF55672(251) FEIGFIKRWLNNMPLLQTTNYMVLPENSKAKVCTIAVGELTLASLCVDES
```

Figure 13C

```
ABF55673(251) FEIGFIKRWLNNMPLLQTTNYMVLPENSKAKVCTIAVGELTLASLCVDES
ABK35770(251) FEIGFIKRWLNNMPLFQTTNYMVLPENSKAKVCTIAVGELTLASLCVDES
ABK35780(251) FEIGFIKRWLNDMPLLQTTNYMVLPENSKAKVCTIAVGELTLASLCVDES
ABX84040(251) FEIGFIKRWLNNMPLLQTTNYMVLPETSKAKVCTIAVGELTLASLCVDES
ACD92997(251) FEIGFIKRWLNDMPLLQTTNYMVLPENSKAKVCTIAVGELTLASLCVDES
ACI28389(251) FEIGFIKRWLNDMPLLQTTNYMFLPENSKAKVCTIAVGELTLASLCVDES
ACI28390(251) FEIGFIKRWLNDMSLLQTTNYMVLPENSKAKVCTIAVGELTLASLCVDES
ACJ46470(251) FEIGFIKRWLNDMPLLQTTNYMVLPETSKAKVCTIAVGELTLASLCVDES
ACN58242(251) FEIGFIRRWLNDMPLLQTTNYMVLPETSKAKVCTIAVGELTLASLCVDES
ACS88240(251) FEIGFIKRWLNNMPLLQTTNYMVLPENSKAKVCTIAVGELTLASLCVDEN
  CDV HA(251) FEIGFIKRWLNNMPLLQTTNYMVLPENSKAKVCTIAVGELTLASLCVDES

              301                                             350
AAQ05828(301) TVLLYHDSNGSQDGILVVTLGIFGATPMDQVEEVIPVAHPSVEKIHITNH
AAQ96308(301) TVLLYHDSNGSQDGILVVTLGIFGATPMDQVEEVIPVAHPSVEKIHITNH
ABB51156(301) TVLLYHDSNGSQDGILVVTLGIFGATPMDQVEEVIPVAHPSVXKIHITNH
ABF55671(301) TVLLYHDSNGSQDGILVVTLGIFGATPMDQVEEVIPVAHPSVEKIHITNH
ABF55672(301) TVLLYHDSNGSQDGILVVTLGIFGATPMDQVGEVIPVAHPSVEKIHITNH
ABF55673(301) TVLLYHDSNGSQDGILVVTLGIFGATPMDQVGEVIPVAHPSVEKIHITNH
ABK35770(301) TVLLYHDSNGSQGGVLVVTLGIFGATPMDQVEEMIPVAHPSVEKIHITNH
ABK35780(301) TVLLYHDSNGSQDGILVVTLGIFGATPMDQVEEVIPVAHPSVEKIHITNH
ABX84040(301) TVLLYHDSNGSQNGILVVTLGIFGATPMDQVEEVIPIAHPSVERIHITNH
ACD92997(301) TVLLYHDSDGSQDGILVVTLGIFGATPMDQVEEVIPVAHPSVEKIHITNH
ACI28389(301) TVSLYHDGSGSQDGILVVTLGIFGATPMDQVEEVIPVAHPSVEKIHITNH
ACI28390(301) TVLLYHDSNGSQDGILVVTLGIFWGTPMDQVEEVIPVAHPSVEKIHITNH
ACJ46470(301) TVLLYHDSNGSQNGILVVTLGIFGATSMDQVEEVIPIAHPSVERIHITNH
ACN58242(301) TVLLYHDSNGSQNGILVVTLGIFGATPMDQVEEVIPIAHPSVERIHITNH
ACS88240(301) TVLLYHDSNGSQDGILVVTLGIFGATPMDQVEEVIPVAHPSIEKIHITNH
  CDV HA(301) TVLLYHDSNGSQDGILVVTLGIFGATPMDQVEEVIPVAHPSVEKIHITNH

              351                                             400
AAQ05828(351) RGFIKDSIATWMVPALVSEKQEEQKNCLESACQRKTYPMCNQTSWEPFGG
AAQ96308(351) RGFIKDSIATWMVPALVSEKQEEQKNCLESACQRKTYPMCNQTSWEPFGG
ABB51156(351) RGFIKDSIATWMVPALISGEQEEQKNCLESACQRKSYPMCNQTSWKPFGG
ABF55671(351) RGFIKDAIATWMVPALVSEKQEEQKNCLESACQRKTYPMCNQTSWEPFGG
ABF55672(351) RGFIKDSIATWMVPALVSEKQEEQKNCLESACQRKTYPMCNQTSWEPFGG
ABF55673(351) RGFIKDSIATWMVPALVSEKQEEQKNCLESACQRKTYPMCNQTSWEPFGG
ABK35770(351) RGFIKDSIATWMVPVLVSEKQEEQKNCLESACQRKTYPMCNQTSWEPFGG
ABK35780(351) RGFIKDSIATWMVPVLVSENQEEQKNCLESACQRKSYPMCNQTSWEPFGG
ABX84040(351) RGFIKDSVVTWMVPVLVSEKQEEQKNCLESACQRKSYPMCNQTSWEPFGG
ACD92997(351) RGFIKDSIATWMVPALVSEKQEEQKNCLESACQRKSYPMCNQTSWEPFGG
ACI28389(351) RGFIKDSIATWMVPALVSEKQEEQKNCLESACQRKTYPMCNQTSWEPFGG
ACI28390(351) RGFIKDSKAIWMVPALVSEKQEEQKNCLESACQRKTYPMCNQTSWEPFGG
ACJ46470(351) RGFIKDSIVTWMVPVLVSEKQEEQKNCLESACQRKSYPMCNQTSWEPFGG
ACN58242(351) RGFIKDSIVTWMVPVLVSEKQEEQKNCLESACQRKTYPMCNQTSWEPFGG
ACS88240(351) RGFIKDSIATWMVPALVSEKQEEQKNCLESACQRKTYPMCNQTSWEPFGG
  CDV HA(351) RGFIKDSIATWMVPALVSEKQEEQKNCLESACQRKTYPMCNQTSWEPFGG
```

Figure 13D

```
               401                                              450
AAQ05828(401)  GQLPSYGRLTLSLDPSIDLQLNISFTYGPVILNGDGMDYYGSSLSDSGWL
AAQ96308(401)  GQLPSYGRLTLPLDPSIDLQLNISFTYGPVILNGDGMDYYESPLSDSGWL
ABB51156(401)  GQLPSYGRLTLPLDPGIDLQLNISFTYGPVILNGDGMDYYESPLLDSGWL
ABF55671(401)  GQLPSYGRLTLPLDPSIDLQLNISFTYGPVILNGDGMDYYESSLSDSGWL
ABF55672(401)  GQLPSYGRLTLPLDPSIDPQLNISFTYGPVILNGDGMDYYESSLSDSGWL
ABF55673(401)  GQLPSYGRLTLPLDPSIDPQLNISFTYGPVILNGDGMDYYESSLSDSGWL
ABK35770(401)  GQLPSYGRLTLPLDPSIDLQLNISFTYGPVILNGDGMDYYESPLLDSGWL
ABK35780(401)  GQLPSYGRLTLPLDPGIDLQLNLSFTYGPIILNGDGMDYYESPLLNSGWL
ABX84040(401)  GQLPSYGRLTLPLDPSVDLQLNISFTYGPVILNGDGMDYYESPLLESGWL
ACD92997(401)  GQLPSYGRLTLPLDPSIDLQLNISFTYGPVILNGDGMDYYESPLLDSGWL
ACI28389(401)  GQLPSYGRWTLPLDPSIDLQLNISVTYGPVILNGDGMDYYESPLSDSGWL
ACI28390(401)  GQLPSYGRLTLPLDPSIDLQLNISFTYGPVILNGDGMDYYESPLLDSGWL
ACJ46470(401)  GQLPSYGRLTLPLDPSIDLQLNISFTYGPVILNGDGMDYYESPLLESGWL
ACN58242(401)  GQLPSYGRLTLPLDPSIDLQLNISFTYGPVILNGDGMDYYESPLLDSGWL
ACS88240(401)  RQLPSYGRLTLPLDPSMDLQLNISFTYGPVILNGDGMDYYESPLPDSGWL
  CDV HA(401)  GQLPSYGRLTLSLDPSIDLQLNISFTYGPVILNGDGMDYYGSSLSDSGWL

               451                                              500
AAQ05828(451)  TIPPKNGTVLGLINKASRGDQFTVIPHVLTFAPRESSGNCYLPIQTSQIM
AAQ96308(451)  TIPPRNGTVLGLINKASRGDQFTVIPHVLTFAPRESSGNCYLPIQTSQIM
ABB51156(451)  TIPPKNGTILGLINKASRGDQFTVIPHVLTFAPRESSGNCYLPIQTSQIM
ABF55671(451)  TIPPKNGTVLGLINKASRGDQFTVTPHVLTSAPRESSGNCYLPIQTSQIM
ABF55672(451)  TIPPKNGTVLGLINKASRGDQFTVIPHVLTFAPRESSGNCYLPIQTSQIM
ABF55673(451)  TIPPKNGTVLGLINKASRGDQFTVIPHVLTFAPRESSGNCYLPIQTSQIM
ABK35770(451)  TIPPKNGTVLGLINKASRGDQFTVIPHVLTFAPRESSGNCYLPIQTSQIM
ABK35780(451)  TIPPKNGTILGLINKASRGDQFTVTPHVLTFAPRESSGNCYLPIQTSQIM
ABX84040(451)  AIPPKNGTVLGLINKASRGDQFTVTPHVLTFAPRESSGNCYLPIQTSQIM
ACD92997(451)  TIPPKNGTVLGLINKASRGDQFTVIPHVLTFAPRESSGNCYLPIQTSQIM
ACI28389(451)  TIPPKNGTILGLINKASRGDQFTVIPHVLTFAPRESSGNCYLPIQTSQIM
ACI28390(451)  TIPPKNGTVLGLMNKASRGDQFTVIPHVLTFAPRESGGNCYLPIQTSQIM
ACJ46470(451)  TIPPKNGTVLGLINKASRGDQFTATPHVLTFAPRESSGNCYLPIQTSQIM
ACN58242(451)  TIPPKNGTVLGLINKASRGDQFTVTPHVLTFAPRESSGNCYLPIQTSQIM
ACS88240(451)  TIPPKNGTVLGLINKASRGDQFTVIPHVLTFAPRESSGNCYLPIQTSQIM
  CDV HA(451)  TIPPKNGTVLGLINKASRGDQFTVIPHVLTFAPRESSGNCYLPIQTSQIM

               501                                              550
AAQ05828(501)  DKDVLTESNLVVLPTQNFRYVIATYDISRGDHAIVYDVYDPIRTISYTHP
AAQ96308(501)  DKDVLTESNLVVLPTQNFRYVIATYDISRGDHAIVYYVYDPIRTISYTHP
ABB51156(501)  DKDVLTESNLVVLPTQNFRYVIATYDISRNDHAIVYYVYDPIRTISYTHP
ABF55671(501)  DKDVLTESNLVVLPTQNFRYVIATYDISRGDHAIVYYVYDPIRTISYTYP
ABF55672(501)  DKDVLTESNLVVLPTQNFRYVIATYDISRGDHAIVYYVYDPIRTISYTYP
ABF55673(501)  DKDVLTESNLVVLPTQNFRYVIATYDISRGDHAIVYYVYDPIRTISYTYP
ABK35770(501)  DKDVLTESNLVVLPTQNFRYVIATYDISRGDHAIVYYVYDPIRTISYTYP
ABK35780(501)  DKDVLTESNLVVLPTQNFRYVIATYDISRDDHAIVYYVYDPIRTISYTYP
ABX84040(501)  DKDVLTESNLVVLPTQNFRYVIATYDISRGDHAIVYYVYDPIRTISYTYP
ACD92997(501)  DKDVLTESNLVVLPTQNFRYVIATYDISRGDHAIVYYVYDPIRAISYTYP
ACI28389(501)  DKDVLTESNLVVLPTQNFRYVIATYDISRGDHAIVYYVYDPIRTISYTYP
```

Figure 13E

```
ACI28390(501) DKDVLAESNLVVLPTQNFRYVIATYDISRDDHAIVYYVYDPIRTISYTYP
ACJ46470(501) DKDVLTESNLVVLPTQNFRYVIATYDISRGDHAIVYYVYDPIRTISYTYP
ACN58242(501) DKDVLTESNLVVLPTQNFRYVIATYDISRGDHAIVYYVYDPIRTISYTYP
ACS88240(501) DKDVLTESNLVVLPTQNFRYVIATYDISRGDHAIVYYVYDPIRTISYTYP
  CDV HA(501) DKDVLTESNLVVLPTQNFRYVIATYDISRGDHAIVYYVYDPIRTISYTYP

              551                                              600
AAQ05828(551) FRLTTKGRPDFLRIECFVWDDDLWCHQFYRFEADITNSTTSVENLVRIRF
AAQ96308(551) FRLTTKGRPDFLRIECFVWDDDLWCHQFYRFEADITNSTTSVENLVRIRF
ABB51156(551) FRLTTKGRPDFLRIECFVWDDDLWCHQFYRFEADITNSATSVENLVRIRF
ABF55671(551) FRLTTKGRPDFLRIECFVWDDDMWCHQFYRFEADITNSTTSVENLVRIRF
ABF55672(551) FRLTTKGRPDFLRIECFVWDDDLWCHQFYRFEADITNSTTSVENLVRIRF
ABF55673(551) FRLTTKGRPDFLRIECFVWDDDLWCHQFYRFEADITNSTTSVENLVRIRF
ABK35770(551) FRLTTKGRPEFLRIECFVWDDDLWCHQFYRFEADITNSTISVENLVHIRF
ABK35780(551) FRLTTKGRPDFLRIECFVWDYDLWCHQFYRFEADITNSTTSVENLVRIRF
ABX84040(551) FRLTTKGRPDFLRIECFVWDDDLWCHQFYRFEANITNSTTSVENLVRIRF
ACD92997(551) FRLTTKGRPDFLRIECFVWDDDLWCHQFYRFEADSTNSTTSVENLVRIRF
ACI28389(551) FRLTTKGRPVSLRIECFVWDDDLWCHQFYQFEADITNSTTSVENLVRIRF
ACI28390(551) FRLTTKGRPDFLRIECFVWDDDLWCHQFYRFEADITNSTTSVENLVRIRF
ACJ46470(551) FRLTTKGRPDFLRIECFVWDDDLWCHQFYRFEANITNSTTSVENLVRIRF
ACN58242(551) FRLTTKGRPDFLRIECFVWDDDLWCHQFYRFEANITNSTTSVENLVRIRF
ACS88240(551) FRLTTKGRPDFLRIECFVWDDDLWCHQFYRFEADITNSTTSVENLVCIRF
  CDV HA(551) FRLTTKGRPDFLRIECFVWDDDLWCHQFYRFEADITNSTTSVENLVRIRF

              601
AAQ05828(601) SCDRSKP
AAQ96308(601) SCNRSKP
ABB51156(601) SCNRSKP
ABF55671(601) SCNRSKP
ABF55672(601) SCNRSKP
ABF55673(601) SCNRSKP
ABK35770(601) SCNRSKP
ABK35780(601) SCNRSKP
ABX84040(601) SCNRSKP
ACD92997(601) SCNRSKP
ACI28389(601) SCNRSKP
ACI28390(601) SCNRSKP
ACJ46470(601) SCNRSKP
ACN58242(601) SCNRSKP
ACS88240(601) SCNRSKP
  CDV HA(601) SCDRSKP
```

AAQ05828:SEQ ID NO:20; AAQ96308:SEQ ID NO:23; ABB51156:SEQ ID NO:31;
ABF55671:SEQ ID NO:24; ABF55672:SEQ ID NO:22; ABF55673:SEQ ID NO:21;
ABK35770:SEQ ID NO:26; ABK35780:SEQ ID NO:32; ABX84040:SEQ ID NO:34;
ACD92997:SEQ ID NO:27; ACI28389:SEQ ID NO:28; ACI28390:SEQ ID NO:29;
ACJ46470:SEQ ID NO:33; ACN58242:SEQ ID NO:30; ACS88240:SEQ ID NO:25;
CDV HA:SEQ ID NO:2.

Figure 13F

Sequence identity percetage of CDV HA proteins

| SEQ ID NO: | 2 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|
| 2 | | 100 | 99 | 99 | 98 | 98 | 98 | 98 | 97 | 97 | 96 | 95 | 95 | 95 | 94 | 95 |
| 20 | | | 99 | 98 | 98 | 98 | 98 | 97 | 96 | 96 | 95 | 94 | 95 | 94 | 94 | 94 |
| 21 | | | | 98 | 98 | 98 | 98 | 97 | 97 | 97 | 96 | 95 | 96 | 95 | 95 | 95 |
| 22 | | | | | 98 | 98 | 98 | 98 | 97 | 97 | 96 | 95 | 95 | 95 | 94 | 95 |
| 23 | | | | | | 98 | 98 | 98 | 97 | 97 | 96 | 95 | 95 | 94 | 95 | 95 |
| 24 | | | | | | | 97 | 97 | 96 | 96 | 95 | 95 | 94 | 94 | 94 | 94 |
| 25 | | | | | | | | 97 | 96 | 96 | 95 | 94 | 95 | 94 | 94 | 94 |
| 26 | | | | | | | | | 96 | 96 | 95 | 95 | 95 | 95 | 94 | 95 |
| 27 | | | | | | | | | | 96 | 95 | 95 | 96 | 95 | 94 | 94 |
| 28 | | | | | | | | | | | 95 | 94 | 94 | 94 | 94 | 94 |
| 29 | | | | | | | | | | | | 94 | 94 | 94 | 93 | 93 |
| 30 | | | | | | | | | | | | | 93 | 94 | 94 | 98 |
| 31 | | | | | | | | | | | | | | 95 | 93 | 93 |
| 32 | | | | | | | | | | | | | | | 94 | 94 |
| 33 | | | | | | | | | | | | | | | | 98 |
| 34 | | | | | | | | | | | | | | | | |

Vector NTI (Invitrogen, Calsbad, CA, USA)

Figure 14A

```
                         1                                                50
SEQ ID NO:35      (1)    ATGCTCTCCTACCAAGACAAGGTGGGTGCCTTCTATAAGGATAATGCAAG
SEQ ID NO:1       (1)    ATGCTGAGCTACCAGGACAAAGTGGGCGCCTTCTACAAGGACAACGCCAG

                         51                                              100
SEQ ID NO:35     (51)    AGCTAATTCATCCAAGCTGTCCTTAGTGACAGAAGAGCAAGGGGGCAGGA
SEQ ID NO:1      (51)    GGCCAATAGCAGCAAGCTGAGCCTGGTGACCGAGGAGCAGGGCGGCAGGA

                         101                                             150
SEQ ID NO:35    (101)    GACCACCCTATTTGCTGTTTGTCCTTCTCATCCTTCTGGTTGGAATCATG
SEQ ID NO:1     (101)    GACCCCCCTACCTGCTGTTCGTGCTGCTGATCCTTCTTGTGGGCATCATG

                         151                                             200
SEQ ID NO:35    (151)    ACCTTGCTTGCTATCACTGGAGTTCGATTTCACCAAGTATCAACTAGCAA
SEQ ID NO:1     (151)    ACCCTGCTGGCCATCACCGGAGTGAGATTCCACCAGGTGTCCACCTCCAA

                         201                                             250
SEQ ID NO:35    (201)    TATGGAATTTAGCAGATTGCTGAAAGAGGATATGGAGAAATCAGAGGCCG
SEQ ID NO:1     (201)    CATGGAGTTCAGCCGGCTGCTGAAAGAGGACATGGAGAAGAGCGAGGCCG

                         251                                             300
SEQ ID NO:35    (251)    TACATCACCAAGTCATAGATGTCTTGACACCGCTCTTCAAAATTATTGGA
SEQ ID NO:1     (251)    TGCACCACCAGGTGATCGATGTGCTGACCCCCCTGTTCAAGATCATCGGC

                         301                                             350
SEQ ID NO:35    (301)    GATGAGGTTGGGTTACGGTTGCCACAAAAACTAAACGAGATCAAACAATT
SEQ ID NO:1     (301)    GACGAAGTGGGCCTGAGACTGCCCCAGAAGCTGAACGAGATCAAGCAGTT

                         351                                             400
SEQ ID NO:35    (351)    TATCCTTCAAAAGACAAACTTCTTCAATCCGAACAGGGAATTCGACTTCC
SEQ ID NO:1     (351)    CATCCTGCAGAAAACCAACTTCTTCAACCCCAACCGGGAGTTCGACTTCA

                         401                                             450
SEQ ID NO:35    (401)    GCGATCTCCACTGGTGCATTAATCCACCTAGTAAGATCAAGGTGAATTTT
SEQ ID NO:1     (401)    GAGACCTGCACTGGTGCATCAACCCCCCCAGCAAGATCAAAGTGAACTTC

                         451                                             500
SEQ ID NO:35    (451)    ACTAATTACTGCGATACAATTGGGATCAGAAAATCTATTGCATCGGCAGT
SEQ ID NO:1     (451)    ACCAACTACTGCGACACCATCGGCATCAGGAAGAGCATCGCCAGCGCCGT

                         501                                             550
SEQ ID NO:35    (501)    AAATCCCATCCTTTTATCAGCACTCTCCGGAGGCAGAGGTGACATATTCC
SEQ ID NO:1     (501)    GAATCCCATCCTGCTGAGCGCCCTGAGCGGCGGCAGAGGCGACATCTTCC

                         551                                             600
SEQ ID NO:35    (551)    CACCATACAGATGCAGTGGAGCTACTACTTCAGTGGGCAGAGTTTTCCCC
SEQ ID NO:1     (551)    CCCCCTACAGATGCAGCGGCGCCACCACCTCTGTGGGCAGAGTGTTCCCT

                         601                                             650
SEQ ID NO:35    (601)    CTATCAGTATCATTGTCCATGTCTTTGATCTCAAAAACATCAGAGATAAC
SEQ ID NO:1     (601)    CTGAGCGTGTCCCTGAGCATGAGCCTGATCAGCAAGACCAGCGAGATCAC
```

Figure 14B

```
                       651                                              700
SEQ ID NO:35    (651)  CAATATGCTAACTGCTATCTCAGACGGAGTGTATGGTAAAACCTATTTGC
SEQ ID NO:1     (651)  CAACATGCTGACCGCCATCAGCGACGGCGTGTACGGCAAGACCTATCTGC

                       701                                              750
SEQ ID NO:35    (701)  TAGTGCCTGATTACATTGAAGGGGAGTTCGACACGCAAAAGATTCGAGTC
SEQ ID NO:1     (701)  TGGTGCCCGACTACATCGAGGGCGAGTTCGACACCCAGAAGATCCGCGTG

                       751                                              800
SEQ ID NO:35    (751)  TTTGAGATAGGGTTCATCAAACGGTGGCTGAATAACATGCCATTACTCCA
SEQ ID NO:1     (751)  TTCGAGATCGGCTTCATCAAGCGGTGGCTGAACAACATGCCCCTGCTGCA

                       801                                              850
SEQ ID NO:35    (801)  GACAACCAACTACATGGTCCTCCCGGAGAATTCCAAAGCCAAGGTATGTA
SEQ ID NO:1     (801)  GACCACCAACTACATGGTGCTGCCCGAGAACAGCAAGGCCAAAGTGTGCA

                       851                                              900
SEQ ID NO:35    (851)  CTATAGCAGTGGGCGAGTTGACACTGGCTTCCTTGTGTGTAGATGAGAGC
SEQ ID NO:1     (851)  CCATCGCTGTGGGCGAGCTGACCCTGGCCAGCCTGTGCGTGGACGAGAGC

                       901                                              950
SEQ ID NO:35    (901)  ACCGTATTGTTATATCATGACAGCAATGGTTCACAAGATGGTATTCTAGT
SEQ ID NO:1     (901)  ACCGTGCTGCTGTACCACGACAGCAACGGCAGCCAGGACGGCATCCTGGT

                       951                                             1000
SEQ ID NO:35    (951)  AGTGACGCTGGGGATATTTGGGGCAACACCTATGGATCAAGTTGAAGAAG
SEQ ID NO:1     (951)  GGTGACCCTGGGCATCTTCGGCGCCACCCCTATGGACCAGGTGGAGGAAG

                       1001                                            1050
SEQ ID NO:35   (1001)  TGATACCTGTCGCTCACCCATCAGTAGAAAAAATACATATAACAAATCAC
SEQ ID NO:1    (1001)  TGATCCCCGTGGCCCACCCCAGCGTGGAGAAGATCCACATCACCAACCAC

                       1051                                            1100
SEQ ID NO:35   (1051)  CGTGGGTTCATAAAAGATTCAATAGCAACCTGGATGGTGCCTGCATTGGT
SEQ ID NO:1    (1051)  CGGGGCTTTATCAAGGACAGCATCGCCACCTGGATGGTGCCCGCCCTGGT

                       1101                                            1150
SEQ ID NO:35   (1101)  CTCTGAGAAACAAGAGGAACAAAAAAATTGTCTGGAGTCGGCTTGTCAAA
SEQ ID NO:1    (1101)  GTCTGAGAAGCAGGAGGAGCAGAAGAACTGCCTGGAGAGCGCCTGCCAGA

                       1151                                            1200
SEQ ID NO:35   (1151)  GAAAAACCTACCCTATGTGCAACCAAACGTCATGGGAACCCTTTGGAGGG
SEQ ID NO:1    (1151)  GAAAGACCTACCCCATGTGCAACCAGACCAGCTGGGAGCCCTTTGGCGGC

                       1201                                            1250
SEQ ID NO:35   (1201)  GGACAGTTGCCATCTTATGGGCGGTTGACATTATCTCTAGATCCAAGCAT
SEQ ID NO:1    (1201)  GGACAGCTGCCCAGCTACGGCAGACTGACCCTGAGCCTGGACCCTAGCAT

                       1251                                            1300
SEQ ID NO:35   (1251)  TGACCTTCAACTTAACATATCATTTACATACGGTCCAGTTATACTGAATG
SEQ ID NO:1    (1251)  CGACCTGCAGCTGAACATCAGCTTCACCTACGGCCCCGTGATCCTGAACG
```

Figure 14C

```
                        1301                                              1350
SEQ ID NO:35  (1301)  GAGACGGTATGGATTATTATGGAAGCTCACTTTCGGACTCCGGATGGCTT
SEQ ID NO:1   (1301)  GCGACGGCATGGATTACTACGGCAGCAGCCTGAGCGACAGCGGCTGGCTG

                        1351                                              1400
SEQ ID NO:35  (1351)  ACCATTCCTCCCAAGAATGGAACAGTCCTTGGATTGATAAACAAAGCAAG
SEQ ID NO:1   (1351)  ACCATCCCTCCCAAGAACGGCACAGTGCTGGGCCTGATCAACAAGGCCTC

                        1401                                              1450
SEQ ID NO:35  (1401)  TAGAGGAGACCAGTTCACTGTAATCCCCCATGTGTTGACATTTGCGCCCA
SEQ ID NO:1   (1401)  CAGGGGCGACCAGTTCACCGTGATCCCTCACGTGCTGACCTTCGCCCCCA

                        1451                                              1500
SEQ ID NO:35  (1451)  GGGAATCAAGTGGAAATTGTTATTTACCTATTCAAACATCCCAGATTATG
SEQ ID NO:1   (1451)  GAGAGAGCAGCGGCAACTGCTACCTGCCTATCCAGACCTCCCAGATCATG

                        1501                                              1550
SEQ ID NO:35  (1501)  GATAAAGATGTCCTGACTGAGTCCAATTTAGTGGTGTTGCCTACACAGAA
SEQ ID NO:1   (1501)  GACAAGGACGTGCTGACAGAGAGCAACCTGGTGGTGCTGCCTACCCAGAA

                        1551                                              1600
SEQ ID NO:35  (1551)  TTTTAGATATGTCATAGCAACATATGATATATCTCGGGGCGATCATGCAA
SEQ ID NO:1   (1551)  CTTCCGGTACGTGATCGCCACCTACGACATCAGCAGAGGCGATCACGCCA

                        1601                                              1650
SEQ ID NO:35  (1601)  TTGTTTATTATGTTTATGACCCAATCCGGACGATTTCTTATACGTACCCA
SEQ ID NO:1   (1601)  TCGTGTACTACGTGTACGACCCCATCCGGACCATCAGCTACACATACCCC

                        1651                                              1700
SEQ ID NO:35  (1651)  TTTAGACTAACTACCAAGGGTAGACCTGATTTCCTAAGAATTGAATGTTT
SEQ ID NO:1   (1651)  TTCCGGCTGACCACCAAGGGCAGACCCGACTTCCTGCGGATCGAGTGCTT

                        1701                                              1750
SEQ ID NO:35  (1701)  TGTGTGGGATGACGATTTGTGGTGTCACCAATTTTACCGATTTGAGGCTG
SEQ ID NO:1   (1701)  TGTGTGGGACGACGACCTGTGGTGCCACCAGTTCTACAGATTCGAGGCCG


                        1751                                              1800
SEQ ID NO:35  (1751)  ACATCACCAACTCTACAACCAGTGTTGAGAATTTAGTCCGTATAAGATTC
SEQ ID NO:1   (1751)  ACATCACCAATAGCACCACCTCCGTGGAGAACCTTGTGAGGATCCGGTTC

                        1801                    1824
SEQ ID NO:35  (1801)  TCATGTGACCGTTCAAAACCTTGA
SEQ ID NO:1   (1801)  AGCTGCGACAGAAGCAAGCCC---
```

Sequence identity between SEQ ID NO:1 and SEQ ID NO:35: 73%

Figure 15A

```
                   1                                                50
AF478543     (1)   ATGCTCTCCTACCAAGACAAGGTGGCTGCCTTCTATAAGGATAATGCAAG
AF478545     (1)   ATGCTCTCCTACCAAGACAAGGTGGCTGCCTTCTATAAGGATAATGCAAG
AY386316     (1)   ATGCTCTCCTACCAAGACAAGGTGGCTGCCTTCTATAAGGATAATGCAAG
ca CDV HA    (1)   ATGCTGAGCTACCAGGACAAAGTGGCCGCCTTCTACAAGGACAACGCCAG
DQ228166     (1)   ATGCTCTCCTACCAAGACAAGGTGGCTGCCTTCTATAAAGATAATGCAAG
DQ494317     (1)   ATGCTCTCCTACCAAGACAAGGTGGCTGCCTTCTATAAGGATAATGCAAG
DQ494318     (1)   ATGCTCTCCTACCAAGACAAGGTGGCTGCCTTCTATAAGGATAATGCAAG
DQ889177     (1)   ATGCTCTCCTACCAAGACAAGGTGGCTGCCTTCTATAAGGATAATGCAAG
DQ889187     (1)   ATGCTCTCCTACCAAGACAAGGTGACTGCCTTCTATAAGGATAATGCAAG
EU325730     (1)   ATGCTCTCTTACCAAGACAAGGTGGCTGCCTTCTATAAGGACAATGCAAG
EU716337     (1)   ATGCTCTCCTACCAAGACAAGGTGGCTGCCTTCTATAAGGATAATGCAAG
FJ011004     (1)   ATGCTCTCCTACCAAGACAAGGTGGCTGCCTTCTATAAGGATAATGCAAG
FJ011005     (1)   ATGCTCTCCTACCAAGACAAGGTGGCTGCCTTTTATAAGGATAATGCAAG
FJ423608     (1)   ATGCTCTCTTACCAAGACAAGGTGGCTGCCTTCTATAAGGATAATGCAAG
FJ705233     (1)   ATGCTCTCCTACCAAGACAAGGTGGCTGCCTTCTATAAGGATAATGCAAG
GQ214376     (1)   ATGCTCTCCTACCAAGACAAGGTGGCTGCCTTCTATAAGGATAATGCAAG

                   51                                              100
AF478543    (51)   AGCTAATTCATCCAAGCTGTCCTTAGTGACAGAAGAGCAAGGGGGCAGGA
AF478545    (51)   AGCTAATTCATCCAAGCTGTCCTTAGTGACAGAAGAGCAAGGGGGCAGGA
AY386316    (51)   AGCTAATTCATCCAAGCTGTCCTTAGTGACAGAAGAGCAAGGGGGCAGGA
ca CDV HA   (51)   GGCCAATAGCAGCAAGCTGAGCCTGGTGACCGAGGAGCAGGGCGGCAGGA
DQ228166    (51)   AGCCAATTCATCCAAGCTGTCCTTAGTGACAGAAGAGCAAGGGGGTAGAA
DQ494317    (51)   AGCTAATTCATCCAAGCTGTCCTTAGTGACAGAAGAGCAAGGGGGCAGGA
DQ494318    (51)   AGCTAATTCATCCAAGCTGTCCTTAGTGACAGAAGAGCAAGGGGGCAGGA
DQ889177    (51)   AGCTAATTCATCCAAGCTGTCCTTAGTGACAGAAGAGCAAGGGGGCAGGA
DQ889187    (51)   AGCCAATTCATCCAAACTGTCCTTAGTGACAGAAGAACATGGGAGCAGGA
EU325730    (51)   AGCTAATTCATCCAAGCTGTCCTTAGTGACAGAAGAGCAAGGGGGAAGGA
EU716337    (51)   AGCTAATTCATCCAAGCTGTCCTCAGTGACAGAAGAGCAAGGGGGCAGGA
FJ011004    (51)   AGCTAATTCATCCAAGCTGTCCTTAGTGACAGAAGAGCAAGGGGGCCGGA
FJ011005    (51)   AGCCAATTCATCCAAGCTGTCTCTAGTGACAGAAGAGCAAGGGGGTAGGA
FJ423608    (51)   AGCTAATTCATCCAAGCTGTCCTTAGTGACAGAAGAGCAAGGGGGAAGGA
FJ705233    (51)   AGCTAATTCATCCAAGCTGTCCTTAGTGACAGAAGAGCAAGGGGGAAGGA
GQ214376    (51)   AGCTAATTCATCCAAGCTGTCCTTAGTGACAGAAGAGCAAGGGGGCAGGA

                   101                                             150
AF478543   (101)   GACCACCCTATTTGCTGTTTGTCCTTCTCATCCTTCTGGTTGGAATCATG
AF478545   (101)   GACCACCCTATTTGCTGTTTGTCCTTCTCATCCTTCTGGTTGGAATCATG
AY386316   (101)   GACCACCCTATTTGCTGTTTGTCCTTCTCATCCTTCTGGTTGGAATCATG
ca CDV HA  (101)   GACCCCCCTACCTGCTGTTCGTGCTGCTGATCCTTCTTGTGGGCATCATG
DQ228166   (101)   GACCACCCTTTTTGCTGTTTGTCCTTCTCGTCCTACTGGTTGGAATCATG
DQ494317   (101)   GACCACCCTATTTGCTGTTTGTCCTTCTCATCCTTCTGGTTGGAGTCATG
DQ494318   (101)   GACCACCCTATTTGCTGTTTGTCCTTCTCATCCTTCTGGTCGGAATCATG
DQ889177   (101)   GACCACCCTATTTGCTGTTTGTCCTTCTCATCCTTCTGGTTGGAATCATG
DQ889187   (101)   GACCACCCTATTTGCTGTTTATCCTTCTCATCCTACTGGTTGGAATCATG
EU325730   (101)   GACCACCCTATTTGCTGTTTGTCCTTCTCATCCTACTGATTGGAATCCTG
EU716337   (101)   GACCACCCTATTTGCTGTTTGTCCTTCTCATCCTACTGGTTGGAATCATG
FJ011004   (101)   GACCACCCTATTTGCTGTTTGTCCTTCTCATCCTTCTGGTTGGAATCATG
FJ011005   (101)   GACCACCCTATCTGCTGTTTGTCCTTCTCATCCTACTGGTTGGAATCATG
FJ423608   (101)   GACCACCCTACTTGTTTTTTGTCCTTCTCACCCTACTGATTGGAATCCTG
FJ705233   (101)   GACCACCCTATTTGCTGTTTGTCCTTCTCATCCTACTGACTGGAATCCTG
GQ214376   (101)   GACCACCCTATTTGCTGTTTGTCCTTCTCATCCTTCTGGTTGGAATCATG
```

Figure 15B

```
                   151                                              200
AF478543    (151)  ACCTTGCTTGCTATCACTGGAGTTCGATTTCACCAAGTATCAACTAGCAA
AF478545    (151)  ACCTTGCTTGCTATCACTGGAGTTCGATTTCACCAAGTATCAACTAGCAA
AY386316    (151)  ACCTTGCTTGCTATCACTGGAGTTCGATTTCACCAAGTATCAACTAGCAA
ca CDV HA   (151)  ACCCTGCTGGCCATCACCGGAGTGAGATTCCACCAGGTGTCCACCTCCAA
DQ228166    (151)  GCCTTGCTTGCTATCACTGGAGTTCGATTTCATCAAGTATCAACCAGCAA
DQ494317    (151)  ACCTTGCNTGCTATCACTGGAGTTCGAATTCACCAAGTATCAACTAGCAA
DQ494318    (151)  ACCTTGCTTGCTATCACTGGAGTTCGATTTCACCAAGTATCAACTAGCAA
DQ889177    (151)  ACCTTGCTTGCTATCACTGGAGTTCGATTTCACCAAGTATCAACTAGCAA
DQ889187    (151)  GCCTTGCTTGCTATCACTGGAGCTCGATTTCACCAAGTATCAACTAGCAA
EU325730    (151)  GCCTTGCTTGCCATCACTGGAGTTCGATTTCACCAAGTATCAACTAGCAA
EU716337    (151)  GCCTTGCTTGCTATCACTGGAGTTCGATTTCACCAAGTATCAACTAACAA
FJ011004    (151)  ACCTTGCTTGCTATCACTGGAGTTCGATTTCACCAAGTATCAACTAGCAA
FJ011005    (151)  ACCTTGCTTGCTATCACCGGAGTTCGATTTCACCAGGTATCAACTAGCAA
FJ423608    (151)  GCCTTGCTTGCCATCACTGGAGTTCGATTTCACCAAGTATCAACTAGCAA
FJ705233    (151)  GCCTTGCTTGCCATCACTAGAGTTCGATTTCACCAAGTATCAACTAGCAA
GQ214376    (151)  ACCTTGCTTGCTATCACTGGAGTTCGATTTCACCAAGTATCAACTAGCAA

                   201                                              250
AF478543    (201)  TATGGAATTTAGCAGATTGCTGAAAGAGGATATGGAGAAATCAGAGGCCG
AF478545    (201)  TATGGAATTTAGCAGATTGCTGAAAGAGGATATGGAGAAATCAGAGGCCG
AY386316    (201)  TATGGAATTTAGCAGATTGCTGAAAGAGGATATGGAGAAATCAGAGGCCG
ca CDV HA   (201)  CATGGAGTTCAGCCGGCTGCTGAAAGAGGACATGGAGAAGAGCGAGGCCG
DQ228166     201)  TATGGAATTTAGTAGATTGCTGAAAGAGGATATGGAGAAATCTGAGGCCG
DQ494317    (201)  TATGGAATTTAGCAGATTGCTGAAAGAGGATATGGAGAAATCAGAGGCCG
DQ494318    (201)  TATGGAATTTAGCAGATTGTTGAAAGAGGATATGGAGAAATCAGAGGCCG
DQ889177    (201)  TATGGAATTTAGCAGATTACTGAAAGAGGATATGGAGAAATCAGAGGCCG
DQ889187    (201)  TATGGAATTTAGCAGATTGCTGAAAGAGGATATGGAGAAATCAGAGGCCG
EU325730    (201)  TATGGAATTTAGCAGATTGCTGAAAGAGGATATGGAGAAATCAGAGGCCG
EU716337    (201)  TATGGAATTTAGCAGATTGCTGAAAGAGGATATGGAGAAGTCAGAGGCCG
FJ011004    (201)  TATGGAATTTAGCAGATTGCTGAAAGAGGATATGGAGAAATCAGAGGCCG
FJ011005    (201)  TATGGAATTCAGCAGATTGCTGAAAGAGGATATGGAGAAATCAGAGGCCG
FJ423608    (201)  TATGGAATTTAGCAGATTGCTGAAAGAGGATATGGAGAAATCAGAGGCCG
FJ705233    (201)  TATGGAATTTAGCAGATTGCTGAAAGAGGATATGGAGAAATCAGAGGCCG
GQ214376    (201)  TATGGAATTTAGCAGATTGCTGAAAGAGGATATGGAGAAATCAGAGGCCG

                   251                                              300
AF478543    (251)  TACATCACCAAGTCATAGATGTCTTGACACCGCTCTTCAAAATTATTGGA
AF478545    (251)  TACATCACCAAGTCATAGATGTCTTGACACCGCTCTTCAAAATTATTGGA
AY386316    (251)  TACATCACCAAGTCATAGATGTCTTGACACCGCTCTTCAAAATTATTGGA
ca CDV HA   (251)  TGCACCACCAGGTGATCGATGTGCTGACCCCCCTGTTCAAGATCATCGGC
DQ228166    (251)  TACATCATCAAGTCATAGATGTTTTGACACCGCTCTTCAAAATCATCGGA
DQ494317    (251)  TACATCACCAAGTCATAGATGTCTTGACACCGCTCTTCAAAATTATTGGA
DQ494318    (251)  TACATCACCAAGTCATAGATGTCTTGACACCGCTCTTCAAAATTATTGGA
DQ889177    (251)  TACATCACCAAGTCATAGATGTCTTGACACCGCTCTTCAAAATTATTGGA
DQ889187    (251)  TACATCACCAAGTCATAGATGTCTTGACACCGCTCTTTAAAATTATTGGT
EU325730    (251)  TACATCACCAAGTCATAGATGTCTTGACACCGCTCTTCAAAATTATTGGA
EU716337    (251)  TACATCACCAAGTCATAGATGTCTTGACACCGCTCTTCAAGATTATTGGA
FJ011004    (251)  TACATCACCAAGTCATAGATGTCTTGACACCGCTCTTCAAAATTATTGGA
FJ011005    (251)  TACACCACCAAGTCATGGATGTCTTGACACCGCTCTTCAAAATTATTGGA
FJ423608    (251)  TACATCACCAAGTCATAGATGTCTTGACACCGCTCTTCAAAATTATTGGA
FJ705233    (251)  TACATCACCAAGTCATAGATGTCTTGACGCCGCTCTTCAAAATTATTGGA
GQ214376    (251)  TACATCACCAAGTCATAGATGTCTTGACACCGCTCTTCAAAATTATTGGA
```

Figure 15C

| | | 301 — 350 |
|---|---|---|
| AF478543 | (301) | GATGAGGTTGGGTTACGGTTGCCACAAAAACTAAACGAGATCAAACAATT |
| AF478545 | (301) | GATGAGGTTGGGTTACGGTTGCCACAAAAACTAAACGAGATCAAACAATT |
| AY386316 | (301) | GATGAGGTTGGGTTACAGTTGCCACAAAAACTAAACGAGATCAAACAATT |
| ca CDV HA | (301) | GACGAAGTGGGCCTGAGACTGCCCCAGAAGCTGAACGAGATCAAGCAGTT |
| DQ228166 | (301) | GATGAGATTGGGTTACGGTTGCCACAAAAACTAAACGAGATTAAACAATT |
| DQ494317 | (301) | GATGAGGTTGGGTTACGGTTGCCACAAAAACTAAACGAGATCAAACAATT |
| DQ494318 | (301) | GATGAGGTTGGGTTACGGTTGCCACAAAAACTAAACGAGATCAAACAATT |
| DQ889177 | (301) | GATGAGGTTGGGTTACGGTTGCCACAAAAACTAAACGAGATCAAACAATT |
| DQ889187 | (301) | GATGAGATTGGGTTACGGTTGCCACAAAAACTAAACGAGATCAAACAGTT |
| EU325730 | (301) | GATGAGATTGGGTTGCGGTTGCCACAAAAACTAAACGAGATCAAACAATT |
| EU716337 | (301) | GATGAGGTTGGGTTACGGTTGCCACAAAAACTAAACGAGATCAAACAATT |
| FJ011004 | (301) | GATGAGGTTGGGTTACGGTTGCCACAGAAACTAAACGAGATCAAGCAATT |
| FJ011005 | (301) | GATGAGGTTGGGTTACGGTTGCCACAAAAACTGAACGAGATCAAACAATT |
| FJ423608 | (301) | GATGAGATTGGGTTACGGTTGCCACAAAAACTAAACGAGATCAAACAATT |
| FJ705233 | (301) | GATGAGATTGGGTTACGGTTGCCACAAAAACTAAACGAGATCAAACAATT |
| GQ214376 | (301) | GATGAGGTTGGGTTACGGTTGCCACAAAAACTAAACGAGATCAAACAATT |

| | | 351 — 400 |
|---|---|---|
| AF478543 | (351) | TATCCTTCAAAAGACAAACTTCTTCAATCCGAACAGGGAATTCGACTTCC |
| AF478545 | (351) | TATCCTTCAAAAGACAAACTTCTTCAATCCGAACAGGGAATTCGACTTCC |
| AY386316 | (351) | TATCCTTCAAAAGACAAACTTCTTCAATCCGAACAGGGAATTCGACTTCC |
| ca CDV HA | (351) | CATCCTGCAGAAAACCAACTTCTTCAACCCCAACCGGGAGTTCGACTTCA |
| DQ228166 | (351) | TATCCTTCAAAAGACAAACTTCTTCAATCCGAACAGGGAATTCGACTTCC |
| DQ494317 | (351) | TATCCTTCAAAAGACAAACTTCTTCAATCCGAACAGGGAATTCGACTTCC |
| DQ494318 | (351) | TATCCTTCAAAAGACAAACTTCTTCAATCCGAACAGGGAATTCGACTTCC |
| DQ889177 | (351) | TATCCTTCAAAAGACAAACTTCTTCAATCCGAACAGGGAATTCGACTTCC |
| DQ889187 | (351) | TATCCTTCAAAAGACAAACTTCTTCAATCCGAAAAGGGAATTCGACTTCC |
| EU325730 | (351) | TATCCTTCAAAAGACAAACTTCTTCAATCCGAACAGGGAATTCGACTTCC |
| EU716337 | (351) | TATCCTTCAAAAGACAAACTTCTTCAATCCGAACAGGGAGTTCGATTTCC |
| FJ011004 | (351) | TATCCTTCAAAAGACAAACTTCTTCAATCCGAACAGGGAATTCGACTTCC |
| FJ011005 | (351) | TATCCTTCAAAAGACAAACTTCTTCAATCCGAACAGGGAATTCGACTTCC |
| FJ423608 | (351) | TATCCTTCAAAAGACAAACTTCTTCAATCCGAACAGGGAATTCGACTTCC |
| FJ705233 | (351) | TATCCTTCAAAAGACAAACTTCTTCAATCCGAACAGGGAATTCGACTTCC |
| GQ214376 | (351) | TATCCTTCAAAAGACAAACTTCTTCAATCCGAACAGGGAATTCGACTTCC |

| | | 401 — 450 |
|---|---|---|
| AF478543 | (401) | GCGATCTCCACTGGTGCATTAATCCACCTAGTAAGATCAAGGTGAATTTT |
| AF478545 | (401) | GCGATCTCCACTGGTGCATTAATCCACCTAGTAAGATCAAGGTGAATTTT |
| AY386316 | (401) | GCGATCTCCACTGGTGCATTAATCCACCTAGTAAGATCAAGGTGAATTTT |
| ca CDV HA | (401) | GAGACCTGCACTGGTGCATCAACCCCCCCAGCAAGATCAAAGTGAACTTC |
| DQ228166 | (401) | GCGATCTCCACTGGTGCATTAACCCACCTAGTAAGATCAAGGTGAATTTT |
| DQ494317 | (401) | GCGATCTCCACTGGTGCATTAATCCACCTAGTAAGATCAAGGTGAATTTT |
| DQ494318 | (401) | GCGATCTCCACTGGTGCATTAATCCACCTAGTAAGATCAAGGTGAATTTT |
| DQ889177 | (401) | GCGATCTCCACTGGTGCATTAATCCACCTAGTAAGATCAAGGTGAATTTT |
| DQ889187 | (401) | GCGACCTCCACTGGTGCATTAACCCACCTAGTAAGATCAAGGTGAATTTT |
| EU325730 | (401) | GCGATCTCCACTGGTGCATTAACCCACCTAGCAAGATCAAGGTGAATTTT |
| EU716337 | (401) | GCGATCTCCACTGGTGCATTAACCCACCTAGTAAGATCAAAGTGAATTTT |
| FJ011004 | (401) | GCGATCTCCACTGGTGCATTAATCCACCTAGTAAGATCAAGGTGAATTTT |
| FJ011005 | (401) | GCGATCTCCACTGGTGCATTAACCCACCTAGTAAGATCAAGGTGAATTTT |
| FJ423608 | (401) | GCGATCTCCACTGGTGCATTAACCCACCTAGCAAGATCAAGGTGAATTTT |
| FJ705233 | (401) | GCGATCTCCACTGGTGCATTAACCCACCTAGCAAGATCAAGGTGAATTTT |
| GQ214376 | (401) | GCGATCTCCACTGGTGCATTAATCCACCTAGTAAGATCAAGGTGAATTTT |

Figure 15D

```
                  451                                              500
AF478543    (451) ACTAATTACTGCGATACAATTGGGATCAGAAAATCTATTGCATCGGCAGT
AF478545    (451) ACTAATTACTGCGATACAATTGGGATCAGAAAATCTATTGCATCGGCAGT
AY386316    (451) ACTAATTACTGCGATACAATTGGGATCAAAAAGTCTATTGCATCGGCAGC
ca CDV HA   (451) ACCAACTACTGCGACACCATCGGCATCAGGAAGAGCATCGCCAGCGCCGT
DQ228166    (451) ACTAATTACTGCGATACAATTGGGATCAGAAAATCTATTGCATCGGCAGC
DQ494317    (451) ACTAATTACTGCGATACAGTTGGGATCAGAAAATCTATTGCATCGGCAGC
DQ494318    (451) ACTAATTACTGCGATACAATTGGGATCAGAAAATCTATTGCATCGGCAGC
DQ889177    (451) ACTAATTACTGCGATACAATTGGGATCAGAAAATCTATTGCATCGGCAGC
DQ889187    (451) ACTAATTACTGCGATACAATTGGGATCAGAAAATCTATTGCATTGGCAGC
EU325730    (451) ACTAATTACTGTGATACAGTTGGGGTCAAAAAATCTATTGCATCGGCAGC
EU716337    (451) ACTAATTACTGCGATACAATTGAGATCAGAAAATCTATTGCATTGGCAGC
FJ011004    (451) ACTAATTACTGTGATACAATTGAGATCAGAAAATCTATTGCATCGGCAGC
FJ011005    (451) TCTAATTACTGTGATACAATTGGGATCAGAAAATCTATTGCATCAGCAGC
FJ423608    (451) ACTAATTACTGTGATACAGTTGGGGTCAAAAAATCTATTACATCGGCAGC
FJ705233    (451) ACTAATTACTGTGATACAGTTGGGGTCAAAAAATCTATTGCATCGGCAGC
GQ214376    (451) ACTAATTACTGCGATACAATTGGGATCAGACAATCTATTGCATCGGCAGC

                  501                                              550
AF478543    (501) AAATCCCATCCTTTTATCAGCACTCTCCGGAGGCAGAGGTGACATATTCC
AF478545    (501) AAATCCCATCCTTTTATCAGCACTCTCCGGAGGCAGAGGTGACATATTCC
AY386316    (501) AAATCCCATCCTTTTATCAGCACTCTCCGGAGGCAGAGGTGACATATTCC
ca CDV HA   (501) GAATCCCATCCTGCTGAGCGCCCTGAGCGGCGGCAGAGGCGACATCTTCC
DQ228166    (501) AAATCCTATCCTTTTATCAGCACTTTCTGGAGGCAGAGGTGACATATTCC
DQ494317    (501) AAATCCCATCCTTTTATCAGCACTCTCCGGAGGCAGAGGTGACATATTCC
DQ494318    (501) AAATCCCATCCTTTTATCAGCACTCTCCGGAGGCAGAGGTGACATATTCC
DQ889177    (501) AAATCCCATCCTTTTATCAGCACTCTCGGGAGGCAGAGGTGACATATTCC
DQ889187    (501) AAATCCCATCCTTTTGTCGGCACTCTCCAGAGGCAGGGGTGACATATTCC
EU325730    (501) AAATCCCATCATTTTATCAGCACTCTCCGGAGCCAGAGGCGACATATTCC
EU716337    (501) AAATCCCATCCTTTTATCAGCACTCTCCGGTGGCAGAGGTGACATATTCC
FJ011004    (501) AAATCCCATCCTTTTATCAGCACTCTCCGGAGGCAGAGGTGACATATTCC
FJ011005    (501) AAATCCTATCCTTTTATCAGCACTCTCCGGAGGCAGAGGTGACATATTCC
FJ423608    (501) AAATCCCATCATTTTATCAGCACTCTCCGGAGCCAGAGGTGACATATTCC
FJ705233    (501) AAATCCCATCATTTTATCAGCACTCTCCGGAGCCAGAGGTGACATATTCC
GQ214376    (501) AAATCCCATCCTTTTATCAGCACTCTCCGGAGGCAGAGGTGACATATTCC

                  551                                              600
AF478543    (551) CACCATACAGATGCAGTGGAGCTACTACTTCAGTGGGCAGAGTTTTCCCC
AF478545    (551) CACCATACAGATGCAGTGGAGCTACTACTTCAGTGGGCAGAGTTTTCCCC
AY386316    (551) CACCATACAGATGCAGTGGAGCTACTACTTCAGTGGGCAGAGTTTTCCCC
ca CDV HA   (551) CCCCCTACAGATGCAGCGGCGCCACCACCTCTGTGGGCAGAGTGTTCCCT
DQ228166    (551) CACCATACAAGTGCAATGGAGCTGCTACTTCAGTAGGCAGAGTTTTCCCC
DQ494317    (551) CACCATACAGATGCAGTGGAGCTACTACTTCAGTGGGCAGAGTTTTCCCC
DQ494318    (551) CACCATACAGATGCAGTGGAGCTACTACTTCAGTGGGCAGAGTTTTCCCC
DQ889177    (551) CACCATACAGATGCAGTGGAGCTACTACTTCAGTGGGCAGAGTTTTCCCC
DQ889187    (551) CACCATACAGATGTAGTGGAGCTGCTACTTCAGTAGGCAGAGTTTTCCCC
EU325730    (551) CGCCGTACAGATGCAGTGGAGCTACTACTTCAGTAGGCAGAGTATTCCCC
EU716337    (551) CACCATACAGTTGCAGTGGAGCTACTACTTCAGTAGGCAGAGTTTTCCCT
FJ011004    (551) CACCATACAGATGCAGTGGAGCTACTACTTCAGTGGGCAGAGTTTTCCCC
FJ011005    (551) CTCCATACAGATGCAATGGAGCTGCTACTTCAATAGGCAGAGTTTTCCCT
FJ423608    (551) CGCCGTACAGATGCAGTGGAGCTACTACTTCAGTAGGCAGAGTATTCCCC
FJ705233    (551) CGCCGTGCAGATGCAGTGGAGCTACTACTTCAGTAGGCAGAGTATTCCCC
GQ214376    (551) CACCATACAGATGCAGTGGAGCTACTACTTCAGTGGGCAGAGTTTTCCCC
```

Figure 15E

```
                      601                                              650
AF478543    (601) CTATCAGTATCATTGTCCATGTCTTTGATCT-CAAAAACATCAGAGATAA
AF478545    (601) CTATCAGTATCATTGTCCATGTCTTTGATCT-CAAAAACATCAGAGATAA
AY386316    (601) CTATCAGTATCATTGTCCATGTCTTTGATCT-CAAAAACATCAGAGATAA
ca CDV HA   (601) CTGAGCGTGTCCCTGAGCATGAGCCTGATCAGCAAGACCAGC-GAGATCA
DQ228166    (601) CTTTCAGTATCATTGTCCATGTCTTTGATCT-CAAAAACATCAGGGATAA
DQ494317    (601) CTATCAGTATCATTGTCCATGTCTTTGATCT-CAAAAACATCAGAGATAA
DQ494318    (601) CTATCAGTATCATTGTCCATGTCTTTGATCT-CAAAAACATCAGAGATAA
DQ889177    (601) CTATCAGTATCATTGTCCATGTCTTTGATTT-CAAAAACATCAGGGATAA
DQ889187    (601) CTCTCAGTATCATTGTCCATGTCTTTGATCT-CAAGAACATCAGAGATAA
EU325730    (601) CTATCCGTATCATTATCCATGTCTTTGATAT-CAAGAACATCAGAGATAA
EU716337    (601) CTATCAGTATCATTGTCCATGTCTTTGATCT-CAAAAACATCAGAGATAA
FJ011004    (601) CTATCAGTATCATTGTCCATGTCTTTGATCT-CAAGAACATCAGAGATAA
FJ011005    (601) CTATCTGTGTCATTGTCCATGTCCTTGATCT-CCAGAACAGCAGAGATAA
FJ423608    (601) CTATCTGTATCATTATCCATGTCTTTGATAT-CAAGAACATCAGAGATAA
FJ705233    (601) CTATCCGTATCATTATCCATGTCTTTGATAT-CAAGAACATCAGAGATAA
GQ214376    (601) CTGTCAGTATCATTGTCCATGTCTGTGATCT-CAAAAACATCAGAGATAA
```

```
                      651                                              700
AF478543    (650) CCAATATGCTAACTGCTATCTCAGACGGAGTGTATGGTAAAACCTATTTG
AF478545    (650) CCAATATGCTAACTGCTATCTCAGACGGAGTGTATGGTAAAACCTATTTG
AY386316    (650) CCAGTATGCTAACTGCTATCTCAGACGGAGTGTATGGTAAAACCTATTTG
ca CDV HA   (650) CCAACATGCTGACCGCCATCAGCGACGGCGTGTACGGCAAGACCTATCTG
DQ228166    (650) TCAATATGCTAACCGCTATCTCAGACGGAGTGTATGGTAAAACTTACTTG
DQ494317    (650) CCAATATGCTAACTGCTATCTCAGACGGAGTGTATGGTAAAACCTATTTG
DQ494318    (650) CCAATATGCTAACTGCTATCTCAGACGGAGTGTATGGTAAAACCTATTTG
DQ889177    (650) CCAATATGCTAACTGCCATCTCAGACGGAGTGTATGGTAAAACCTATTTG
DQ889187    (650) TCAATATGCTAACCGCTATCTCAGATGGAGTGTATGGTAAAACTTACTTG
EU325730    (650) TCAATATGCTAACCGCTATCTCAGACGGAGTGTATGGTAAAACTTATATG
EU716337    (650) TCAATATGCTAACCGCTATCTCAGACGGGGTGTATGGTAAAACTTATTTG
FJ011004    (650) CCAATATGCTAACTGCTATCTCAGACGGAGTGTATGGTAAAACCTATTTG
FJ011005    (650) TCAATATGCTAACCGCTATCTCAGACGGAGTTGATGGTAAAACTTACTTG
FJ423608    (650) TCAATATGCTAACCGCTATCTCAGACGGAGTGTATGGTAAAACTTATTTG
FJ705233    (650) TCAATATGCTAACCGCTATCTCAGACGGAATGTATGGTAAAACTTATTTG
GQ214376    (650) CCAATATGCTAACTGCTATCTCAGACGGAGTGTATGGTAAAACCTATTTG
```

```
                      701                                              750
AF478543    (700) CTAGTGCCTGATTACATTGAAGGGCAGTTCGACACGCAAAAGATTCGAGT
AF478545    (700) CTAGTGCCTGATTACATTGAAGGGGAGTTCGACACGCAAAAGATTCGAGT
AY386316    (700) CTAGTGCCTGATTACATTGAAGGGGAGTTCGACACGCAAAAGATTCGAGT
ca CDV HA   (700) CTGGTGCCCGACTACATCGAGGGCGAGTTCGACACCCAGAAGATCCGCGT
DQ228166    (700) CTAATGCCTGATTATATTGAAGGGGAGTTCGACACGCAAAAGATTCGAGT
DQ494317    (700) CTAGTGCCTGATTACATTGAAGGGCAGTTCGACACGCAAAAGATTCGAGT
DQ494318    (700) CTAGTGCCTGATTACATTGAAGGGGAGTTCGACACGCAAATGATTCGAGT
DQ889177    (700) CTAGTGCCTGATTACATTGAAGGGGAGTTCGACACGCAAAAGATTCGAGT
DQ889187    (700) CTAGTGCCTGATTATATTGAAGGGGAATTCGACACACAAAAGATTCGAGT
EU325730    (700) CTAGTGCCTGATTATATTGAAGGGGAGTTCGACTCGCAAAAGATTCGAGT
EU716337    (700) CTAGTTCCTGATTATATTGAAGGGGGGTTCGACACGCAAAAGATTCGAGT
FJ011004    (700) CTAGTGCCTGATTACTTTGAAGGGGAGTTCGACACGCAAAAGATTCGGGT
FJ011005    (700) CTAGTGCCTGATTATATTGAAGGGGAGTTCGAAACGCAGAAGATTCGAGT
FJ423608    (700) CTAGTGCCTGATTATATTGAAGGGGAGTTCGACTCGCAAAAGATTCGAGT
FJ705233    (700) CTAGTGCCTGATTATATTGAAGGGGAGTTCGACTCGCAAAAGATTCGAGT
GQ214376    (700) CTAGTGCCTGATTACATTGAAGGGGAGTTCGACACGCAAAAGATTCGAGT
```

Figure 15F

```
                  751                                              800
AF478543   (750)  CTTTGAGATAGGGTTCATCAAACGGTGGCTGAATAACATGCCATTACTCC
AF478545   (750)  CTTTGAGATAGGGTTCATCAAACGGTGGCTGAATAACATGCCATTACTCC
AY386316   (750)  CTTTGAGATAGGGTTCATCAAACGGTGGCTGAATAACATGCCATTACTCC
ca CDV HA  (750)  GTTCGAGATCGGCTTCATCAAGCGGTGGCTGAACAACATGCCCCTGCTGC
DQ228166   (750)  CTTTGAGATAGGGTTCATCAAACGGTGGCTGAATGACATGCCATTACTCC
DQ494317   (750)  CTTTGAGATTGGGTTCATCAGACGGTGGCTGAATAACATGCCATTACTCC
DQ494318   (750)  CTTTGAGATAGGGTTCATCAAACGGTGGCTGAATAACATGCCATTACTCC
DQ889177   (750)  CTTTGAGATAGGGTTCATTAAACGGTGGCTGAATAACATGCCATTATTCC
DQ889187   (750)  CTTTGAGATAGGGTTCATCAAACGGTGGCTGAATGACATGCCATTACTCC
EU325730   (750)  CTTTGAGATAGGGTTTATCAAACGGTGGCTGAATAACATGCCTTTACTCC
EU716337   (750)  CTTTGAGATAGGGTTCATCAAACGGTGGCTGAATGACATGCCATTACTCC
FJ011004   (750)  CTTTGAGATAGGGTTCATCAAACGGTGGCTGAATGACATGCCATTACTCC
FJ011005   (750)  CTTTGAGATCGGGTTCATCAAACGGTGGCTGAATGACATGTCATTACTCC
FJ423608   (750)  CTTTGAGATAGGGTTTATCAAACGGTGGCTGAATGACATGCCTTTACTCC
FJ705233   (750)  CTTTGAGATAGGGTTTATCAGACGGTGGCTGAATGACATGCCTTTACTCC
GQ214376   (750)  CTTTGAGATAGGGTTCATCAAACGGTGGCTGAATAACATGCCATTACTCC

                  801                                              850
AF478543   (800)  AGACAACCAACTACATGGTCCTCCCGGAGAATTCCAAAGCCAAGGTATGT
AF478545   (800)  AGACAACCAACTACATGGTCCTCCCGGAGAATTCCAAAGCCAAGGTATGT
AY386316   (800)  AGACAACCAACTACATGGTCCTCCCGGAGAATTCCAAAGCCAAGGTATGT
ca CDV HA  (800)  AGACCACCAACTACATGGTGCTGCCCGAGAACAGCAAGGCCAAAGTGTGC
DQ228166   (800)  AGACAACCAACTATATTGTCCTCCCGGAGAATTCCAAAGCCAAGGTATGT
DQ494317   (800)  AGACAACCAACTACATGGTCCTCCCGGAGAATTCCAAAGCCAAGGTATGT
DQ494318   (800)  AGACAACCAACTACATGGTCCTCCCGGAGAATTCCAAAGCCAAGGTATGT
DQ889177   (800)  AGACAACCAACTACATGGTCCTCCCGGAGAATTCCAAAGCCAAGGTATGT
DQ889187   (800)  AGACAACCAACTATATGGTCCTCCCGGAGAATTCCAAAGCCAAGGTATGT
EU325730   (800)  AGACAACCAACTATATGGTCCTCCCGGAAACTTCCAAAGCCAAGGTATGT
EU716337   (800)  AGACAACCAACTATATGGTCCTCCCGGAGAATTCCAAAGCCAAGGTATGT
FJ011004   (800)  AGACAACCAACTACATGTTCCTCCCGGAGAATTCCAAAGCCAAGGTATGT
FJ011005   (800)  AGACAACCAACTATATGGTCCTCCCGGAGAATTCCAAAGCCAAGGTATGT
FJ423608   (800)  AGACAACCAACTATATGGTTCTCCCGGAAACTTCCAAAGCCAAGGTATGT
FJ705233   (800)  AGACAACCAACTATATGGTCCTTCCGGAAACTTCCAAAGCCAAGGTATGT
GQ214376   (800)  AGACAACCAACTATATGGTCCTCCCGGAGAATTCCAAAGCCAAGGTATGT

                  851                                              900
AF478543   (850)  ACTATAGCAGTGGGCGAGTTGACACTGGCTTCCTTGTGTGTAGATGAGAG
AF478545   (850)  ACTATAGCAGTGGGCGAGTTGACACTGGCTTCCTTGTGTGTAGATGAGAG
AY386316   (850)  ACTATAGCAGTGGGCGAGTTGACACTGGCTTCCTTGTGTGTAGATGAGAG
ca CDV HA  (850)  ACCATCGCTGTGGGCGAGCTGACCCTGGCCAGCCTGTGCGTGGACGAGAG
DQ228166   (850)  ACTATAGCAGTGGGTGAGTTGACACTGGCTTCCTTGTGTGTAGATGAGAG
DQ494317   (850)  ACTATAGCAGTGGGCGAGTTGACACTGGCTTCCTTGTGTGTAGATGAGAG
DQ494318   (850)  ACTATAGCAGTGGGCGAGTTGACACTAGCTTCCTTGTGTGTAGATGAGAG
DQ889177   (850)  ACTATAGCAGTGGGCGAATTGACACTAGCTTCCTTGTGTGTAGATGAGAG
DQ889187   (850)  ACTATAGCAGTGGGCGAGTTGACACTGGCTTCCTTGTGTGTAGATGAGAG
EU325730   (850)  ACTATAGCAGTGGGCGAGCTGACACTAGCTTCCTTGTGTGTAGATGAGAG
EU716337   (850)  ACTATAGCGGTGGGCGAGTTGACACTGGCTTCCTTGTGTGTAGATGAGAG
FJ011004   (850)  ACTATAGCAGTGGGCGAGTTGACACTGGCTTCCTTGTGTGTAGATGAGAG
FJ011005   (850)  ACTATAGCAGTGGGCGAGTTGACACTGGCTTCCTTGTGTGTAGATGAGAG
FJ423608   (850)  ACTATAGCAGTGGGCGAGCTGACACTAGCTTCCTTGTGTGTAGATGAGAG
FJ705233   (850)  ACTATAGCAGTGGGCGAGCTGACACTAGCTTCCTTGTGTGTAGATGAGAG
GQ214376   (850)  ACTATAGCAGTGGGCGAGTTGACACTGGCTTCCTTGTGTGTAGATGAGAA
```

Figure 15G

```
                901                                              950
AF478543   (900) CACCGTATTGTTATATCATGACAGCAATGGTTCACAAGATGGTATTCTAG
AF478545   (900) CACCGTATTGTTATATCATGACAGCAATGGTTCACAAGATGGTATTCTAG
AY386316   (900) CACCGTATTGTTATATCATGACAGCAATGGTTCACAAGATGGTATTCTAG
ca CDV HA  (900) CACCGTGCTGCTGTACCACGACAGCAACGGCAGCCAGGACGGCATCCTGG
DQ228166   (900) CACCGTATTGTTATATCATGACAGCAATGGTTCACAAGATGGTATTCTAG
DQ494317   (900) CACCGTATTGTTATATCATGACAGCAATGGTTCACAAGATGGTATTCTAG
DQ494318   (900) CACCGTATTGTTATATCATGACAGCAATGGTTCACAAGATGGTATTCTAG
DQ889177   (900) CACCGTATTGTTATATCATGATAGCAATGGTTCACAAGGTGGTGTTCTAG
DQ889187   (900) CACTGTATTACTATATCATGACAGCAATGGTTCACAAGATGGTATTCTAG
EU325730   (900) CACCGTATTGTTATATCATGACAGCAATGGTTCACAAAATGGTATTCTAG
EU716337   (900) CACCGTATTGTTATATCATGACAGCGATGGTTCACAAGATGGTATTCTAG
FJ011004   (900) CACCGTATCGTTATATCATGACGGCAGTGGTTCACAAGATGGTATTCTAG
FJ011005   (900) CACTGTATTGTTATATCATGACAGCAATGGTTCACAAGATGGTATTCTAG
FJ423608   (900) CACTGTATTATTATATCATGACAGCAATGGTTCACAAAATGGTATTCTAG
FJ705233   (900) CACCGTATTGTTATATCATGACAGCAATGGTTCACAAAATGGTATTCTAG
GQ214376   (900) CACCGTATTGTTATATCATGACAGCAATGGTTCACAAGATGGTATTCTAG

                951                                             1000
AF478543   (950) TAGTGACGCTGGGGATATTTGGGGCAACACCTATGGATCAAGTTGAAGAA
AF478545   (950) TAGTGACGCTGGGGATATTTGGGGCAACACCTATGGATCAAGTTGAAGAA
AY386316   (950) TAGTGACGCTGGGGATATTTGGAGCAACACCTATGGATCAAGTTGAAGAA
ca CDV HA  (950) TGGTGACCCTGGGCATCTTCGGCGCCACCCCTATGGACCAGGTGGAGGAA
DQ228166   (950) TAGTGACACTGGGAATATTCGGGGCAACACCTATGGATCAAGTTGAAGAG
DQ494317   (950) TAGTGACGCTGGGGATATTTGGGGCAACACCTATGGATCAAGTTGAAGAA
DQ494318   (950) TAGTGACGCTGGGGATATTTGGGGCAACACCTATGGATCAAGTTGGAGAA
DQ889177   (950) TAGTGACGCTGGGGATATTTGGGGCAACACCTATGGATCAAGTTGAAGAA
DQ889187   (950) TAGTGACGCTGGGAATATTTGGGGCAACACCTATGGATCAAGTTGAAGAG
EU325730   (950) TAGTGACATTGGGAATATTTGGGGCAACACCTATGGATCAAGTTGAAGAG
EU716337   (950) TGGTGACGCTGGGAATATTTGGGGCAACACCTATGGATCAAGTTGAAGAG
FJ011004   (950) TAGTGACGCTGGGGATATTTGGGGCAACACCTATGGATCAAGTTGAAGAG
FJ011005   (950) TAGTGACGCTGGGAATATTTTGGGGCACACCTATGGATCAAGTTGAAGAG
FJ423608   (950) TAGTGACATTGGGAATATTTGGGGCAACATCTATGGATCAAGTTGAAGAG
FJ705233   (950) TAGTGACATTGGGAATATTTGGGGCAACACCTATGGATCAAGTTGAAGAG
GQ214376   (950) TAGTGACGCTGGGGATATTTGGGGCAACACCTATGGATCAAGTTGAAGAA

                1001                                            1050
AF478543  (1000) GTGATACCTGTCGCTCACCCATCAGTAGAAAAAATACATATAACAAATCA
AF478545  (1000) GTGATACCTGTCGCTCACCCATCAGTAGAAAAAATACATATAACAAATCA
AY386316  (1000) GTGATACCTGTCGCTCACCCATCAGTAGAAAAAATACATATAACAAATCA
ca CDV HA (1000) GTGATCCCCGTGGCCCACCCCAGCGTGGAGAAGATCCACATCACCAACCA
DQ228166  (1000) GTGATACCTGTCGCTCACCCATCAGTANAAAAAATACATATAACAAATCA
DQ494317  (1000) GTGATACCTGTCGCTCACCCATCAGTAGAAAAAATACATATAACAAATCA
DQ494318  (1000) GTGATACCTGTCGCTCACCCCTCAGTAGAAAAAATACATATAACAAATCA
DQ889177  (1000) ATGATACCTGTCGCTCACCCATCAGTAGAAAAAATACATATAACAAATCA
DQ889187  (1000) GTGATACCTGTCGCTCATCCATCAGTAGAAAAAATACATATAACAAATCA
EU325730  (1000) GTGATACCTATCGCTCACCCATCAGTGGAGAGAATACATATAACAAATCA
EU716337  (1000) GTGATACCTGTTGCTCACCCATCAGTAGAAAAAATACATATAACAAATCA
FJ011004  (1000) GTGATACCTGTCGCTCACCCATCAGTAGAGAAAATACATATAACCAATCA
FJ011005  (1000) GTGATACCTGTCGCTCACCCATCAGTAGAAAAAATACATATAACAAATCA
FJ423608  (1000) GTGATACCTATCGCTCACCCATCAGTGGAGAGAATACATATAACAAATCA
FJ705233  (1000) GTGATACCTATCGCTCACCCATCAGTGGAGAGAATACATATAACAAATCA
GQ214376  (1000) GTGATACCTGTCGCCCACCCATCAATAGAAAAAATACATATAACAAATCA
```

Figure 15H

```
                      1051                                              1100
AF478543   (1050)  CCGTGGGTTCATAAAAGATTCAATAGCAACCTGGATGGTGCCTGCATTGG
AF478545   (1050)  CCGTGGGTTCATAAAAGATTCAATAGCAACCTGGATGGTGCCTGCATTGG
AY386316   (1050)  CCGTGGGTTCATAAAAGATTCAATAGCAACCTGGATGGTGCCTGCATTGG
ca CDV HA  (1050)  CCGGGGCTTTATCAAGGACAGCATCGCCACCTGGATGGTGCCCGCCCTGG
DQ228166   (1050)  CCGTGGGTTCATAAAAGATTCAATAGCAACCTGGATGGTGCCTGCATTGA
DQ494317   (1050)  CCGTGGGTTCATAAAAGATGCAATAGCAACCTGGATGGTGCCTGCATTGG
DQ494318   (1050)  CCGTGGGTTCATAAAAGATTCAATAGCAACCTGGATGGTGCCTGCATTGG
DQ889177   (1050)  CCGTGGGTTCATAAAAGATTCAATAGCAACCTGGATGGTGCCTGTATTGG
DQ889187   (1050)  CCGTGGGTTCATAAAAGATTCAATAGCAACCTGGATGGTGCCTGTATTGG
EU325730   (1050)  CCGTGGGTTCATAAAAGATTCAGTAGTAACCTGGATGGTGCCTGTATTGG
EU716337   (1050)  CCGTGGGTTCATAAAAGATTCAATAGCAACCTGGATGGTGCCTGCATTGG
FJ011004   (1050)  CCGTGGATTCATAAAAGATTCAATCGCAACCTGGATGGTGCCTGCATTGG
FJ011005   (1050)  CCGTGGGTTCATAAAAGATTCAAAAGCAATCTGGATGGTGCCTGCATTGG
FJ423608   (1050)  CCGTGGGTTCATAAAAGATTCAATAGTAACCTGGATGGTGCCTGTATTGG
FJ705233   (1050)  CCGTGGGTTCATAAAAGATTCAATAGTAACCTGGATGGTGCCTGTATTGG
GQ214376   (1050)  CCGTGGGTTCATAAAAGATTCAATAGCAACCTGGATGGTGCCTGCATTGG
```

```
                      1101                                              1150
AF478543   (1100)  TCTCTGAGAAACAAGAGGAACAAAAAAATTGTCTGGAGTCGGCTTGTCAA
AF478545   (1100)  TCTCTGAGAAACAAGAGGAACAAAAAAATTGTCTGGAGTCGGCTTGTCAA
AY386316   (1100)  TCTCTGAGAAACAAGAGGAACAAAAAAATTGTCTGGAGTCGGCTTGTCAA
ca CDV HA  (1100)  TGTCTGAGAAGCAGGAGGAGCAGAAGAACTGCCTGGAGAGCGCCTGCCAG
DQ228166   (1100)  TCTCTGGGGAACAAGAGGAACAAAAAAATTGTCTGGAGTCGGCTTGTCAA
DQ494317   (1100)  TCTCTGAGAAACAAGAGGAACAAAAAAATTGTCTGGAGTCGGCTTGTCAA
DQ494318   (1100)  TCTCTGAGAAACAAGAGGAACAAAAAAATTGTCTGGAGTCGGCTTGTCAA
DQ889177   (1100)  TCTCTGAGAAACAAGAGGAACAAAAAAATTGTCTGGAGTCGGCTTGTCAA
DQ889187   (1100)  TCTCTGAGAACCAAGAGGAACAAAAAAATTGTCTGGAGTCGGCTTGTCAA
EU325730   (1100)  TCTCTGAGAAACAAGAGGAGCAAAAAAACTGTCTGGAGTCTGCTTGTCAA
EU716337   (1100)  TATCTGAGAAACAAGAGGAACAAAAAAATTGTCTGGAGTCGGCTTGTCAA
FJ011004   (1100)  TCTCTGAGAAACAAGAGGAACAAAAAAATTGTCTGGAGTCGGCTTGTCAA
FJ011005   (1100)  TCTCTGAGAAACAAGAGGAACAAAAAAATTGTCTGGAGTCGGCTTGTCAA
FJ423608   (1100)  TCTCTGAGAAACAAGAGGAGCAAAAAAACTGTCTGGAGTCTGCTTGTCAA
FJ705233   (1100)  TCTCAGAGAAACAAGAGGAGCAAAAAAACTGTCTGGAGTCTGCTTGTCAA
GQ214376   (1100)  TCTCTGAGAAACAAGAGGAACAAAAAAATTGTCTGGAGTCGGCTTGTCAA
```

```
                      1151                                              1200
AF478543   (1150)  AGAAAAACCTACCCTATGTGCAACCAAACGTCATGGGAACCCTTTGGAGG
AF478545   (1150)  AGAAAAACCTACCCTATGTGCAACCAAACGTCATGGGAACCCTTTGGAGG
AY386316   (1150)  AGAAAAACTTACCCTATGTGCAACCAAACGTCATGGGAACCCTTTGGAGG
ca CDV HA  (1150)  AGAAAGACCTACCCCATGTGCAACCAGACCAGCTGGGAGCCCTTTGGCGG
DQ228166   (1150)  AGAAAATCCTACCCTATGTGCAACCAAACGTCATGGAAACCCTTTGGAGG
DQ494317   (1150)  AGAAAAACCTATCCTATGTGCAACCAAACGTCATGGGAACCCTTTGGAGG
DQ494318   (1150)  AGAAAAACCTACCCAATGTGCAACCAAACGTCATGGGAACCCTTTGGAGG
DQ889177   (1150)  AGAAAAACCTACCCTATGTGCAACCAAACGTCATGGGAACCCTTTGGAGG
DQ889187   (1150)  AGAAAATCCTACCCTATGTGCAACCAAACGTCATGGGAACCCTTTGGAGG
EU325730   (1150)  AGAAAATCCTACCCGATGTGCAACCAAACGTCATGGGAACCCTTTGGAGG
EU716337   (1150)  AGAAAATCCTACCCTATGTGCAACCAAACGTCATGGGAACCCTTTGGAGG
FJ011004   (1150)  AGAAAAACCTACCCTATGTGCAACCAAACGTCATGGGAACCCTTTGGAGG
FJ011005   (1150)  AGAAAAACCTACCCTATGTGCAACCAAACGTCATGGGAACCCTTTGGGGG
FJ423608   (1150)  AGAAAATCCTACCCTATGTGCAACCAAACGTCATGGGAACCCTTTGGAGG
FJ705233   (1150)  AGAAAAACCTATCCTATGTGCAACCAAACGTCATGGGAACCCTTTGGAGG
GQ214376   (1150)  AGAAAAACCTACCCTATGTGCAACCAAACGTCATGGGAACCCTTTGGAGG
```

Figure 15I

```
                 1201                                             1250
AF478543  (1200) GGGACAGTTGCCATCTTATGGGCGGTTGACATTATCTCTAGATCCAAGCA
AF478545  (1200) GGGACAGTTGCCATCTTATGGGCGGTTGACATTATCTCTAGATCCAAGCA
AY386316  (1200) GGGACAGTTGCCATCTTATGGGCGGTTGACATTACCTCTAGATCCAAGCA
ca CDV HA (1200) CGGACAGCTGCCCAGCTACGGCAGACTGACCCTGAGCCTGGACCCTAGCA
DQ228166  (1200) AGGACAGTTGCCATCTTATGGGCGGTTGACATTACCTCTAGATCCAGGCA
DQ494317  (1200) AGGACAGTTGCCATCTTATGGGCGGTTGACATTACCTCTAGATCCAAGCA
DQ494318  (1200) GGGACAGTTACCATCTTATGGGCGGTTGACATTACCTCTAGATCCAAGCA
DQ889177  (1200) GGGACAGTTGCCATCTTATGGGCGGTTGACATTACCTCTAGATCCGAGCA
DQ889187  (1200) AGGACAGCTGCCATCTTATGGGCGGTTGACATTACCTCTAGATCCAGGCA
EU325730  (1200) AGGACAGTTGCCTTCTTATGGGCGGTTGACATTACCTCTAGATCCAAGCG
EU716337  (1200) AGGACAGTTGCCATCTTATGGGCGGTTGACATTACCTCTAGATCCAAGCA
FJ011004  (1200) AGGACAGTTGCCATCTTATGGGCGGTGGACATTACCTCTAGATCCAAGCA
FJ011005  (1200) AGGACAATTGCCATCCTATGGGCGGCTGACATTACCTCTAGATCCAAGTA
FJ423608  (1200) AGGACAGTTGCCTTCTTATGGGCGGTTGACATTACCTCTAGATCCAAGCA
FJ705233  (1200) AGGACAGTTGCCCTCTTATGGGCGGTTGACATTACCTCTAGATCCAAGCA
GQ214376  (1200) GAGACAGTTGCCATCTTATGGGCGGTTGACATTACCTCTAGATCCAAGTA

                 1251                                             1300
AF478543  (1250) TTGACCTTCAACTTAACATATCATTTACATACGGTCCAGTTATACTGAAT
AF478545  (1250) TTGACCTTCAACTTAACATATCATTTACATACGGTCCAGTTATACTGAAT
AY386316  (1250) TTGACCTTCAACTTAACATATCATTTACATACGGTCCGGTTATACTGAAT
ca CDV HA (1250) TCGACCTGCAGCTGAACATCAGCTTCACCTACGGCCCCGTGATCCTGAAC
DQ228166  (1250) TTGACCTTCAACTTAACATATCATTTACATACGGTCCGGTTATACTGAAT
DQ494317  (1250) TTGACCTTCAACTTAACATATCATTTACATACGGTCCAGTTATACTGAAT
DQ494318  (1250) TTGACCCTCAACTTAACATATCATTTACATACGGTCCAGTTATACTGAAT
DQ889177  (1250) TTGACCTTCAACTTAACATATCATTTACATACGGTCCAGTTATACTGAAT
DQ889187  (1250) TTGACCTTCAACTTAATCTATCGTTTACATACGGTCCGATTATACTGAAT
EU325730  (1250) TTGACCTTCAACTTAACATATCATTTACATATGGTCCGGTTATACTGAAC
EU716337  (1250) TTGACCTTCAACTTAACATCTCGTTTACATACGGTCCGGTTATACTGAAT
FJ011004  (1250) TTGACCTTCAACTTAACATATCAGTTACATACGGTCCAGTTATACTGAAT
FJ011005  (1250) TTGACCTTCAACTTAACATATCGTTTACATACGGTCCGGTTATACTGAAT
FJ423608  (1250) TTGACCTTCAACTTAACATATCATTTACATATGGTCCGGTTATACTGAAC
FJ705233  (1250) TTGACCTTCAGCTTAACATATCATTTACATATGGTCCGGTTATACTGAAC
GQ214376  (1250) TGGACCTTCAACTTAACATATCATTTACATACGGTCCAGTTATACTGAAT

                 1301                                             1350
AF478543  (1300) GGAGACGGTATGGATTATTATGGAAGCTCACTTTCGGACTCCGGATGGCT
AF478545  (1300) GGAGACGGTATGGATTATTATGGAAGCTCACTTTCGGACTCCGGATGGCT
AY386316  (1300) GGAGACGGTATGGATTATTATGAAAGCCCACTTTCGGACTCCGGATGGCT
ca CDV HA (1300) GGCGACGGCATGGATTACTACGGCAGCAGCCTGAGCGACAGCGGCTGGCT
DQ228166  (1300) GGAGACGGTATGGATTATTATGAAAGCCCACTTTTGGACTCCGGATGGCT
DQ494317  (1300) GGAGACGGTATGGATTATTATGAAAGCTCACTTTCGGACTCCGGATGGCT
DQ494318  (1300) GGAGACGGTATGGATTATTATGAAAGCTCACTTTCGGACTCTGGATGGCT
DQ889177  (1300) GGAGACGGTATGGATTACTATGAAAGCCCACTTTTGGACTCTGGGTGGCT
DQ889187  (1300) GGAGACGGTATGGATTATTATGAAAGCCCACTTTTGAACTCCGGATGGCT
EU325730  (1300) GGAGACGGTATGGATTATTATGAAAGCCCACTTTTGGAATCCGGATGGCT
EU716337  (1300) GGAGACGGTATGGATTATTATGAAAGCCCACTTTTGGACTCCGGATGGCT
FJ011004  (1300) GGAGACGGTATGGATTATTATGAAAGCCCACTTTCAGACTCCGGATGGCT
FJ011005  (1300) GGAGACGGTATGGATTATTATGAAAGCCCACTTTTGGACTCCGGATGGCT
FJ423608  (1300) GGGGACGGTATGGATTATTATGAAAGCCCACTTTTGGAATCCGGATGGCT
FJ705233  (1300) GGAGACGGTATGGATTATTATGAAAGCCCGCTTTTGGACTCCGGATGGCT
GQ214376  (1300) GGAGACGGTATGGATTATTATGAAAGCCCACTTCCGGACTCCGGATGGCT
```

Figure 15J

```
                     1351                                              1400
AF478543   (1350)    TACCATTCCTCCCAAGAATGGAACAGTCCTTGGATTGATAAACAAAGCAA
AF478545   (1350)    TACCATTCCTCCCAAGAATGGAACAGTCCTTGGATTGATAAACAAAGCAA
AY386316   (1350)    TACCATTCCTCCCAGGAACGGAACAGTCCTTGGATTGATAAACAAAGCAA
ca CDV HA  (1350)    GACCATCCCTCCCAAGAACGGCACAGTGCTGGGCCTGATCAACAAGGCCT
DQ228166   (1350)    TACCATTCCTCCCAAGAACGGAACAATTCTTGGATTGATAAACAAGGCAA
DQ494317   (1350)    TACCATTCCTCCCAAGAACGGAACAGTCCTTGGATTGATAAACAAAGCAA
DQ494318   (1350)    TACCATTCCTCCCAAGAACGGAACAGTCCTTGGATTGATAAACAAAGCAA
DQ889177   (1350)    TACCATTCCTCCCAAGAACGGAACAGTCCTTGGATTGATAAACAAAGCAA
DQ889187   (1350)    TACCATTCCTCCCAAGAACGGGACAATTCTTGGATTGATAAACAAAGCAA
EU325730   (1350)    TGCCATACCCCCTAAGAACGGAACAGTCCTTGGATTGATAAACAAAGCAA
EU716337   (1350)    TACCATTCCCCCCAAGAACGGAACAGTCCTTGGATTGATAAACAAAGCAA
FJ011004   (1350)    TACCATTCCTCCCAAGAACGGAACAATCCTTGGATTGATAAACAAAGCAA
FJ011005   (1350)    TACCATTCCTCCCAAAAACGGAACAGTTCTTGGATTGATGAACAAAGCAA
FJ423608   (1350)    TACCATACCCCCTAAGAACGGAACAGTCCTTGGATTGATAAACAAAGCAA
FJ705233   (1350)    TACCATACCTCCTAAGAACGGAACAGTCCTTGGATTGATAAACAAAGCAA
GQ214376   (1350)    TACCATTCCACCCAAGAACGGAACAGTCCTTGGACTGATAAACAAAGCAA

                     1401                                              1450
AF478543   (1400)    GTAGAGGAGACCAGTTCACTGTAATCCCCCATGTGTTGACATTTGCGCCC
AF478545   (1400)    GTAGAGGAGACCAGTTCACTGTAATCCCCCATGTGTTGACATTTGCGCCC
AY386316   (1400)    GTAGAGGAGACCAGTTCACTGTAATCCCCCATGTGTTGACATTTGCGCCC
ca CDV HA  (1400)    CCAGGGGCGACCAGTTCACCGTGATCCCTCACGTGCTGACCTTCGCCCCC
DQ228166   (1400)    GTAGAGGAGACCAGTTCACTGTAATCCCCCATGTGTTGACATTTGCGCCC
DQ494317   (1400)    GTAGAGGAGACCAGTTCACTGTAACCCCCCATGTGTTGACATCTGCGCCC
DQ494318   (1400)    GTAGAGGAGACCAGTTCACTGTAATCCCCCATGTGTTGACATTTGCGCCC
DQ889177   (1400)    GTAGAGGAGACCAGTTCACTGTAATCCCCCATGTGTTAACATTTGCGCCC
DQ889187   (1400)    GTAGAGGAGACCAGTTCACTGTAACCCCCCATGTGTTGACATTTGCGCCT
EU325730   (1400)    GTAGAGGAGACCAGTTCACTGTGACCCCCCATGTGTTGACATTTGCGCCC
EU716337   (1400)    GTAGAGGAGACCAATTCACTGTAATCCCCCATGTGTTGACATTTGCGCCC
FJ011004   (1400)    GTAGAGGAGACCAGTTCACTGTAATCCCCCATGTGTTGACATTTGCGCCC
FJ011005   (1400)    GTAGAGGAGACCAGTTCACTGTAATCCCCCATGTGTTGACATTTGCGCCT
FJ423608   (1400)    GTAGAGGAGACCAGTTCACTGCGACCCCCCATGTGTTGACATTTGCGCCC
FJ705233   (1400)    GTAGAGGAGACCAGTTCACTGTGACCCCCCATGTGTTGACATTTGCGCCC
GQ214376   (1400)    GTAGAGGAGACCAGTTCACTGTAATCCCCCATGTGTTGACATTTGCGCCC

                     1451                                              1500
AF478543   (1450)    AGGGAATCAAGTGGAAATTGTTATTTACCTATTCAAACATCCCAGATTAT
AF478545   (1450)    AGGGAATCAAGTGGAAATTGTTATTTACCTATTCAAACATCCCAGATTAT
AY386316   (1450)    AGGGAATCAAGTGGAAATTGTTATTTACCTATTCAAACATCCCAGATTAT
ca CDV HA  (1450)    AGAGAGAGCAGCGGCAACTGCTACCTGCCTATCCAGACCTCCCAGATCAT
DQ228166   (1450)    AGGGAATCAAGTGGGAATTGTTATTTACCTATTCAAACATCTCAGATTAT
DQ494317   (1450)    AGGGAATCAAGTGGAAATTGTTATTTACCTATTCAAACATCCCAGATTAT
DQ494318   (1450)    AGGGAATCAAGTGGAAATTGTTATTTACCTATTCAAACATCCCAGATTAT
DQ889177   (1450)    AGGGAATCAAGTGGAAATTGTTATTTACCTATTCAAACATCCCAGATTAT
DQ889187   (1450)    AGGGAATCAAGTGGGAATTGTTATTTACCTATTCAAACATCTCAGATTAT
EU325730   (1450)    AGGGAATCAAGTGGGAATTGTTATTTGCCTATTCAAACATCCCAGATTAT
EU716337   (1450)    AGGGAATCAAGTGGAAATTGTTATTTACCTATTCAAACATCCCAGATTAT
FJ011004   (1450)    AGGGAATCAAGTGGAAATTGTTATTTACCTATTCAAACATCCCAGATTAT
FJ011005   (1450)    AGGGAATCAGGTGGAAATTGTTATTTACCTATTCAAACCTCCCAGATTAT
FJ423608   (1450)    AGGGAATCAAGTGGAAATTGTTATTTGCCTATTCAAACATCCCAGATTAT
FJ705233   (1450)    AGGGAATCAAGTGGAAATTGTTATTTGCCTATTCAAACATCCCAGATTAT
GQ214376   (1450)    AGGGAATCAAGTGGAAATTGTTATTTACCTATTCAAACATCCCAGATTAT
```

Figure 15K

```
                    1501                                              1550
AF478543  (1500)    GGATAAAGATGTCCTGACTGAGTCCAATTTAGTGGTGTTGCCTACACAGA
AF478545  (1500)    GGATAAAGATGTCCTGACTGAGTCCAATTTAGTGGTGTTGCCTACACAGA
AY386316  (1500)    GGATAAAGATGTCCTTACTGAGTCCAATTTAGTGGTGTTGCCTACACAGA
ca CDV HA (1500)    GGACAAGGACGTGCTGACAGAGAGCAACCTGGTGGTGCTGCCTACCCAGA
DQ228166  (1500)    GGATAAAGATGTCCTTACTGAGTCCAATTTAGTGGTATTGCCTACACAGA
DQ494317  (1500)    GGATAAAGATGTCCTGACTGAGTCCAATTTAGTGGTGTTGCCTACACAGA
DQ494318  (1500)    GGATAAAGATGTCCTGACTGAGTCCAATTTAGTGGTGTTGCCTACACAGA
DQ889177  (1500)    GGATAAAGATGTCCTTACTGAGTCCAATTTAGTGGTGTTGCCTACACAGA
DQ889187  (1500)    GGATAAAGATGTCCTTACTGAGTCCAATTTGGTGGTGTTGCCTACACAGA
EU325730  (1500)    GGATAAAGATGTCCTTACTGAGTCCAATTTAGTGGTGTTACCTACACAGA
EU716337  (1500)    GGATAAAGATGTCCTTACTGAGTCCAATTTAGTGGTGTTGCCTACACAGA
FJ011004  (1500)    GGATAAAGATGTCCTTACTGAGTCCAATTTAGTGGTGTTGCCTACACAGA
FJ011005  (1500)    GGATAAAGATGTCCTTGCTGAGTCCAATTTAGTGGTGTTGCCTACACAGA
FJ423608  (1500)    GGATAAAGATGTCCTTACTGAGTCCAATTTAGTGGTGTTACCTACACAGA
FJ705233  (1500)    GGATAAAGATGTCCTTACTGAGTCCAATTTAGTAGTGTTACCTACACAGA
GQ214376  (1500)    GGATAAAGATGTCCTTACTGAGTCCAATTTAGTGGTGTTGCCTACACAGA

                    1551                                              1600
AF478543  (1550)    ATTTTAGATATGTCATAGCAACATATGATATATCTCGGGGCGATCATGCA
AF478545  (1550)    ATTTTAGATATGTCATAGCAACATATGATATATCTCGGGGCGATCATGCA
AY386316  (1550)    ATTTTAGATATGTCATAGCAACATATGATATATCCCGGGGCGATCATGCA
ca CDV HA (1550)    ACTTCCGGTACGTGATCGCCACCTACGACATCAGCAGAGGCGATCACGCC
DQ228166  (1550)    ATTTTAGATATGTCATAGCAACATATGATATATCCCGGAACGATCATGCG
DQ494317  (1550)    ATTTTAGATATGTCATAGCAACATATGATATATCTCGGGGCGATCATGCA
DQ494318  (1550)    ATTTTAGATATGTCATAGCAACATATGATATATCTCGGGGCGATCATGCC
DQ889177  (1550)    ATTTTAGATATGTCATAGCAACATATGATATATCCCGGGGCGATCATGCA
DQ889187  (1550)    ATTTTAGATATGTCATAGCAACATATGATATATCCCGGGATGATCATGCG
EU325730  (1550)    ATTTTAGATATGTCATAGCAACATATGATATATCCCGGGGCGATCATGCA
EU716337  (1550)    ATTTTAGATATGTCATAGCAACATATGATATATCCCGGGGCGATCATGCG
FJ011004  (1550)    ATTTTAGATATGTCATAGCAACATATGATATATCCCGGGGCGATCATGCA
FJ011005  (1550)    ATTTTAGATATGTCATAGCAACATATGATATATCCCGGGACGATCATGCG
FJ423608  (1550)    ATTTTAGATATGTCATAGCAACATATGATATATCCCGGGGCGATCATGCA
FJ705233  (1550)    ATTTTAGGTATGTCATAGCAACATATGATATATCCCGGGGCGATCATGCA
GQ214376  (1550)    ATTTTAGATATGTCATAGCAACATATGATATATCCCGGGGTGATCATGCA

                    1601                                              1650
AF478543  (1600)    ATTGTTTATGATGTTTATGACCCAATCCGGACGATTTCTTATACGCACCC
AF478545  (1600)    ATTGTTTATTATGTTTATGACCCAATCCGGACGATTTCTTATACGTACCC
AY386316  (1600)    ATTGTTTATTATGTTTATGACCCAATCCGGACGATTTCTTATACGCACCC
ca CDV HA (1600)    ATCGTGTACTACGTGTACGACCCCATCCGGACCATCAGCTACACATACCC
DQ228166  (1600)    ATTGTTTATTATGTTTATGACCCAATCCGGACTATTTCTTATACGCACCC
DQ494317  (1600)    ATTGTTTATTATGTTTATGACCCAATCCGGACGATTTCTTATACGTACCC
DQ494318  (1600)    ATTGTTTATTATGTTTATGACCCAATCCGGACGATTTCTTATACGTACCC
DQ889177  (1600)    ATTGTTTATTATGTTTATGACCCAATCCGGACGATATCCTATACGTACCC
DQ889187  (1600)    ATTGTTTATTATGTTTATGACCCAATCCGGACGATTTCTTATACGTACCC
EU325730  (1600)    ATTGTTTATTATGTTTATGACCCTATCCGGACGATTTCTTATACATACCC
EU716337  (1600)    ATTGTTTATTATGTTTATGACCCAATCCGGGCGATTTCTTATACGTACCC
FJ011004  (1600)    ATTGTTTATTATGTTTATGACCCAATCCGGACGATTTCTTATACTTACCC
FJ011005  (1600)    ATTGTTTATTATGTTTATGATCCAATCCGGACGATTTCTTATACGTACCC
FJ423608  (1600)    ATTGTTTATTATGTTTATGACCCTATCCGGACGATTTCTTATACATACCC
FJ705233  (1600)    ATTGTTTATTATGTTTATGACCCAATCCGGACGATTTCTTATACATACCC
GQ214376  (1600)    ATTGTTTATTATGTTTATGACCCAATCCGGACGATTTCTTATACGTACCC
```

Figure 15L

```
                   1651                                              1700
AF478543   (1650)  ATTTAGACTAACTACCAAGGGTAGACCTGATTTCCTAAGAATTGAATGTT
AF478545   (1650)  ATTTAGACTAACTACCAAGGGTAGACCTGATTTCCTAAGAATTGAATGTT
AY386316   (1650)  ATTTAGACTAACCACCAAGGGTAGACCTGATTTCCTAAGGATTGAATGTT
ca CDV HA  (1650)  CTTCCGGCTGACCACCAAGGGCAGACCCGACTTCCTGCGGATCGAGTGCT
DQ228166   (1650)  ATTTAGACTAACTACTAAGGGTAGACCTGATTTCCTAAGGATTGAATGTT
DQ494317   (1650)  ATTTAGACTAACTACCAAGGGTAGACCTGATTTCCTAAGAATTGAATGTT
DQ494318   (1650)  ATTTAGACTGACTACCAAGGGTAGACCTGATTTCCTAAGAATTGAATGTT
DQ889177   (1650)  ATTTAGACTAACTACCAAGGGTAGACCTGAATTCCTAAGGATTGAATGTT
DQ889187   (1650)  ATTTAGACTAACTACCAAGGGTAGACCTGATTTCCTAAGGATTGAATGTT
EU325730   (1650)  ATTTAGACTAACTACCAAGGGTAGACCTGATTTCCTAAGGATTGAATGTT
EU716337   (1650)  ATTTAGACTAACTACCAAGGGTAGACCTGATTTCCTAAGGATTGAATGTT
FJ011004   (1650)  ATTTAGACTAACTACCAAGGGTAGACCTGTTTCCCTAAGGATTGAATGTT
FJ011005   (1650)  ATTTAGACTAACTACCAAGGGTAGACCTGATTTCCTAAGAATTGAATGTT
FJ423608   (1650)  ATTTAGACTAACTACCAAAGGTAGACCTGATTTCCTAAGGATTGAATGTT
FJ705233   (1650)  ATTTAGACTAACTACCAAGGGTAGACCTGATTTCCTAAGGATTGAATGTT
GQ214376   (1650)  ATTTAGACTAACTACCAAGGGTAGACCTGATTTCCTAAGGATTGAATGTT

                   1701                                              1750
AF478543   (1700)  TTGTGTGGGATGACGATTTGTGGTGTCACCAATTTTACCGATTTGAGGCT
AF478545   (1700)  TTGTGTGGGATGACGATTTGTGGTGTCACCAATTTTACCGATTTGAGGCT
AY386316   (1700)  TTGTGTGGGATGACGATTTGTGGTGTCACCAATTTTACCGATTTGAGGCT
ca CDV HA  (1700)  TTGTGTGGGACGACGACCTGTGGTGCCACCAGTTCTACAGATTCGAGGCC
DQ228166   (1700)  TTGTGTGGGATGATGATTTGTGGTGTCACCAATTTTACCGGTTCGAGGCT
DQ494317   (1700)  TTGTGTGGGATGACGATATGTGGTGTCACCAATTTTACCGATTTGAGGCT
DQ494318   (1700)  TTGTGTGGGATGACGATTTGTGGTGTCACCAATTTTACCGATTTGAGGCT
DQ889177   (1700)  TTGTGTGGGATGACGATTTGTGGTGTCACCAATTTTACCGATTTGAGGCT
DQ889187   (1700)  TTGTGTGGGATTACGATTTGTGGTGTCACCAATTTTACCGATTCGAGGCT
EU325730   (1700)  TTGTGTGGGATGACGATTTGTGGTGTCATCAATTTTACCGATTCGAGGCT
EU716337   (1700)  TTGTGTGGGATGACGATTTGTGGTGTCACCAATTTTACCGATTCGAGGCT
FJ011004   (1700)  TTGTGTGGGATGACGATTTGTGGTGTCACCAATTTTACCAATTTGAGGCA
FJ011005   (1700)  TTGTATGGGATGACGATTTGTGGTGTCATCAATTTTACCGATTCGAGGCT
FJ423608   (1700)  TTGTGTGGGATGACGATTTGTGGTGTCATCAATTTTACCGATTCGAGGCT
FJ705233   (1700)  TTGTGTGGGATGACGATTTGTGGTGTCATCAATTTTACCGATTCGAGGCT
GQ214376   (1700)  TTGTGTGGGATGACGATTTGTGGTGTCACCAATTTTATCGATTTGAGGCT

                   1751                                              1800
AF478543   (1750)  GACATCACCAACTCTACAACCAGTGTTGAGAATTTAGTCCGTATAAGATT
AF478545   (1750)  GACATCACCAACTCTACAACCAGTGTTGAGAATTTAGTCCGTATAAGATT
AY386316   (1750)  GACATCACCAACTCTACAACCAGTGTTGAGAATTTAGTCCGTATAAGATT
ca CDV HA  (1750)  GACATCACCAATAGCACCACCTCCGTGGAGAACCTTGTGAGGATCCGGTT
DQ228166   (1750)  GACATCACCAACTCTGCAACCAGTGTTGAGAATTTGGTCCGTATAAGATT
DQ494317   (1750)  GACATCACCAACTCTACAACCAGTGTTGAGAATTTAGTCCGTATAAGATT
DQ494318   (1750)  GACATCACCAACTCTACAACCAGTGTTGAGAATTTAGTCCGTATAAGATT
DQ889177   (1750)  GACATCACCAACTCTACAATCAGTGTTGAGAATTTAGTCCATATAAGATT
DQ889187   (1750)  GACATCACCAACTCTACAACCAGTGTTGAGAATTTAGTCCGTATAAGATT
EU325730   (1750)  AACATCACTAACTCTACAACCAGTGTTGAGAATTTAGTCCGTATAAGATT
EU716337   (1750)  GACAGCACCAACTCTACAACCAGTGTTGAGAATTTAGTCCGTATAAGATT
FJ011004   (1750)  GACATCACCAACTCTACCACCAGTGTTGAGAATTTAGTCCGTATAAGATT
FJ011005   (1750)  GACATCACTAACTCTACAACCAGTGTTGAGAATTTAGTCCGTATAAGATT
FJ423608   (1750)  AACATCACTAACTCTACAACCAGTGTTGAGAATTTAGTCCGTATAAGATT
FJ705233   (1750)  AACATTACTAACTCTACAACCAGTGTTGAGAATTTAGTCCGTATAAGATT
GQ214376   (1750)  GACATCACCAACTCTACAACCAGTGTTGAGAATTTAGTCTGTATAAGATT
```

Figure 15M

```
                       1801                    1825
AF478543   (1800)      CTCATGTGACCGTTCAAAACCTTGA
AF478545   (1800)      CTCATGTGACCGTTCAAAACCTTGA
AY386316   (1800)      CTCATGTAACCGTTCAAAACCTTGA
ca CDV HA  (1800)      CAGCTGCGACAGAAGCAAGCCC---
DQ228166   (1800)      CTCATGTAACCGTTCAAAACCTTGA
DQ494317   (1800)      CTCATGTAACCGTTCAAAACCTTGA
DQ494318   (1800)      CTCATGTAATCGTTCAAAACCTTGA
DQ889177   (1800)      CTCATGTAACCGTTCAAAACCTTGA
DQ889187   (1800)      CTCATGTAACCGTTCAAAACCTTGA
EU325730   (1800)      CTCATGTAACCGTTCAAAACCTTGA
EU716337   (1800)      CTCATGTAATCGTTCAAAACCTTGA
FJ011004   (1800)      CTCATGTAACCGTTCAAAACCT---
FJ011005   (1800)      CTCATGTAACCGTTCAAAACCT---
FJ423608   (1800)      CTCATGTAACCGTTCAAAACCTTGA
FJ705233   (1800)      CTCATGTAACCGTTCAAAACCTTGA
GQ214376   (1800)      CTCATGTAACCGTTCAAAACCTTGA
```

AF478543:SEQ ID NO:36; AF478545:SEQ ID NO:35; AY386316:SEQ ID NO:38; ca CDV HA:SEQ ID NO:1; DQ228166:SEQ ID NO:46; DQ494317:SEQ ID NO:39; DQ494318:SEQ ID NO:37; DQ889177:SEQ ID NO:41; DQ889187:SEQ ID NO:47; EU325730:SEQ ID NO:49; EU716337:SEQ ID NO:42; FJ011004:SEQ ID NO:43; FJ011005:SEQ ID NO:44; FJ423608:SEQ ID NO:48; FJ705233:SEQ ID NO:45; GQ214376:SEQ ID NO:40.

Figure 15N

Sequence Identity Percentage of CDV HA DNA

| SEQ ID NO: | 1 | 35 | 36 | 37 | 38 | 39 | 40 | 41 | 42 | 43 | 44 | 45 | 46 | 47 | 48 | 49 |
|---|---|---|---|---|---|---|---|---|---|---|---|---|---|---|---|---|
| 1 | | 73 | 73 | 72 | 73 | 72 | 72 | 72 | 72 | 72 | 72 | 71 | 71 | 71 | 71 | 71 |
| 35 | | | 99 | 99 | 99 | 99 | 99 | 98 | 97 | 98 | 95 | 95 | 96 | 96 | 95 | 95 |
| 36 | | | | 99 | 99 | 99 | 98 | 98 | 97 | 98 | 95 | 95 | 96 | 96 | 95 | 95 |
| 37 | | | | | 98 | 99 | 98 | 98 | 97 | 97 | 95 | 95 | 95 | 95 | 94 | 95 |
| 38 | | | | | | 99 | 98 | 98 | 97 | 98 | 95 | 95 | 96 | 96 | 95 | 95 |
| 39 | | | | | | | 98 | 98 | 97 | 98 | 95 | 95 | 95 | 96 | 95 | 95 |
| 40 | | | | | | | | 98 | 97 | 98 | 95 | 95 | 96 | 96 | 95 | 95 |
| 41 | | | | | | | | | 96 | 97 | 95 | 94 | 95 | 95 | 94 | 95 |
| 42 | | | | | | | | | | 96 | 95 | 95 | 96 | 96 | 95 | 95 |
| 43 | | | | | | | | | | | 95 | 95 | 95 | 95 | 94 | 95 |
| 44 | | | | | | | | | | | | 94 | 95 | 95 | 94 | 94 |
| 45 | | | | | | | | | | | | | 94 | 94 | 98 | 98 |
| 46 | | | | | | | | | | | | | | 96 | 94 | 94 |
| 47 | | | | | | | | | | | | | | | 94 | 94 |
| 48 | | | | | | | | | | | | | | | | 99 |
| 49 | | | | | | | | | | | | | | | | |

Figure 16

Monitoring of Cellular Immune Response

| Group | Dog ID | D13 | D42 | D70 |
|---|---|---|---|---|
| A vCP2392 (CDV HA – GM CSF) | 1 | 6 | 0 | 0 |
| | 2 | 0 | 0 | 2 |
| | 3 | ND | 0 | 0 |
| | 4 | 0 | 1 | 0 |
| | 5 | 3 | 18 | 3 |
| | 6 | 2 | 45 | 0 |
| B vCP2263 (CDV HA) | 7 | 0 | 0 | 0 |
| | 8 | 1 | 29 | 1 |
| | 9 | ND | ND | 4 |
| | 10 | 4 | ND | 0 |
| | 11 | ND | ND | 2 |
| | 12 | 0 | 2 | 3 |
| C unvaccinated | 13 | 1 | 0 | 0 |
| | 14 | ND | 0 | 0 |
| | 15 | ND | ND | 0 |
| | 16 | 0 | ND | 0 |
| | 17 | 1 | 0 | 0 |
| | 18 | ND | ND | 0 |

Units: number of CDV HA specific IFNγ-spot forming cell/500 x $10^3$ PBMCs.
ND: not determined Figure 17
A. CPV2 ELISA serology kinetics
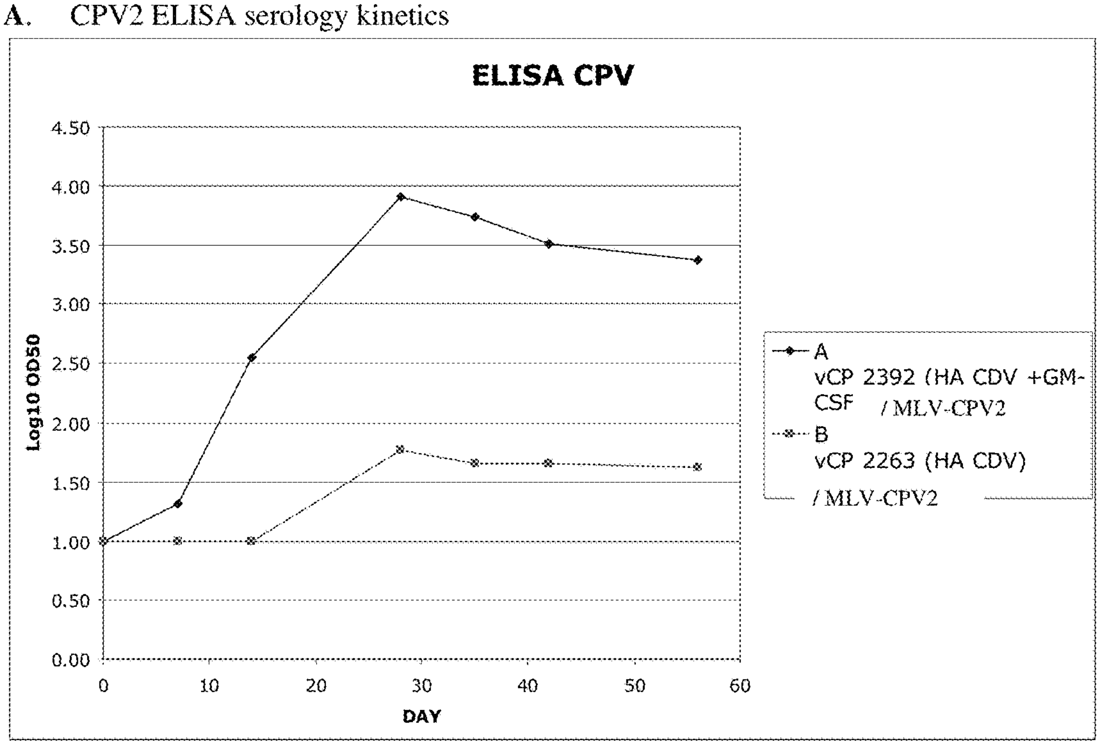
B. Box and whisker plot showing CPV2 serology on D28
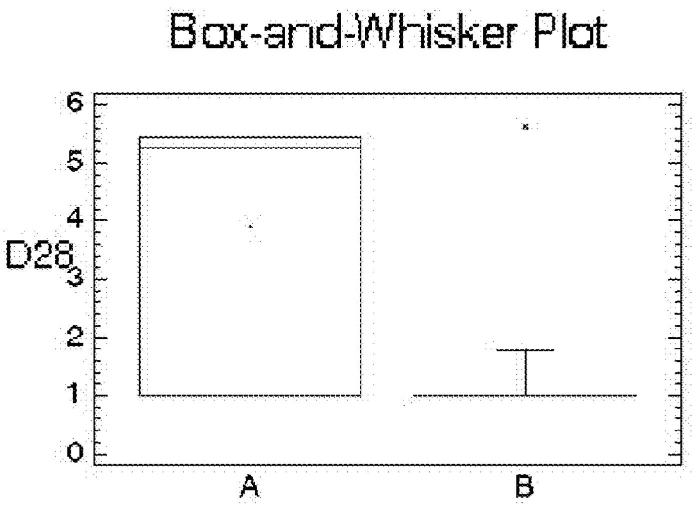

CDV SN antibodies using a homologous SN test

SN CDV on VERO SLAM

(Graph: SERA TITER Log10 SN50/ml vs DAYS: D0, D7, D14, D28, D35, D42, D56; V1 arrow near D0, V2 arrow near D28)

- ♦ vCP2392 (HA CDV + GM-CSF) / MLV-CPV2
- ■ vCP2263 (HA CDV) / MLV-CPV2

CDV SN antibodies using a heterologous SN test

SEQUENCE LISTING

```
<160> NUMBER OF SEQ ID NOS: 51

<210> SEQ ID NO 1
<211> LENGTH: 1821
<212> TYPE: DNA
<213> ORGANISM: artificial sequence
<220> FEATURE:
<223> OTHER INFORMATION: codon-optimized CDV HA gene

<400> SEQUENCE: 1

atgctgagct accaggacaa agtgggcgcc ttctacaagg acaacgccag ggccaatagc     60
agcaagctga gcctggtgac cgaggagcag ggcggcagga gacccccccta cctgctgttc    120
gtgctgctga tccttcttgt gggcatcatg accctgctgg ccatcaccgg agtgagattc    180
caccaggtgt ccacctccaa catggagttc agccggctgc tgaaagagga catggagaag    240
agcgaggccg tgcaccacca ggtgatcgat gtgctgaccc ccctgttcaa gatcatcggc    300
gacgaagtgg gcctgagact gccccagaag ctgaacgaga tcaagcagtt catcctgcag    360
aaaaccaact tcttcaaccc caaccgggag ttcgacttca gagacctgca ctggtgcatc    420
aacccccccca gcaagatcaa agtgaacttc accaactact gcgacaccat cggcatcagg    480
aagagcatcg ccagcgccgt gaatcccatc ctgctgagcg ccctgagcgg cggcagaggc    540
gacatcttcc ccccctacag atgcagcggc gccaccacct ctgtgggcag agtgttccct    600
ctgagcgtgt ccctgagcat gagcctgatc agcaagacca gcgagatcac caacatgctg    660
accgccatca gcgacggcgt gtacggcaag acctatctgc tggtgcccga ctacatcgag    720
ggcgagttcg acacccagaa gatccgcgtg ttcgagatcg gcttcatcaa gcggtggctg    780
aacaacatgc ccctgctgca gaccaccaac tacatggtgc tgcccgagaa cagcaaggcc    840
aaagtgtgca ccatcgctgt gggcgagctg accctggcca gcctgtgcgt ggacgagagc    900
accgtgctgc tgtaccacga cagcaacggc agccaggacg gcatcctggt ggtgaccctg    960
ggcatcttcg gcgccacccc tatggaccag gtggaggaag tgatccccgt ggcccacccc   1020
agcgtggaga agatccacat caccaaccac cggggcttta tcaaggacag catcgccacc   1080
tggatggtgc ccgccctggt gtctgagaag caggaggagc agaagaactg cctggagagc   1140
gcctgccaga gaaagaccta ccccatgtgc aaccagacca gctgggagcc ctttggcggc   1200
ggacagctgc ccagctacgg cagactgacc ctgagcctgg accctagcat cgacctgcag   1260
ctgaacatca gcttcaccta cggccccgtg atcctgaacg gcgacggcat ggattactac   1320
ggcagcagcc tgagcgacag cggctggctg accatccctc ccaagaacgg cacagtgctg   1380
ggcctgatca acaaggcctc caggggcgac cagttcaccg tgatccctca cgtgctgacc   1440
ttcgcccccca gagagagcag cggcaactgc tacctgccta tccagacctc ccagatcatg   1500
gacaaggacg tgctgacaga gagcaacctg gtggtgctgc ctacccagaa cttccggtac   1560
```

-continued

```
gtgatcgcca cctacgacat cagcagaggc gatcacgcca tcgtgtacta cgtgtacgac   1620

cccatccgga ccatcagcta cacatacccc ttccggctga ccaccaaggg cagacccgac   1680

ttcctgcgga tcgagtgctt tgtgtgggac gacgacctgt ggtgccacca gttctacaga   1740

ttcgaggccg acatcaccaa tagcaccacc tccgtggaga accttgtgag gatccggttc   1800

agctgcgaca gaagcaagcc c                                               1821


<210> SEQ ID NO 2
<211> LENGTH: 607
<212> TYPE: PRT
<213> ORGANISM: artificial sequence
<220> FEATURE:
<223> OTHER INFORMATION: CDV HA protein encoded by codon-optimized gene
      (SEQ ID NO:1)

<400> SEQUENCE: 2

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
        35                  40                  45

Ile Met Thr Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Ile Gly Ile Arg
145                 150                 155                 160

Lys Ser Ile Ala Ser Ala Val Asn Pro Ile Leu Leu Ser Ala Leu Ser
                165                 170                 175

Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Lys Thr Ser Glu Ile Thr Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Glu Phe Asp Thr Gln Lys Ile Arg Val Phe Glu Ile Gly Phe Ile
                245                 250                 255

Lys Arg Trp Leu Asn Asn Met Pro Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300
```

-continued

```
Tyr His Asp Ser Asn Gly Ser Gln Asp Gly Ile Leu Val Val Thr Leu
305                 310                 315                 320

Gly Ile Phe Gly Ala Thr Pro Met Asp Gln Val Glu Glu Val Ile Pro
                325                 330                 335

Val Ala His Pro Ser Val Glu Lys Ile His Ile Thr Asn His Arg Gly
            340                 345                 350

Phe Ile Lys Asp Ser Ile Ala Thr Trp Met Val Pro Ala Leu Val Ser
        355                 360                 365

Glu Lys Gln Glu Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Leu Thr Leu Ser Leu Asp Pro Ser
                405                 410                 415

Ile Asp Leu Gln Leu Asn Ile Ser Phe Thr Tyr Gly Pro Val Ile Leu
            420                 425                 430

Asn Gly Asp Gly Met Asp Tyr Tyr Gly Ser Ser Leu Ser Asp Ser Gly
        435                 440                 445

Trp Leu Thr Ile Pro Pro Lys Asn Gly Thr Val Leu Gly Leu Ile Asn
    450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Tyr Val Tyr Asp Pro Ile Arg Thr
    530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Asp Leu Trp Cys His
                565                 570                 575

Gln Phe Tyr Arg Phe Glu Ala Asp Ile Thr Asn Ser Thr Thr Ser Val
            580                 585                 590

Glu Asn Leu Val Arg Ile Arg Phe Ser Cys Asp Arg Ser Lys Pro
        595                 600                 605


<210> SEQ ID NO 3
<211> LENGTH: 435
<212> TYPE: DNA
<213> ORGANISM: artificial sequence
<220> FEATURE:
<223> OTHER INFORMATION: codon-optimized canine GM-CSF gene

<400> SEQUENCE: 3

atgtggctgc agaacctgct gttcctgggc accgtggtgt gcagcatcag cgcccccacc      60

agatccccca ccctggtgac ccggcccagc cagcacgtgg acgccatcca ggaagccctg     120

agcctgctga acaacagcaa cgacgtgacc gccgtgatga acaaggccgt gaaggtggtg     180

tccgaggtgt tcgaccccga gggcccccacc tgcctggaaa cccggctgca gctgtacaaa     240

gagggcctgc agggcagcct gaccagcctg aagaaccccc tgaccatgat ggccaaccac     300

tacaagcagc actgcccccc cacccccgag agcccttgcg ccacccagaa catcaacttc     360
```

```
aagagcttca aagagaacct gaaggacttc ctgttcaaca tccccttcga ctgctggaag    420

cccgtgaaga agtga                                                      435


<210> SEQ ID NO 4
<211> LENGTH: 144
<212> TYPE: PRT
<213> ORGANISM: artificial sequence
<220> FEATURE:
<223> OTHER INFORMATION: canine GM-CSF protein encoded by codon-
      optimized gene (SEQ ID NO:3)

<400> SEQUENCE: 4

Met Trp Leu Gln Asn Leu Leu Phe Leu Gly Thr Val Val Cys Ser Ile
1               5                   10                  15

Ser Ala Pro Thr Arg Ser Pro Thr Leu Val Thr Arg Pro Ser Gln His
            20                  25                  30

Val Asp Ala Ile Gln Glu Ala Leu Ser Leu Leu Asn Asn Ser Asn Asp
        35                  40                  45

Val Thr Ala Val Met Asn Lys Ala Val Lys Val Val Ser Glu Val Phe
    50                  55                  60

Asp Pro Glu Gly Pro Thr Cys Leu Glu Thr Arg Leu Gln Leu Tyr Lys
65                  70                  75                  80

Glu Gly Leu Gln Gly Ser Leu Thr Ser Leu Lys Asn Pro Leu Thr Met
                85                  90                  95

Met Ala Asn His Tyr Lys Gln His Cys Pro Pro Thr Pro Glu Ser Pro
            100                 105                 110

Cys Ala Thr Gln Asn Ile Asn Phe Lys Ser Phe Lys Glu Asn Leu Lys
        115                 120                 125

Asp Phe Leu Phe Asn Ile Pro Phe Asp Cys Trp Lys Pro Val Lys Lys
    130                 135                 140


<210> SEQ ID NO 5
<211> LENGTH: 604
<212> TYPE: PRT
<213> ORGANISM: artificial sequence
<220> FEATURE:
<223> OTHER INFORMATION: CDV HA protein from vCP258

<400> SEQUENCE: 5

Met Leu Pro Tyr Gln Asp Lys Val Gly Ala Phe Tyr Lys Asp Asn Ala
1               5                   10                  15

Arg Ala Asn Ser Thr Lys Leu Ser Leu Val Thr Glu Gly His Gly Gly
            20                  25                  30

Arg Arg Pro Pro Tyr Leu Leu Phe Val Leu Leu Ile Leu Leu Val Gly
        35                  40                  45

Ile Leu Ala Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Ile Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140
```

-continued

```
Thr Val Lys Val Asn Phe Thr Asn Tyr Cys Glu Ser Ile Gly Ile Arg
145                 150                 155                 160

Lys Ala Ile Ala Ser Ala Ala Asn Pro Ile Leu Leu Ser Ala Leu Ser
                165                 170                 175

Gly Gly Arg Gly Asp Ile Phe Pro Pro His Arg Cys Ser Gly Ala Thr
            180                 185                 190

Thr Ser Val Gly Lys Val Phe Pro Leu Ser Val Ser Leu Ser Met Ser
        195                 200                 205

Leu Ile Ser Arg Thr Ser Glu Val Ile Asn Met Leu Thr Ala Ile Ser
    210                 215                 220

Asp Gly Val Tyr Gly Lys Thr Tyr Leu Leu Val Pro Asp Asp Ile Glu
225                 230                 235                 240

Arg Glu Phe Asp Thr Arg Glu Ile Arg Val Phe Glu Ile Gly Phe Ile
                245                 250                 255

Lys Arg Trp Leu Asn Asp Met Pro Leu Leu Gln Thr Thr Asn Tyr Met
            260                 265                 270

Val Leu Pro Lys Asn Ser Lys Ala Lys Val Cys Thr Ile Ala Val Gly
        275                 280                 285

Glu Leu Thr Leu Ala Ser Leu Cys Val Glu Glu Ser Thr Val Leu Leu
    290                 295                 300

Tyr His Asp Ser Ser Gly Ser Gln Asp Gly Ile Leu Val Val Thr Leu
305                 310                 315                 320

Gly Ile Phe Trp Ala Thr Pro Met Asp His Ile Glu Glu Val Ile Pro
                325                 330                 335

Val Ala His Pro Ser Met Lys Lys Ile His Ile Thr Asn His Arg Gly
            340                 345                 350

Phe Ile Lys Asp Ser Ile Ala Thr Trp Met Val Pro Ala Leu Ala Ser
        355                 360                 365

Glu Lys Gln Glu Glu Gln Lys Gly Cys Leu Glu Ser Ala Cys Gln Arg
    370                 375                 380

Lys Thr Tyr Pro Met Cys Asn Gln Ala Ser Trp Glu Pro Phe Gly Gly
385                 390                 395                 400

Arg Gln Leu Pro Ser Tyr Gly Arg Leu Thr Leu Pro Leu Asp Ala Ser
                405                 410                 415

Val Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Asn Ser Gly
        435                 440                 445

Trp Leu Thr Ile Pro Pro Lys Asp Gly Thr Ile Ser Gly Leu Ile Asn
    450                 455                 460

Lys Ala Gly Arg Gly Asp Gln Phe Thr Val Leu Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Arg Asp Arg Asp Val Leu Ile Glu Ser Asn Ile Val Val
            500                 505                 510

Leu Pro Thr Gln Ser Ile Arg Tyr Val Ile Ala Thr Tyr Asp Ile Ser
        515                 520                 525

Arg Ser Asp His Ala Ile Val Tyr Tyr Val Tyr Asp Pro Ile Arg Thr
    530                 535                 540

Ile Ser Tyr Thr His Pro Phe Arg Leu Thr Thr Lys Gly Arg Pro Asp
545                 550                 555                 560

Phe Leu Arg Ile Glu Cys Phe Val Trp Asp Asp Asn Leu Trp Cys His
```

-continued

```
                565                 570                 575

Gln Phe Tyr Arg Phe Glu Ala Asp Ile Ala Asn Ser Thr Thr Ser Val
            580                 585                 590

Glu Asn Leu Val Arg Ile Arg Phe Ser Cys Asn Arg
        595                 600


<210> SEQ ID NO 6
<211> LENGTH: 4140
<212> TYPE: DNA
<213> ORGANISM: artificial sequence
<220> FEATURE:
<223> OTHER INFORMATION: part of pCXL1557.1 containing arms and insert
<220> FEATURE:
<221> NAME/KEY: misc_feature
<222> LOCATION: (43)..(1578)
<223> OTHER INFORMATION: this is the C5L region
<220> FEATURE:
<221> NAME/KEY: promoter
<222> LOCATION: (1676)..(1799)
<223> OTHER INFORMATION: this is the H6 promoter region
<220> FEATURE:
<221> NAME/KEY: CDS
<222> LOCATION: (1800)..(3620)
<223> OTHER INFORMATION: this is the CDV-HA coding region
<220> FEATURE:
<221> NAME/KEY: misc_feature
<222> LOCATION: (3677)..(4081)
<223> OTHER INFORMATION: this is the C5R region

<400> SEQUENCE: 6

ggaaacagct atgaccatga ttacgaattg cggccgcaat tctgaatgtt aaatgttata     60

ctttggatga agctataaat atgcattgga aaaataatcc atttaaagaa aggattcaaa    120

tactacaaaa cctaagcgat aatatgttaa ctaagcttat tcttaacgac gctttaaata    180

tacacaaata aacataattt ttgtataacc taacaaataa ctaaaacata aaaataataa    240

aaggaaatgt aatatcgtaa ttattttact caggaatggg gttaaatatt tatatcacgt    300

gtatatctat actgttatcg tatactcttt acaattacta ttacgaatat gcaagagata    360

ataagattac gtatttaaga gaatcttgtc atgataattg ggtacgacat agtgataaat    420

gctatttcgc atcgttacat aaagtcagtt ggaaagatgg atttgacaga tgtaacttaa    480

taggtgcaaa aatgttaaat aacagcattc tatcggaaga taggatacca gttatattat    540

acaaaaatca ctggttggat aaaacagatt ctgcaatatt cgtaaaagat gaagattact    600

gcgaatttgt aaactatgac aataaaaagc catttatctc aacgacatcg tgtaattctt    660

ccatgtttta tgtatgtgtt tcagatatta tgagattact ataaactttt tgtatactta    720

tattccgtaa actatattaa tcatgaagaa aatgaaaaag tatagaagct gttcacgagc    780

ggttgttgaa aacaacaaaa ttatacattc aagatggctt acatatacgt ctgtgaggct    840

atcatggata atgacaatgc atctctaaat aggtttttgg acaatggatt cgaccctaac    900

acggaatatg gtactctaca atctcctctt gaaatggctg taatgttcaa gaataccgag    960

gctataaaaa tcttgatgag gtatggagct aaacctgtag ttactgaatg cacaacttct   1020

tgtctgcatg atgcggtgtt gagagacgac tacaaaatag tgaaagatct gttgaagaat   1080

aactatgtaa acaatgttct ttacagcgga ggctttactc ctttgtgttt ggcagcttac   1140

cttaacaaag ttaatttggt taaacttcta ttggctcatt cggcggatgt agatatttca   1200

aacacggatc ggttaactcc tctacatata gccgtatcaa ataaaaattt aacaatggtt   1260

aaacttctat tgaacaaagg tgctgatact gacttgctgg ataacatggg acgtactcct   1320

ttaatgatcg ctgtacaatc tggaaatatt gaaatatgta gcacactact taaaaaaaat   1380
```

-continued

```
aaaatgtcca gaactgggaa aaattgatct tgccagctgt aattcatggt agaaaagaag   1440
tgctcaggct acttttcaac aaaggagcag atgtaaacta catctttgaa agaaatggaa   1500
aatcatatac tgttttggaa ttgattaaag aaagttactc tgagacacaa aagaggtagc   1560
tgaagtggta ctctcaaagg tacgtgacta attagctata aaaaggatcc gggttaatta   1620
attagtcatc aggcagggcg agaacgagac tatctgctcg ttaattaatt agagcttctt   1680
tattctatac ttaaaaagtg aaaataaata caaaggttct tgagggttgt gttaaattga   1740
aagcgagaaa taatcataaa ttatttcatt atcgcgatat ccgttaagtt tgtatcgtaa   1800
tgctgagcta ccaggacaaa gtgggcgcct tctacaagga caacgccagg gccaatagca   1860
gcaagctgag cctggtgacc gaggagcagg gcggcaggag accccccctac ctgctgttcg   1920
tgctgctgat ccttcttgtg ggcatcatga ccctgctggc catcaccgga gtgagattcc   1980
accaggtgtc cacctccaac atggagttca gccggctgct gaaagaggac atggagaaga   2040
gcgaggccgt gcaccaccag gtgatcgatg tgctgacccc cctgttcaag atcatcggcg   2100
acgaagtggg cctgagactg ccccagaagc tgaacgagat caagcagttc atcctgcaga   2160
aaaccaactt cttcaacccc aaccgggagt tcgacttcag agacctgcac tggtgcatca   2220
acccccccag caagatcaaa gtgaacttca ccaactactg cgacaccatc ggcatcagga   2280
agagcatcgc cagcgccgtg aatcccatcc tgctgagcgc cctgagcggc ggcagaggcg   2340
acatcttccc cccctacaga tgcagcggcg ccaccacctc tgtgggcaga gtgttccctc   2400
tgagcgtgtc cctgagcatg agcctgatca gcaagaccag cgagatcacc aacatgctga   2460
ccgccatcag cgacggcgtg tacggcaaga cctatctgct ggtgcccgac tacatcgagg   2520
gcgagttcga cacccagaag atccgcgtgt tcgagatcgg cttcatcaag cggtggctga   2580
acaacatgcc cctgctgcag accaccaact acatggtgct gcccgagaac agcaaggcca   2640
aagtgtgcac catcgctgtg ggcgagctga ccctggccag cctgtgcgtg gacgagagca   2700
ccgtgctgct gtaccacgac agcaacggca gccaggacgg catcctggtg gtgaccctgg   2760
gcatcttcgg cgccacccct atggaccagg tggaggaagt gatccccgtg gcccacccca   2820
gcgtggagaa gatccacatc accaaccacc ggggctttat caaggacagc atcgccacct   2880
ggatggtgcc cgccctggtg tctgagaagc aggaggagca gaagaactgc ctggagagcg   2940
cctgccagag aaagacctac cccatgtgca accagaccag ctgggagccc tttggcggcg   3000
gacagctgcc cagctacggc agactgaccc tgagcctgga ccctagcatc gacctgcagc   3060
tgaacatcag cttcacctac ggccccgtga tcctgaacgg cgacggcatg gattactacg   3120
gcagcagcct gagcgacagc ggctggctga ccatccctcc caagaacggc acagtgctgg   3180
gcctgatcaa caaggcctcc aggggcgacc agttcaccgt gatccctcac gtgctgacct   3240
tcgcccccag agagagcagc ggcaactgct acctgcctat ccagacctcc cagatcatgg   3300
acaaggacgt gctgacagag agcaacctgg tggtgctgcc tacccagaac ttccggtacg   3360
tgatcgccac ctacgacatc agcagaggcg atcacgccat cgtgtactac gtgtacgacc   3420
ccatccggac catcagctac acatacccct tccggctgac caccaagggc agacccgact   3480
tcctgcggat cgagtgcttt gtgtgggacg acgacctgtg gtgccaccag ttctacagat   3540
tcgaggccga catcaccaat agcaccacct ccgtggagaa ccttgtgagg atccggttca   3600
gctgcgacag aagcaagccc tgatagctcg agtctagaat cgatcccggg tttttatgac   3660
tagttaatca cggccgctta taaagatcta aaatgcataa tttctaaata atgaaaaaaa   3720
```

-continued

```
gtacatcatg agcaacgcgt tagtatattt tacaatggag attaacgctc tataccgttc   3780

tatgtttatt gattcagatg atgttttaga aaagaaagtt attgaatatg aaaactttaa   3840

tgaagatgaa gatgacgacg atgattattg ttgtaaatct gttttagatg aagaagatga   3900

cgcgctaaag tatactatgg ttacaaagta taagtctata ctactaatgg cgacttgtgc   3960

aagaaggtat agtatagtga aaatgttgtt agattatgat tatgaaaaac caaataaatc   4020

agatccatat ctaaaggtat ctcctttgca cataatttca tctattccta gtttagaata   4080

cctgcagcca agcttggcac tggccgtcgt tttacaacgt cgtgactggg aaaaccctgg   4140
```

```
<210> SEQ ID NO 7
<211> LENGTH: 6700
<212> TYPE: DNA
<213> ORGANISM: artificial sequence
<220> FEATURE:
<223> OTHER INFORMATION: pCXL1557.1 plasmid entire sequence

<400> SEQUENCE: 7

acatatagcc gtatcaaata aaaatttaac aatggttaaa cttctattga acaaaggtgc     60

tgatactgac ttgctggata acatgggacg tactccttta atgatcgctg tacaatctgg    120

aaatattgaa atatgtagca cactacttaa aaaaaataaa atgtccagaa ctgggaaaaa    180

ttgatcttgc cagctgtaat tcatggtaga aaagaagtgc tcaggctact tttcaacaaa    240

ggagcagatg taaactacat ctttgaaaga aatggaaaat catatactgt tttggaattg    300

attaaagaaa gttactctga gacacaaaag aggtagctga agtggtactc tcaaaggtac    360

gtgactaatt agctataaaa aggatccggg ttaattaatt agtcatcagg cagggcgaga    420

acgagactat ctgctcgtta attaattaga gcttctttat tctatactta aaaagtgaaa    480

ataaatacaa aggttcttga gggttgtgtt aaattgaaag cgagaaataa tcataaatta    540

tttcattatc gcgatatccg ttaagtttgt atcgtaatgc tgagctacca ggacaaagtg    600

ggcgccttct acaaggacaa cgccagggcc aatagcagca agctgagcct ggtgaccgag    660

gagcagggcg gcaggagacc cccctacctg ctgttcgtgc tgctgatcct tcttgtgggc    720

atcatgaccc tgctggccat caccggagtg agattccacc aggtgtccac ctccaacatg    780

gagttcagcc ggctgctgaa agaggacatg gagaagagcg aggccgtgca ccaccaggtg    840

atcgatgtgc tgaccccccct gttcaagatc atcggcgacg aagtgggcct gagactgccc    900

cagaagctga acgagatcaa gcagttcatc ctgcagaaaa ccaacttctt caaccccaac    960

cgggagttcg acttcagaga cctgcactgg tgcatcaacc cccccagcaa gatcaaagtg   1020

aacttcacca actactgcga caccatcggc atcaggaaga gcatcgccag cgccgtgaat   1080

cccatcctgc tgagcgccct gagcggcggc agaggcgaca tcttcccccc ctacagatgc   1140

agcggcgcca ccacctctgt gggcagagtg ttccctctga gcgtgtccct gagcatgagc   1200

ctgatcagca agaccagcga gatcaccaac atgctgaccg ccatcagcga cggcgtgtac   1260

ggcaagacct atctgctggt gcccgactac atcgagggcg agttcgacac ccagaagatc   1320

cgcgtgttcg agatcggctt catcaagcgg tggctgaaca acatgcccct gctgcagacc   1380

accaactaca tggtgctgcc cgagaacagc aaggccaaag tgtgcaccat cgctgtgggc   1440

gagctgaccc tggccagcct gtgcgtggac gagagcaccg tgctgctgta ccacgacagc   1500

aacggcagcc aggacggcat cctggtggtg accctgggca tcttcggcgc cacccctatg   1560

gaccaggtgg aggaagtgat ccccgtggcc caccccagcg tggagaagat ccacatcacc   1620

aaccaccggg gctttatcaa ggacagcatc gccacctgga tggtgcccgc cctggtgtct   1680
```

-continued

```
gagaagcagg aggagcagaa gaactgcctg gagagcgcct gccagagaaa gacctacccc   1740
atgtgcaacc agaccagctg ggagcccttt ggcggcggac agctgcccag ctacggcaga   1800
ctgaccctga gcctggaccc tagcatcgac ctgcagctga acatcagctt cacctacggc   1860
cccgtgatcc tgaacggcga cggcatggat tactacggca gcagcctgag cgacagcggc   1920
tggctgacca tccctcccaa gaacggcaca gtgctgggcc tgatcaacaa ggcctccagg   1980
ggcgaccagt tcaccgtgat ccctcacgtg ctgaccttcg cccccagaga gagcagcggc   2040
aactgctacc tgcctatcca gacctcccag atcatggaca aggacgtgct gacagagagc   2100
aacctggtgg tgctgcctac ccagaacttc cggtacgtga tcgccaccta cgacatcagc   2160
agaggcgatc acgccatcgt gtactacgtg tacgacccca tccggaccat cagctacaca   2220
tacccccttcc ggctgaccac caagggcaga cccgacttcc tgcggatcga gtgctttgtg   2280
tgggacgacg acctgtggtg ccaccagttc tacagattcg aggccgacat caccaatagc   2340
accacctccg tggagaacct tgtgaggatc cggttcagct gcgacagaag caagccctga   2400
tagctcgagt ctagaatcga tcccgggttt ttatgactag ttaatcacgg ccgcttataa   2460
agatctaaaa tgcataattt ctaaataatg aaaaaaagta catcatgagc aacgcgttag   2520
tatattttac aatggagatt aacgctctat accgttctat gtttattgat tcagatgatg   2580
ttttagaaaa gaaagttatt gaatatgaaa actttaatga agatgaagat gacgacgatg   2640
attattgttg taaatctgtt ttagatgaag aagatgacgc gctaaagtat actatggtta   2700
caaagtataa gtctatacta ctaatggcga cttgtgcaag aaggtatagt atagtgaaaa   2760
tgttgttaga ttatgattat gaaaaaccaa ataaatcaga tccatatcta aaggtatctc   2820
ctttgcacat aatttcatct attcctagtt tagaatacct gcagccaagc ttggcactgg   2880
ccgtcgtttt acaacgtcgt gactgggaaa accctggcgt tacccaactt aatcgccttg   2940
cagcacatcc ccctttcgcc agctggcgta atagcgaaga ggcccgcacc gatcgccctt   3000
cccaacagtt gcgcagcctg aatggcgaat ggcgcctgat gcggtatttt ctccttacgc   3060
atctgtgcgg tatttcacac cgcatatggt gcactctcag tacaatctgc tctgatgccg   3120
catagttaag ccagccccga cacccgccaa cacccgctga cgcgccctga cgggcttgtc   3180
tgctcccggc atccgcttac agacaagctg tgaccgtctc cgggagctgc atgtgtcaga   3240
ggttttcacc gtcatcaccg aaacgcgcga gacgaaaggg cctcgtgata cgcctatttt   3300
tataggttaa tgtcatgata ataatggttt cttagacgtc aggtggcact tttcggggaa   3360
atgtgcgcgg aacccctatt tgtttatttt tctaaataca ttcaaatatg tatccgctca   3420
tgagacaata accctgataa atgcttcaat aatattgaaa aaggaagagt atgagtattc   3480
aacatttccg tgtcgccctt attccctttt ttgcggcatt ttgccttcct gtttttgctc   3540
acccagaaac gctggtgaaa gtaaaagatg ctgaagatca gttgggtgca cgagtgggtt   3600
acatcgaact ggatctcaac agcggtaaga tccttgagag ttttcgcccc gaagaacgtt   3660
ttccaatgat gagcactttt aaagttctgc tatgtggcgc ggtattatcc cgtattgacg   3720
ccgggcaaga gcaactcggt cgccgcatac actattctca gaatgacttg gttgagtact   3780
caccagtcac agaaaagcat cttacggatg gcatgacagt aagagaatta tgcagtgctg   3840
ccataaccat gagtgataac actgcggcca acttacttct gacaacgatc ggaggaccga   3900
aggagctaac cgcttttttg cacaacatgg gggatcatgt aactcgcctt gatcgttggg   3960
aaccggagct gaatgaagcc ataccaaacg acgagcgtga caccacgatg cctgtagcaa   4020
```

-continued

```
tggcaacaac gttgcgcaaa ctattaactg gcgaactact tactctagct tcccggcaac   4080
aattaataga ctggatggag gcggataaag ttgcaggacc acttctgcgc tcggcccttc   4140
cggctggctg gtttattgct gataaatctg gagccggtga gcgtgggtct cgcggtatca   4200
ttgcagcact ggggccagat ggtaagccct cccgtatcgt agttatctac acgacgggga   4260
gtcaggcaac tatggatgaa cgaaatagac agatcgctga gataggtgcc tcactgatta   4320
agcattggta actgtcagac caagtttact catatatact ttagattgat ttaaaacttc   4380
atttttaatt taaaaggatc taggtgaaga tcctttttga taatctcatg accaaaatcc   4440
cttaacgtga gttttcgttc cactgagcgt cagaccccgt agaaaagatc aaaggatctt   4500
cttgagatcc tttttttctg cgcgtaatct gctgcttgca aacaaaaaaa ccaccgctac   4560
cagcggtggt ttgtttgccg gatcaagagc taccaactct ttttccgaag gtaactggct   4620
tcagcagagc gcagatacca aatactgtcc ttctagtgta gccgtagtta ggccaccact   4680
tcaagaactc tgtagcaccg cctacatacc tcgctctgct aatcctgtta ccagtggctg   4740
ctgccagtgg cgataagtcg tgtcttaccg ggttggactc aagacgatag ttaccggata   4800
aggcgcagcg gtcgggctga acggggggtt cgtgcacaca gcccagcttg gagcgaacga   4860
cctacaccga actgagatac ctacagcgtg agctatgaga aagcgccacg cttcccgaag   4920
ggagaaaggc ggacaggtat ccggtaagcg gcagggtcgg aacaggagag cgcacgaggg   4980
agcttccagg gggaaacgcc tggtatcttt atagtcctgt cgggtttcgc cacctctgac   5040
ttgagcgtcg atttttgtga tgctcgtcag gggggcggag cctatggaaa aacgccagca   5100
acgcggcctt tttacggttc ctggcctttt gctggccttt tgctcacatg ttctttcctg   5160
cgttatcccc tgattctgtg gataaccgta ttaccgcctt tgagtgagct gataccgctc   5220
gccgcagccg aacgaccgag cgcagcgagt cagtgagcga ggaagcggaa gagcgcccaa   5280
tacgcaaacc gcctctcccc gcgcgttggc cgattcatta atgcagctgg cacgacaggt   5340
ttcccgactg gaaagcgggc agtgagcgca acgcaattaa tgtgagttag ctcactcatt   5400
aggcacccca ggctttacac tttatgcttc cggctcgtat gttgtgtgga attgtgagcg   5460
gataacaatt tcacacagga aacagctatg accatgatta cgaattgcgg ccgcaattct   5520
gaatgttaaa tgttatactt tggatgaagc tataaatatg cattggaaaa ataatccatt   5580
taaagaaagg attcaaatac tacaaaacct aagcgataat atgttaacta agcttattct   5640
taacgacgct ttaaatatac acaaataaac ataatttttg tataacctaa caaataacta   5700
aaacataaaa ataataaaag gaaatgtaat atcgtaatta ttttactcag gaatggggtt   5760
aaatatttat atcacgtgta tatctatact gttatcgtat actctttaca attactatta   5820
cgaatatgca agagataata agattacgta tttaagagaa tcttgtcatg ataattgggt   5880
acgacatagt gataaatgct atttcgcatc gttacataaa gtcagttgga aagatggatt   5940
tgacagatgt aacttaatag gtgcaaaaat gttaaataac agcattctat cggaagatag   6000
gataccagtt atattataca aaaatcactg gttggataaa acagattctg caatattcgt   6060
aaaagatgaa gattactgcg aatttgtaaa ctatgacaat aaaaagccat ttatctcaac   6120
gacatcgtgt aattcttcca tgttttatgt atgtgtttca gatattatga gattactata   6180
aactttttgt atacttatat tccgtaaact atattaatca tgaagaaaat gaaaaagtat   6240
agaagctgtt cacgagcggt tgttgaaaac aacaaaatta tacattcaag atggcttaca   6300
tatacgtctg tgaggctatc atggataatg acaatgcatc tctaaatagg tttttggaca   6360
atggattcga ccctaacacg gaatatggta ctctacaatc tcctcttgaa atggctgtaa   6420
```

tgttcaagaa taccgaggct ataaaaatct tgatgaggta tggagctaaa cctgtagtta 6480
ctgaatgcac aacttcttgt ctgcatgatg cggtgttgag agacgactac aaaatagtga 6540
aagatctgtt gaagaataac tatgtaaaca atgttcttta cagcggaggc tttactcctt 6600
tgtgtttggc agcttacctt aacaaagtta atttggttaa acttctattg gctcattcgg 6660
cggatgtaga tatttcaaac acggatcggt taactcctct 6700

<210> SEQ ID NO 8
<211> LENGTH: 4193
<212> TYPE: DNA
<213> ORGANISM: artificial sequence
<220> FEATURE:
<223> OTHER INFORMATION: pJSY2218.1 seq containing arms and insert

<400> SEQUENCE: 8
ctttatacta ctgggttaca acagctggtg ataacagaat gtaaatcatt attacttaat 60
agttccatta ttatatgttt gatatctata ggtaacctac ctattattcc tagattctta 120
ctctctttta cagctttaac tattagctga tgtctatgaa aagctaatga tttatttttc 180
cgtattaatt ccctatatat acgtatacat gcaggtatct tattaactct aggattagtt 240
acgaacttta ccataagatc tatgttattg tcaagaaaga tattaaaaga atatatagaa 300
tttaacttta tatgtgttat aacatctagt tctttttcgc atgattcttt tatagatagt 360
agtcttttat tactgtttat atgttccatg tttactataa aaccttctga attagctatt 420
tcaggatttt tagatatttc taacatcatt ttagatatta tcataatagc tatcttgtca 480
tctaaaaagc taacacaagt tagaggcgta ttaccgtgat tatttagaga attatagtcg 540
gcgttataag ataaaagtaa ttttatatta ttaaaactat tagataacat agctttatgt 600
aaaggagtat ttccagataa cttagcttta gcatttacgt aagcaccgtg gtcaagtaag 660
agtttaacaa attctgtttt catagaacta actgccatgt atagaggagt gaaaccttta 720
tgattataga cgtttacata gcaaccatat aataagatcg cattcagtat attaatatct 780
ttcatttcta tagctatgtg aataacatgt ttatctaatc ctaccaactt tgtatcagta 840
ccgtacttca gtaataagtt tactatagtt ttgtttttag atgcaacagc tatatttaga 900
acggtatcta tatgattatt aaccacatta acattagatc ctctttctaa aagtgtcttt 960
gttgtttcga tatcgttacg tgaaacagcg taatgtaagg gactgcccat acagtcatct 1020
attacgttta tatcagctcc tagatttaac agaagtgctg ttacatcttt tcttctatta 1080
attaccgaat gatgtaatgg ggttttacct aaatcatctt gttcgtttat aggcactccg 1140
tgatttataa gtaacgctat tatatcgtaa ctacaattat ttttaagtgc ctttatgaga 1200
tactgtttat gcaaaaataa acttttatct attttaatac tattatctaa caatatccta 1260
attaaatcta tattcttata ctttatagcg taatgtaacg gagtttcaaa atttctagtt 1320
tgtatattaa gatcaatatt aaaatctata aatattttat acatatcatc agatatctta 1380
tcatacagta catcgtaata atttagaaag aatctattac aattaacacc ttttttttaat 1440 aaatatctag ttaatgactt attgtttcta tatacagaaa tatataacgg actatttcca 1500
gaatgtatct gttctatgtc agcgccagaa tctattagta gtttagcaat ttctgtatta 1560
tctaaactag cagctttatg aagaggagga tttttacatt ttaaaatatc ggcaccgtgt 1620
tctagtaata attttaccat ttctatatca gaaatactta cggctaaata caaagacgtt 1680
gatagtatat ttacgttatt gtatttgcat tttttaagta tataccttac taaatttata 1740

-continued

```
tctctatacc ttatagcttt atgcagttca tttataagtc ttccattact catttctggt   1800
aatgaagtat tatatatcat tatgatatta tctctatttt attctaataa aaaccgttat   1860
catgttattt attatttgtt ataattatac tatttaataa attataccaa atacttagat   1920
acttattaat accatcctag aacttgtatt tcttgccccc taaacttgga catgcactcc   1980
attaggcgtt tcttgttttc gacatcgtcc tccttaacat atcctactgt tatgtgagga   2040
ttccacggat tatctactgt gatatcacca aacacgtcct tcgaacaggg taccgcattc   2100
agcagaacat ttcttagggc tctaagttca tcagatacct ccagtttcat aactacagcg   2160
catcctttcg ctcccaactg tttagaggcg ttactctgag gaaaacacat ctcttcttta   2220
cagactatag aaatagtctg taaatcttga tcagttattt gctttttgaa attttcaaat   2280
ctatcacatt gatccatatt tgctattcca agagttatat gaggaaaaat atcacatcct   2340
gtcatgtatt ttattgtaac attattataa tctgtaacat cagtatctaa cctaacgtcg   2400
taaaagttaa cagatgccca gttactataa tcccaaggaa ccttaacatc taatcccatt   2460
aaaatagtat cctttctact attttttca ttggcaagta tgtggcttag tttacacaaa   2520
attcctgcca ttttgtaacg atagcgaagc aatagcttgt atgcttttta tttgattaac   2580
taggggttaa ttaattagtc atcaggcagg gcgagaacga gactatctgc tcgttaatta   2640
attagagctt ctttattcta tacttaaaaa gtgaaaataa atacaaaggt tcttgagggt   2700
tgtgttaaat tgaaagcgag aaataatcat aaattatttc attatcgcga tatccgttaa   2760
gtttgtatcg taatgtggct gcagaacctg ctgttcctgg gcaccgtggt gtgcagcatc   2820
agcgccccca ccagatcccc caccctggtg acccggccca gccagcacgt ggacgccatc   2880
caggaagccc tgagcctgct gaacaacagc aacgacgtga ccgccgtgat gaacaaggcc   2940
gtgaaggtgg tgtccgaggt gttcgacccc gagggcccca cctgcctgga aacccggctg   3000
cagctgtaca aagagggcct gcagggcagc ctgaccagcc tgaagaaccc cctgaccatg   3060
atggccaacc actacaagca gcactgcccc cccacccccg agagcccttg cgccacccag   3120
aacatcaact tcaagagctt caaagagaac ctgaaggact tcctgttcaa catccccttc   3180
gactgctgga agcccgtgaa gaagtgatga ctcgagtttt tattgactag ggtttttat   3240
agctaattag tcaaatgtga gttaatatta gtatactaca ttactaattt attacatatt   3300
catttatatc aatctagtag catttagctt ttataaaaca atataactga atagtacata   3360
ctttactaat aagttataaa taagagatac atatttatag tattttactt tctacactga   3420
atataataat ataattatac aaatataatt tttaatacta tatagtatat aactgaaata   3480
aaataccagt gtaatatagt tattatacat ttataccaca tcaaagatga gttataacat   3540
cagtgtcact gttagcaaca gtagttatac gatgagtagt tactctcgta tggcgttagt   3600
atgtatgtat cttctagttt tcttagtagg cattatagga aacgtcaagc ttataaggtt   3660
attaatggta tctagaaata tatctattat accgtttctc aacttgggaa tagccgattt   3720
gctgtttgtg atattcatac ctttatacat tatatacata ctaagtaatt tccattggca   3780
ttttggtaaa gcactttgta aaattagttc tttcttttt acttctaaca tgtttgcaag   3840
tatattttta ataactgtaa taagcgtata tagatatgta aaaattaccc ttcctggatt   3900
tacctataaa tatgttaaca ttagaaatat gtacattact atatttttca tatggattat   3960
ttctattata ctagggattc ctgctcttta ctttagaaat actatcgtaa caaaaaataa   4020
cgacacgctg tgtattaatc attatcatga taatagagaa attgctgaat tgatttacaa   4080
agttattatc tgtatcagat ttattttagg atacctacta cctacgataa ttatactcgt   4140
```

atgctatacg ttactgatct acagaactaa caatgcatgt cgacgcggcc gca 4193

<210> SEQ ID NO 9
<211> LENGTH: 6842
<212> TYPE: DNA
<213> ORGANISM: artificial sequence
<220> FEATURE:
<223> OTHER INFORMATION: pJSY2218.1 entire plasmid sequence

<400> SEQUENCE: 9
tgcggccgcg tcgacatgca ttgttagttc tgtagatcag taacgtatag catacgagta 60
taattatcgt aggtagtagg tatcctaaaa taaatctgat acagataata actttgtaaa 120
tcaattcagc aatttctcta ttatcatgat aatgattaat acacagcgtg tcgttatttt 180
ttgttacgat agtatttcta aagtaaagag caggaatccc tagtataata gaaataatcc 240
atatgaaaaa tatagtaatg tacatatttc taatgttaac atatttatag gtaaatccag 300
gaagggtaat ttttacatat ctatatacgc ttattacagt tattaaaaat atacttgcaa 360
acatgttaga agtaaaaaag aaagaactaa ttttacaaag tgctttacca aaatgccaat 420
ggaaattact tagtatgtat ataatgtata aaggtatgaa tatcacaaac agcaaatcgg 480
ctattcccaa gttgagaaac ggtataatag atatatttct agataccatt aataacctta 540
taagcttgac gtttcctata atgcctacta agaaaactag aagatacata catactaacg 600
ccatacgaga gtaactactc atcgtataac tactgttgct aacagtgaca ctgatgttat 660
aactcatctt tgatgtggta taaatgtata ataactatat tacactggta ttttatttca 720
gttatatact atatagtatt aaaaattata tttgtataat tatattatta tattcagtgt 780
agaaagtaaa atactataaa tatgtatctc ttatttataa cttattagta aagtatgtac 840
tattcagtta tattgtttta taaaagctaa atgctactag attgatataa atgaatatgt 900
aataaattag taatgtagta tactaatatt aactcacatt tgactaatta gctataaaaa 960
cccctagtca ataaaaactc gagtcatcac ttcttcacgg gcttccagca gtcgaagggg 1020
atgttgaaca ggaagtcctt caggttctct ttgaagctct tgaagttgat gttctgggtg 1080
gcgcaagggc tctcgggggt ggggggcag tgctgcttgt agtggttggc catcatggtc 1140
agggggttct tcaggctggt caggctgccc tgcaggccct ctttgtacag ctgcagccgg 1200
gtttccaggc aggtggggcc ctcggggtcg aacacctcgg acaccacctt cacggccttg 1260
ttcatcacgg cggtcacgtc gttgctgttg ttcagcaggc tcagggcttc ctggatggcg 1320
tccacgtgct ggctgggccg ggtcaccagg gtgggggatc tggtgggggc gctgatgctg 1380
cacaccacgg tgcccaggaa cagcaggttc tgcagccaca ttacgataca aacttaacgg 1440
atatcgcgat aatgaaataa tttatgatta tttctcgctt tcaatttaac acaaccctca 1500
agaacctttg tatttatttt cactttttaa gtatagaata aagaagctct aattaattaa 1560
cgagcagata gtctcgttct cgccctgcct gatgactaat taattaaccc ctagttaatc 1620
aaataaaaag catacaagct attgcttcgc tatcgttaca aaatggcagg aattttgtgt 1680
aaactaagcc acatacttgc caatgaaaaa aatagtagaa aggatactat tttaatggga 1740
ttagatgtta aggttccttg ggattatagt aactgggcat ctgttaactt ttacgacgtt 1800
aggttagata ctgatgttac agattataat aatgttacaa taaaatacat gacaggatgt 1860
gatatttttc ctcatataac tcttggaata gcaaatatgg atcaatgtga tagatttgaa 1920
aatttcaaaa agcaaataac tgatcaagat ttacagacta tttctatagt ctgtaaagaa 1980

-continued

```
gagatgtgtt ttcctcagag taacgcctct aaacagttgg gagcgaaagg atgcgctgta   2040
gttatgaaac tggaggtatc tgatgaactt agagccctaa gaaatgttct gctgaatgcg   2100
gtaccctgtt cgaaggacgt gtttggtgat atcacagtag ataatccgtg gaatcctcac   2160
ataacagtag gatatgttaa ggaggacgat gtcgaaaaca agaaacgcct aatggagtgc   2220
atgtccaagt ttagggggca agaaatacaa gttctaggat ggtattaata agtatctaag   2280
tatttggtat aatttattaa atagtataat tataacaaat aataaataac atgataacgg   2340
tttttattag aataaaatag agataatatc ataatgatat ataatacttc attaccagaa   2400
atgagtaatg gaagacttat aaatgaactg cataaagcta taaggtatag agatataaat   2460
ttagtaaggt atatacttaa aaaatgcaaa tacaataacg taaatatact atcaacgtct   2520
ttgtatttag ccgtaagtat ttctgatata gaaatggtaa aattattact agaacacggt   2580
gccgatattt taaaatgtaa aaatcctcct cttcataaag ctgctagttt agataataca   2640
gaaattgcta aactactaat agattctggc gctgacatag aacagataca ttctggaaat   2700
agtccgttat atatttctgt atatagaaac aataagtcat taactagata tttattaaaa   2760
aaaggtgtta attgtaatag attctttcta aattattacg atgtactgta tgataagata   2820
tctgatgata tgtataaaat atttatagat tttaatattg atcttaatat acaaactaga   2880
aattttgaaa ctccgttaca ttacgctata aagtataaga atatagattt aattaggata   2940
ttgttagata atagtattaa aatagataaa agtttatttt tgcataaaca gtatctcata   3000
aaggcactta aaaataattg tagttacgat ataatagcgt tacttataaa tcacggagtg   3060
cctataaacg aacaagatga tttaggtaaa accccattac atcattcggt aattaataga   3120
agaaaagatg taacagcact tctgttaaat ctaggagctg atataaacgt aatagatgac   3180
tgtatgggca gtcccttaca ttacgctgtt tcacgtaacg atatcgaaac aacaaagaca   3240
cttttagaaa gaggatctaa tgttaatgtg gttaataatc atatagatac cgttctaaat   3300
atagctgttg catctaaaaa caaaactata gtaaacttat tactgaagta cggtactgat   3360
acaaagttgg taggattaga taaacatgtt attcacatag ctatagaaat gaaagatatt   3420
aatatactga atgcgatctt attatatggt tgctatgtaa acgtctataa tcataaaggt   3480
ttcactcctc tatacatggc agttagttct atgaaaacag aatttgttaa actcttactt   3540
gaccacggtg cttacgtaaa tgctaaagct aagttatctg gaaatactcc tttacataaa   3600
gctatgttat ctaatagttt taataatata aaattacttt tatcttataa cgccgactat   3660
aattctctaa ataatcacgg taatacgcct ctaacttgtg ttagcttttt agatgacaag   3720
atagctatta tgataatatc taaaatgatg ttagaaatat ctaaaaatcc tgaaatagct   3780
aattcagaag gttttatagt aaacatggaa catataaaca gtaataaaag actactatct   3840
ataaaagaat catgcgaaaa agaactagat gttataacac atataaagtt aaattctata   3900
tattctttta atatctttct tgacaataac atagatctta tggtaaagtt cgtaactaat   3960
cctagagtta ataagatacc tgcatgtata cgtatatata gggaattaat acggaaaaat   4020
aaatcattag cttttcatag acatcagcta atagttaaag ctgtaaaaga gagtaagaat   4080
ctaggaataa taggtaggtt acctatagat atcaaacata taataatgga actattaagt   4140
aataatgatt tacattctgt tatcaccagc tgttgtaacc cagtagtata aagagctcga   4200
attaattcac tggccgtcgt tttacaacgt cgtgactggg aaaaccctgg cgttacccaa   4260
cttaatcgcc ttgcagcaca tccccctttc gccagctggc gtaatagcga agaggcccgc   4320
accgatcgcc cttcccaaca gttgcgcagc ctgaatggcg aatggcgcct gatgcggtat   4380
```

-continued

```
tttctcctta cgcatctgtg cggtatttca caccgcatat ggtgcactct cagtacaatc   4440
tgctctgatg ccgcatagtt aagccagccc cgacacccgc caacacccgc tgacgcgccc   4500
tgacgggctt gtctgctccc ggcatccgct tacagacaag ctgtgaccgt ctccgggagc   4560
tgcatgtgtc agaggttttc accgtcatca ccgaaacgcg cgagacgaaa gggcctcgtg   4620
atacgcctat ttttataggt taatgtcatg ataataatgg tttcttagac gtcaggtggc   4680
acttttcggg gaaatgtgcg cggaacccct atttgtttat ttttctaaat acattcaaat   4740
atgtatccgc tcatgagaca ataaccctga taaatgcttc aataatattg aaaaaggaag   4800
agtatgagta ttcaacattt ccgtgtcgcc cttattccct tttttgcggc attttgcctt   4860
cctgtttttg ctcacccaga aacgctggtg aaagtaaaag atgctgaaga tcagttgggt   4920
gcacgagtgg gttacatcga actggatctc aacagcggta agatccttga gagttttcgc   4980
cccgaagaac gttttccaat gatgagcact tttaaagttc tgctatgtgg cgcggtatta   5040
tcccgtattg acgccgggca agagcaactc ggtcgccgca tacactattc tcagaatgac   5100
ttggttgagt actcaccagt cacagaaaag catcttacgg atggcatgac agtaagagaa   5160
ttatgcagtg ctgccataac catgagtgat aacactgcgg ccaacttact tctgacaacg   5220
atcggaggac cgaaggagct aaccgctttt ttgcacaaca tgggggatca tgtaactcgc   5280
cttgatcgtt gggaaccgga gctgaatgaa gccataccaa acgacgagcg tgacaccacg   5340
atgcctgtag caatggcaac aacgttgcgc aaactattaa ctggcgaact acttactcta   5400
gcttcccggc aacaattaat agactggatg gaggcggata aagttgcagg accacttctg   5460
cgctcggccc ttccggctgg ctggtttatt gctgataaat ctggagccgg tgagcgtggg   5520
tctcgcggta tcattgcagc actggggcca gatggtaagc cctcccgtat cgtagttatc   5580
tacacgacgg ggagtcaggc aactatggat gaacgaaata gacagatcgc tgagataggt   5640
gcctcactga ttaagcattg gtaactgtca gaccaagttt actcatatat actttagatt   5700
gatttaaaac ttcattttta atttaaaagg atctaggtga agatcctttt tgataatctc   5760
atgaccaaaa tcccttaacg tgagttttcg ttccactgag cgtcagaccc cgtagaaaag   5820
atcaaaggat cttcttgaga tccttttttt ctgcgcgtaa tctgctgctt gcaaacaaaa   5880
aaaccaccgc taccagcggt ggtttgtttg ccggatcaag agctaccaac tctttttccg   5940
aaggtaactg gcttcagcag agcgcagata ccaaatactg tccttctagt gtagccgtag   6000
ttaggccacc acttcaagaa ctctgtagca ccgcctacat acctcgctct gctaatcctg   6060
ttaccagtgg ctgctgccag tggcgataag tcgtgtctta ccgggttgga ctcaagacga   6120
tagttaccgg ataaggcgca gcggtcgggc tgaacggggg gttcgtgcac acagcccagc   6180
ttggagcgaa cgacctacac cgaactgaga tacctacagc gtgagctatg agaaagcgcc   6240
acgcttcccg aagggagaaa ggcggacagg tatccggtaa gcggcagggt cggaacagga   6300
gagcgcacga gggagcttcc agggggaaac gcctggtatc tttatagtcc tgtcgggttt   6360
cgccacctct gacttgagcg tcgatttttg tgatgctcgt caggggggcg gagcctatgg   6420
aaaaacgcca gcaacgcggc ctttttacgg ttcctggcct tttgctggcc ttttgctcac   6480
atgttctttc ctgcgttatc ccctgattct gtggataacc gtattaccgc ctttgagtga   6540
gctgataccg ctcgccgcag ccgaacgacc gagcgcagcg agtcagtgag cgaggaagcg   6600
gaagagcgcc caatacgcaa accgcctctc cccgcgcgtt ggccgattca ttaatgcagc   6660
tggcacgaca ggtttcccga ctggaaagcg ggcagtgagc gcaacgcaat taatgtgagt   6720
```

tagctcactc attaggcacc ccaggcttta cactttatgc ttccggctcg tatgttgtgt 6780
ggaattgtga gcggataaca atttcacaca ggaaacagct atgaccatga ttacgccaag 6840
ct 6842

<210> SEQ ID NO 10
<211> LENGTH: 24
<212> TYPE: DNA
<213> ORGANISM: artificial sequence
<220> FEATURE:
<223> OTHER INFORMATION: 13220CXL primer

<400> SEQUENCE: 10
aggtgtccac ctccaacatg gagt 24

<210> SEQ ID NO 11
<211> LENGTH: 24
<212> TYPE: DNA
<213> ORGANISM: artificial sequence
<220> FEATURE:
<223> OTHER INFORMATION: 13225CXL primer

<400> SEQUENCE: 11
gaactggtcg cccctggagg cctt 24

<210> SEQ ID NO 12
<211> LENGTH: 25
<212> TYPE: DNA
<213> ORGANISM: artificial sequence
<220> FEATURE:
<223> OTHER INFORMATION: 7931DC primer

<400> SEQUENCE: 12
gaatctgtta gttagttact tggat 25

<210> SEQ ID NO 13
<211> LENGTH: 25
<212> TYPE: DNA
<213> ORGANISM: artificial sequence
<220> FEATURE:
<223> OTHER INFORMATION: 7932DC primer

<400> SEQUENCE: 13
tgattatagc tattatcaca gactc 25

<210> SEQ ID NO 14
<211> LENGTH: 4279
<212> TYPE: DNA
<213> ORGANISM: artificial sequence
<220> FEATURE:
<223> OTHER INFORMATION: vCP2263 containing arms and insert
<220> FEATURE:
<221> NAME/KEY: misc_feature
<222> LOCATION: (126)..(1661)
<223> OTHER INFORMATION: this is the C5 arm region
<220> FEATURE:
<221> NAME/KEY: promoter
<222> LOCATION: (1759)..(1882)
<220> FEATURE:
<221> NAME/KEY: CDS
<222> LOCATION: (1883)..(3703)
<223> OTHER INFORMATION: this is the HA protein encoding region
<220> FEATURE:
<221> NAME/KEY: misc_feature
<222> LOCATION: (3760)..(4164)
<223> OTHER INFORMATION: this is the C5 arm region

<400> SEQUENCE: 14

-continued

```
gaatctgtta gttagttact tggataaatt aatcgagacg cgtgataaaa tgactatgta     60
ccgttattgc atgaacgata ttataaatat aggttctcgt aggagagaac tattgactat    120
ggcaatgaat gttaaatgtt atactttgga tgaagctata aatatgcatt ggaaaaataa    180
tccatttaaa gaaaggattc aaatactaca aaacctaagc gataatatgt taactaagct    240
tattcttaac gacgctttaa atatacacaa ataaacataa tttttgtata acctaacaaa    300
taactaaaac ataaaaataa taaaaggaaa tgtaatatcg taattatttt actcaggaat    360
ggggttaaat atttatatca cgtgtatatc tatactgtta tcgtatactc tttacaatta    420
ctattacgaa tatgcaagag ataataagat tacgtattta agagaatctt gtcatgataa    480
ttgggtacga catagtgata aatgctattt cgcatcgtta cataaagtca gttggaaaga    540
tggatttgac agatgtaact taataggtgc aaaaatgtta aataacagca ttctatcgga    600
agataggata ccagttatat tatacaaaaa tcactggttg gataaaacag attctgcaat    660
attcgtaaaa gatgaagatt actgcgaatt tgtaaactat gacaataaaa agccatttat    720
ctcaacgaca tcgtgtaatt cttccatgtt ttatgtatgt gtttcagata ttatgagatt    780
actataaact ttttgtatac ttatattccg taaactatat taatcatgaa gaaaatgaaa    840
aagtatagaa gctgttcacg agcggttgtt gaaaacaaca aaattataca ttcaagatgg    900
cttacatata cgtctgtgag gctatcatgg ataatgacaa tgcatctcta aataggtttt    960
tggacaatgg attcgaccct aacacggaat atggtactct acaatctcct cttgaaatgg   1020
ctgtaatgtt caagaatacc gaggctataa aaatcttgat gaggtatgga gctaaacctg   1080
tagttactga atgcacaact tcttgtctgc atgatgcggt gttgagagac gactacaaaa   1140
tagtgaaaga tctgttgaag aataactatg taaacaatgt tctttacagc ggaggcttta   1200
ctcctttgtg tttggcagct taccttaaca aagttaattt ggttaaactt ctattggctc   1260
attcggcgga tgtagatatt tcaaacacgg atcggttaac tcctctacat atagccgtat   1320
caaataaaaa tttaacaatg gttaaacttc tattgaacaa aggtgctgat actgacttgc   1380
tggataacat gggacgtact cctttaatga tcgctgtaca atctggaaat attgaaatat   1440
gtagcacact acttaaaaaa aataaaatgt ccagaactgg gaaaaattga tcttgccagc   1500
tgtaattcat ggtagaaaag aagtgctcag gctacttttc aacaaaggag cagatgtaaa   1560
ctacatcttt gaaagaaatg gaaaatcata tactgttttg gaattgatta aagaaagtta   1620
ctctgagaca caaaagaggt agctgaagtg gtactctcaa aggtacgtga ctaattagct   1680
ataaaaagga tccgggttaa ttaattagtc atcaggcagg gcgagaacga gactatctgc   1740
tcgttaatta attagagctt ctttattcta tacttaaaaa gtgaaaataa atacaaaggt   1800
tcttgagggt tgtgttaaat tgaaagcgag aaataatcat aaattatttc attatcgcga   1860
tatccgttaa gtttgtatcg taatgctgag ctaccaggac aaagtgggcg ccttctacaa   1920
ggacaacgcc agggccaata gcagcaagct gagcctggtg accgaggagc agggcggcag   1980
gagacccccc tacctgctgt tcgtgctgct gatccttctt gtgggcatca tgaccctgct   2040
ggccatcacc ggagtgagat tccaccaggt gtccacctcc aacatggagt tcagccggct   2100
gctgaaagag gacatggaga agagcgaggc cgtgcaccac caggtgatcg atgtgctgac   2160
ccccctgttc aagatcatcg gcgacgaagt gggcctgaga ctgccccaga agctgaacga   2220
gatcaagcag ttcatcctgc agaaaaccaa cttcttcaac cccaaccggg agttcgactt   2280
cagagacctg cactggtgca tcaacccccc cagcaagatc aaagtgaact tcaccaacta   2340
ctgcgacacc atcggcatca ggaagagcat cgccagcgcc gtgaatccca tcctgctgag   2400
```

-continued

```
cgccctgagc ggcggcagag gcgacatctt cccccctac agatgcagcg gcgccaccac   2460

ctctgtgggc agagtgttcc ctctgagcgt gtccctgagc atgagcctga tcagcaagac   2520

cagcgagatc accaacatgc tgaccgccat cagcgacggc gtgtacggca agacctatct   2580

gctggtgccc gactacatcg agggcgagtt cgacacccag aagatccgcg tgttcgagat   2640

cggcttcatc aagcggtggc tgaacaacat gcccctgctg cagaccacca actacatggt   2700

gctgcccgag aacagcaagg ccaaagtgtg caccatcgct gtgggcgagc tgaccctggc   2760

cagcctgtgc gtggacgaga gcaccgtgct gctgtaccac gacagcaacg gcagccagga   2820

cggcatcctg gtggtgaccc tgggcatctt cggcgccacc cctatggacc aggtggagga   2880

agtgatcccc gtggcccacc ccagcgtgga gaagatccac atcaccaacc accggggctt   2940

tatcaaggac agcatcgcca cctggatggt gcccgccctg gtgtctgaga agcaggagga   3000

gcagaagaac tgcctggaga gcgcctgcca gagaaagacc taccccatgt gcaaccagac   3060

cagctgggag ccctttggcg gcggacagct gcccagctac ggcagactga ccctgagcct   3120

ggaccctagc atcgacctgc agctgaacat cagcttcacc tacggccccg tgatcctgaa   3180

cggcgacggc atggattact acggcagcag cctgagcgac agcggctggc tgaccatccc   3240

tcccaagaac ggcacagtgc tgggcctgat caacaaggcc tccaggggcg accagttcac   3300

cgtgatccct cacgtgctga ccttcgcccc cagagagagc agcggcaact gctacctgcc   3360

tatccagacc tcccagatca tggacaagga cgtgctgaca gagagcaacc tggtggtgct   3420

gcctacccag aacttccggt acgtgatcgc cacctacgac atcagcagag gcgatcacgc   3480

catcgtgtac tacgtgtacg accccatccg gaccatcagc tacacatacc ccttccggct   3540

gaccaccaag ggcagacccg acttcctgcg gatcgagtgc tttgtgtggg acgacgacct   3600

gtggtgccac cagttctaca gattcgaggc cgacatcacc aatagcacca cctccgtgga   3660

gaaccttgtg aggatccggt tcagctgcga cagaagcaag ccctgatagc tcgagtctag   3720

aatcgatccc gggtttttat gactagttaa tcacggccgc ttataaagat ctaaaatgca   3780

taatttctaa ataatgaaaa aaagtacatc atgagcaacg cgttagtata ttttacaatg   3840

gagattaacg ctctataccg ttctatgttt attgattcag atgatgtttt agaaaagaaa   3900

gttattgaat atgaaaactt taatgaagat gaagatgacg acgatgatta ttgttgtaaa   3960

tctgttttag atgaagaaga tgacgcgcta aagtatacta tggttacaaa gtataagtct   4020

atactactaa tggcgacttg tgcaagaagg tatagtatag tgaaaatgtt gttagattat   4080

gattatgaaa aaccaaataa atcagatcca tatctaaagg tatctccttt gcacataatt   4140

tcatctattc ctagtttaga atacttttca ttatatttgt ttacagctga agacgaaaaa   4200

aatatatcga taatagaaga ttatgttaac tctgctaata agatgaaatt gaatgagtct   4260

gtgataatag ctataatca                                                4279
```

```
<210> SEQ ID NO 15
<211> LENGTH: 26
<212> TYPE: DNA
<213> ORGANISM: artificial sequence
<220> FEATURE:
<223> OTHER INFORMATION: 18071BK primer

<400> SEQUENCE: 15

gatgttgaac aggaagtcct tcaggt                                          26


<210> SEQ ID NO 16
```

-continued

<211> LENGTH: 26
<212> TYPE: DNA
<213> ORGANISM: artificial sequence
<220> FEATURE:
<223> OTHER INFORMATION: 18073BK primer

<400> SEQUENCE: 16
gttcctgggc accgtggtgt gcagca 26

<210> SEQ ID NO 17
<211> LENGTH: 30
<212> TYPE: DNA
<213> ORGANISM: artificial sequence
<220> FEATURE:
<223> OTHER INFORMATION: 8103JY primer

<400> SEQUENCE: 17
gaggcatcca acatataaag aagactaaag 30

<210> SEQ ID NO 18
<211> LENGTH: 27
<212> TYPE: DNA
<213> ORGANISM: artificial sequence
<220> FEATURE:
<223> OTHER INFORMATION: 8104JY primer

<400> SEQUENCE: 18
tagttaaata ctcataactc atatctg 27

<210> SEQ ID NO 19
<211> LENGTH: 4350
<212> TYPE: DNA
<213> ORGANISM: artificial sequence
<220> FEATURE:
<223> OTHER INFORMATION: part of vCP2391 containing C3L-canine
GM-CSF-C3R
<220> FEATURE:
<221> NAME/KEY: misc_feature
<222> LOCATION: (72)..(2643)
<223> OTHER INFORMATION: this is the C3 arm region
<220> FEATURE:
<221> NAME/KEY: promoter
<222> LOCATION: (2658)..(2843)
<220> FEATURE:
<221> NAME/KEY: CDS
<222> LOCATION: (2844)..(3281)
<223> OTHER INFORMATION: this is the GM_CSF coding region
<220> FEATURE:
<221> NAME/KEY: misc_feature
<222> LOCATION: (3323)..(4249)
<223> OTHER INFORMATION: this is the C3 arm region

<400> SEQUENCE: 19
ctttagttaa atactcataa ctcatatctg ttaacaaatt taatgtttat cttcgtaatt 60
gaataaaatc actttatact actgggttac aacagctggt gataacagaa tgtaaatcat 120
tattacttaa tagttccatt attatatgtt tgatatctat aggtaaccta cctattattc 180
ctagattctt actctctttt acagctttaa ctattagctg atgtctatga aaagctaatg 240
atttattttt ccgtattaat tccctatata tacgtataca tgcaggtatc ttattaactc 300
taggattagt tacgaacttt accataagat ctatgttatt gtcaagaaag atattaaaag 360
aatatataga atttaacttt atatgtgtta taacatctag ttctttttcg catgattctt 420
ttatagatag tagtctttta ttactgttta tatgttccat gtttactata aaaccttctg 480
aattagctat ttcaggattt ttagatattt ctaacatcat tttagatatt atcataatag 540
ctatcttgtc atctaaaaag ctaacacaag ttagaggcgt attaccgtga ttatttagag 600

```
aattatagtc ggcgttataa gataaaagta attttatatt attaaaacta ttagataaca    660
tagctttatg taaaggagta tttccagata acttagcttt agcatttacg taagcaccgt    720
ggtcaagtaa gagtttaaca aattctgttt tcatagaact aactgccatg tatagaggag    780
tgaaaccttt atgattatag acgtttacat agcaaccata taataagatc gcattcagta    840
tattaatatc tttcatttct atagctatgt gaataacatg tttatctaat cctaccaact    900
ttgtatcagt accgtacttc agtaataagt ttactatagt tttgttttta gatgcaacag    960
ctatatttag aacggtatct atatgattat taaccacatt aacattagat cctctttcta   1020
aaagtgtctt tgttgtttcg atatcgttac gtgaaacagc gtaatgtaag ggactgccca   1080
tacagtcatc tattacgttt atatcagctc ctagatttaa cagaagtgct gttacatctt   1140
ttcttctatt aattaccgaa tgatgtaatg gggttttacc taaatcatct tgttcgttta   1200
taggcactcc gtgatttata agtaacgcta ttatatcgta actacaatta tttttaagtg   1260
cctttatgag atactgttta tgcaaaaata aacttttatc tattttaata ctattatcta   1320
acaatatcct aattaaatct atattcttat actttatagc gtaatgtaac ggagtttcaa   1380
aatttctagt ttgtatatta agatcaatat taaaatctat aaatatttta tacatatcat   1440
cagatatctt atcatacagt acatcgtaat aatttagaaa gaatctatta caattaacac   1500
cttttttaa taaatatcta gttaatgact tattgtttct atatacagaa atatataacg   1560
gactatttcc agaatgtatc tgttctatgt cagcgccaga atctattagt agtttagcaa   1620
tttctgtatt atctaaacta gcagctttat gaagaggagg atttttacat tttaaaatat   1680
cggcaccgtg ttctagtaat aattttacca tttctatatc agaaatactt acggctaaat   1740
acaaagacgt tgatagtata tttacgttat tgtatttgca ttttttaagt atataccta   1800
ctaaatttat atctctatac cttatagctt tatgcagttc atttataagt cttccattac   1860
tcatttctgg taatgaagta ttatatatca ttatgatatt atctctattt tattctaata   1920
aaaaccgtta tcatgttatt tattatttgt tataattata ctatttaata aattatacca   1980
aatacttaga tacttattaa taccatccta gaacttgtat ttcttgcccc ctaaacttgg   2040
acatgcactc cattaggcgt ttcttgtttt cgacatcgtc ctccttaaca tatcctactg   2100
ttatgtgagg attccacgga ttatctactg tgatatcacc aaacacgtcc ttcgaacagg   2160
gtaccgcatt cagcagaaca tttcttaggg ctctaagttc atcagatacc tccagtttca   2220
taactacagc gcatcctttc gctcccaact gtttagaggc gttactctga ggaaaacaca   2280
tctcttcttt acagactata gaaatagtct gtaaatcttg atcagttatt tgctttttga   2340
aattttcaaa tctatcacat tgatccatat ttgctattcc aagagttata tgaggaaaaa   2400
tatcacatcc tgtcatgtat tttattgtaa cattattata atctgtaaca tcagtatcta   2460
acctaacgtc gtaaaagtta acagatgccc agttactata atcccaagga accttaacat   2520
ctaatcccat taaaatagta tcctttctac tattttttc attggcaagt atgtggctta   2580
gtttacacaa aattcctgcc attttgtaac gatagcgaag caatagcttg tatgcttttt   2640
atttgattaa ctaggggtta attaattagt catcaggcag ggcgagaacg agactatctg   2700
ctcgttaatt aattagagct tctttattct atacttaaaa agtgaaaata aatacaaagg   2760
ttcttgaggg ttgtgttaaa ttgaaagcga gaaataatca taaattattt cattatcgcg   2820
atatccgtta agtttgtatc gtaatgtggc tgcagaacct gctgttcctg ggcaccgtgg   2880
tgtgcagcat cagcgccccc accagatccc ccaccctggt gacccggccc agccagcacg   2940
```

-continued

```
tggacgccat ccaggaagcc ctgagcctgc tgaacaacag caacgacgtg accgccgtga   3000

tgaacaaggc cgtgaaggtg gtgtccgagg tgttcgaccc cgagggcccc acctgcctgg   3060

aaacccggct gcagctgtac aaagagggcc tgcagggcag cctgaccagc ctgaagaacc   3120

ccctgaccat gatggccaac cactacaagc agcactgccc ccccaccccc gagagccctt   3180

gcgccaccca gaacatcaac ttcaagagct tcaaagagaa cctgaaggac ttcctgttca   3240

acatcccctt cgactgctgg aagcccgtga agaagtgatg actcgagttt ttattgacta   3300

ggggttttta tagctaatta gtcaaatgtg agttaatatt agtatactac attactaatt   3360

tattacatat tcatttatat caatctagta gcatttagct tttataaaac aatataactg   3420

aatagtacat actttactaa taagttataa ataagagata catatttata gtattttact   3480

ttctacactg aatataataa tataattata caaatataat ttttaatact atatagtata   3540

taactgaaat aaaataccag tgtaatatag ttattataca tttataccac atcaaagatg   3600

agttataaca tcagtgtcac tgttagcaac agtagttata cgatgagtag ttactctcgt   3660

atggcgttag tatgtatgta tcttctagtt ttcttagtag gcattatagg aaacgtcaag   3720

cttataaggt tattaatggt atctagaaat atatctatta taccgtttct caacttggga   3780

atagccgatt tgctgtttgt gatattcata cctttataca ttatatacat actaagtaat   3840

ttccattggc attttggtaa agcactttgt aaaattagtt ctttcttttt tacttctaac   3900

atgtttgcaa gtatattttt aataactgta ataagcgtat atagatatgt aaaaattacc   3960

cttcctggat ttacctataa atatgttaac attagaaata tgtacattac tatatttttc   4020

atatggatta tttctattat actagggatt cctgctcttt actttagaaa tactatcgta   4080

acaaaaaata acgacacgct gtgtattaat cattatcatg ataatagaga aattgctgaa   4140

ttgatttaca aagttattat ctgtatcaga tttattttag gatacctact acctacgata   4200

attatactcg tatgctatac gttactgatc tacagaacta acaatgcatc taatatatct   4260

gataagatat tcttcataac agcttctaca gctttagtct tctttatatg ttggatgcct   4320

catcacataa ttaatgtaat atctcttttg                                    4350

<210> SEQ ID NO 20
<211> LENGTH: 607
<212> TYPE: PRT
<213> ORGANISM: artificial sequence
<220> FEATURE:
<223> OTHER INFORMATION: AAQ05828

<400> SEQUENCE: 20

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
        35                  40                  45

Ile Met Thr Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Val Gly Leu Arg Leu Pro Gln Lys Leu Asn
            100                 105                 110
```

-continued

```
Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Ile Gly Ile Arg
145                 150                 155                 160

Lys Ser Ile Ala Ser Ala Val Asn Pro Ile Leu Leu Ser Ala Leu Ser
                165                 170                 175

Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Lys Thr Ser Glu Ile Thr Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Glu Phe Asp Thr Gln Lys Ile Arg Val Phe Glu Ile Gly Phe Ile
                245                 250                 255

Lys Arg Trp Leu Asn Asn Met Pro Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Glu Glu Val Ile Pro
                325                 330                 335

Val Ala His Pro Ser Val Glu Lys Ile His Ile Thr Asn His Arg Gly
            340                 345                 350

Phe Ile Lys Asp Ser Ile Ala Thr Trp Met Val Pro Ala Leu Val Ser
        355                 360                 365

Glu Lys Gln Glu Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Leu Thr Leu Ser Leu Asp Pro Ser
                405                 410                 415

Ile Asp Leu Gln Leu Asn Ile Ser Phe Thr Tyr Gly Pro Val Ile Leu
            420                 425                 430

Asn Gly Asp Gly Met Asp Tyr Tyr Gly Ser Ser Leu Ser Asp Ser Gly
        435                 440                 445

Trp Leu Thr Ile Pro Pro Lys Asn Gly Thr Val Leu Gly Leu Ile Asn
    450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Asp Val Tyr Asp Pro Ile Arg Thr
```

```
    530                 535                 540

Ile Ser Tyr Thr His Pro Phe Arg Leu Thr Thr Lys Gly Arg Pro Asp
545                 550                 555                 560

Phe Leu Arg Ile Glu Cys Phe Val Trp Asp Asp Asp Leu Trp Cys His
                565                 570                 575

Gln Phe Tyr Arg Phe Glu Ala Asp Ile Thr Asn Ser Thr Thr Ser Val
            580                 585                 590

Glu Asn Leu Val Arg Ile Arg Phe Ser Cys Asp Arg Ser Lys Pro
        595                 600                 605


<210> SEQ ID NO 21
<211> LENGTH: 607
<212> TYPE: PRT
<213> ORGANISM: artificial sequence
<220> FEATURE:
<223> OTHER INFORMATION: ABF55673

<400> SEQUENCE: 21

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
        35                  40                  45

Ile Met Thr Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Ile Gly Ile Arg
145                 150                 155                 160

Lys Ser Ile Ala Ser Ala Ala Asn Pro Ile Leu Leu Ser Ala Leu Ser
                165                 170                 175

Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Lys Thr Ser Glu Ile Thr Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Glu Phe Asp Thr Gln Lys Ile Arg Val Phe Glu Ile Gly Phe Ile
                245                 250                 255

Lys Arg Trp Leu Asn Asn Met Pro Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
```

```
    290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Gly Glu Val Ile Pro
                325                 330                 335

Val Ala His Pro Ser Val Glu Lys Ile His Ile Thr Asn His Arg Gly
            340                 345                 350

Phe Ile Lys Asp Ser Ile Ala Thr Trp Met Val Pro Ala Leu Val Ser
        355                 360                 365

Glu Lys Gln Glu Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Ile Asp Pro Gln Leu Asn Ile Ser Phe Thr Tyr Gly Pro Val Ile Leu
            420                 425                 430

Asn Gly Asp Gly Met Asp Tyr Tyr Glu Ser Ser Leu Ser Asp Ser Gly
        435                 440                 445

Trp Leu Thr Ile Pro Pro Lys Asn Gly Thr Val Leu Gly Leu Ile Asn
    450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Tyr Val Tyr Asp Pro Ile Arg Thr
    530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Asp Leu Trp Cys His
                565                 570                 575

Gln Phe Tyr Arg Phe Glu Ala Asp Ile Thr Asn Ser Thr Thr Ser Val
            580                 585                 590

Glu Asn Leu Val Arg Ile Arg Phe Ser Cys Asn Arg Ser Lys Pro
        595                 600                 605


<210> SEQ ID NO 22
<211> LENGTH: 607
<212> TYPE: PRT
<213> ORGANISM: artificial sequence
<220> FEATURE:
<223> OTHER INFORMATION: CAA55672

<400> SEQUENCE: 22

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
        35                  40                  45

Ile Met Thr Leu Leu Ala Ile Thr Gly Val Arg Phe His Gln Val Ser
```

-continued

```
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Ile Gly Ile Arg
145                 150                 155                 160

Lys Ser Ile Ala Ser Ala Ala Asn Pro Ile Leu Leu Ser Ala Leu Ser
                165                 170                 175

Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Lys Thr Ser Glu Ile Thr Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Glu Phe Asp Thr Gln Met Ile Arg Val Phe Glu Ile Gly Phe Ile
                245                 250                 255

Lys Arg Trp Leu Asn Asn Met Pro Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Gly Glu Val Ile Pro
                325                 330                 335

Val Ala His Pro Ser Val Glu Lys Ile His Ile Thr Asn His Arg Gly
            340                 345                 350

Phe Ile Lys Asp Ser Ile Ala Thr Trp Met Val Pro Ala Leu Val Ser
        355                 360                 365

Glu Lys Gln Glu Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Ile Asp Pro Gln Leu Asn Ile Ser Phe Thr Tyr Gly Pro Val Ile Leu
            420                 425                 430

Asn Gly Asp Gly Met Asp Tyr Tyr Glu Ser Ser Leu Ser Asp Ser Gly
        435                 440                 445

Trp Leu Thr Ile Pro Pro Lys Asn Gly Thr Val Leu Gly Leu Ile Asn
    450                 455                 460

Lys Ala Ser Arg Gly Asp Gln Phe Thr Val Ile Pro His Val Leu Thr
465                 470                 475                 480
```

Phe Ala Pro Arg Glu Ser Ser Gly Asn Cys Tyr Leu Pro Ile Gln Thr
485 490 495

Ser Gln Ile Met Asp Lys Asp Val Leu Thr Glu Ser Asn Leu Val Val
500 505 510

Leu Pro Thr Gln Asn Phe Arg Tyr Val Ile Ala Thr Tyr Asp Ile Ser
515 520 525

Arg Gly Asp His Ala Ile Val Tyr Tyr Val Tyr Asp Pro Ile Arg Thr
530 535 540

Ile Ser Tyr Thr Tyr Pro Phe Arg Leu Thr Thr Lys Gly Arg Pro Asp
545 550 555 560

Phe Leu Arg Ile Glu Cys Phe Val Trp Asp Asp Asp Leu Trp Cys His
565 570 575

Gln Phe Tyr Arg Phe Glu Ala Asp Ile Thr Asn Ser Thr Thr Ser Val
580 585 590

Glu Asn Leu Val Arg Ile Arg Phe Ser Cys Asn Arg Ser Lys Pro
595 600 605

<210> SEQ ID NO 23
<211> LENGTH: 607
<212> TYPE: PRT
<213> ORGANISM: artificial sequence
<220> FEATURE:
<223> OTHER INFORMATION: AAQ96308

<400> SEQUENCE: 23

Met Leu Ser Tyr Gln Asp Lys Val Gly Ala Phe Tyr Lys Asp Asn Ala
1 5 10 15

Arg Ala Asn Ser Ser Lys Leu Ser Leu Val Thr Glu Glu Gln Gly Gly
20 25 30

Arg Arg Pro Pro Tyr Leu Leu Phe Val Leu Leu Ile Leu Leu Val Gly
35 40 45

Ile Met Thr Leu Leu Ala Ile Thr Gly Val Arg Phe His Gln Val Ser
50 55 60

Thr Ser Asn Met Glu Phe Ser Arg Leu Leu Lys Glu Asp Met Glu Lys
65 70 75 80

Ser Glu Ala Val His His Gln Val Ile Asp Val Leu Thr Pro Leu Phe
85 90 95

Lys Ile Ile Gly Asp Glu Val Gly Leu Gln Leu Pro Gln Lys Leu Asn
100 105 110

Glu Ile Lys Gln Phe Ile Leu Gln Lys Thr Asn Phe Phe Asn Pro Asn
115 120 125

Arg Glu Phe Asp Phe Arg Asp Leu His Trp Cys Ile Asn Pro Pro Ser
130 135 140

Lys Ile Lys Val Asn Phe Thr Asn Tyr Cys Asp Thr Ile Gly Ile Lys
145 150 155 160

Lys Ser Ile Ala Ser Ala Ala Asn Pro Ile Leu Leu Ser Ala Leu Ser
165 170 175

Gly Gly Arg Gly Asp Ile Phe Pro Pro Tyr Arg Cys Ser Gly Ala Thr
180 185 190

Thr Ser Val Gly Arg Val Phe Pro Leu Ser Val Ser Leu Ser Met Ser
195 200 205

Leu Ile Ser Lys Thr Ser Glu Ile Thr Ser Met Leu Thr Ala Ile Ser
210 215 220

Asp Gly Val Tyr Gly Lys Thr Tyr Leu Leu Val Pro Asp Tyr Ile Glu
225 230 235 240

```
Gly Glu Phe Asp Thr Gln Lys Ile Arg Val Phe Glu Ile Gly Phe Ile
                245                 250                 255

Lys Arg Trp Leu Asn Asn Met Pro Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Glu Glu Val Ile Pro
                325                 330                 335

Val Ala His Pro Ser Val Glu Lys Ile His Ile Thr Asn His Arg Gly
            340                 345                 350

Phe Ile Lys Asp Ser Ile Ala Thr Trp Met Val Pro Ala Leu Val Ser
        355                 360                 365

Glu Lys Gln Glu Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Ile Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Ser Asp Ser Gly
        435                 440                 445

Trp Leu Thr Ile Pro Pro Arg Asn Gly Thr Val Leu Gly Leu Ile Asn
    450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Tyr Val Tyr Asp Pro Ile Arg Thr
    530                 535                 540

Ile Ser Tyr Thr His Pro Phe Arg Leu Thr Thr Lys Gly Arg Pro Asp
545                 550                 555                 560

Phe Leu Arg Ile Glu Cys Phe Val Trp Asp Asp Asp Leu Trp Cys His
                565                 570                 575

Gln Phe Tyr Arg Phe Glu Ala Asp Ile Thr Asn Ser Thr Thr Ser Val
            580                 585                 590

Glu Asn Leu Val Arg Ile Arg Phe Ser Cys Asn Arg Ser Lys Pro
        595                 600                 605
```

<210> SEQ ID NO 24
<211> LENGTH: 607
<212> TYPE: PRT
<213> ORGANISM: artificial sequence
<220> FEATURE:
<223> OTHER INFORMATION: ABF55671
<220> FEATURE:
<221> NAME/KEY: misc_feature
<222> LOCATION: (53)..(53)
<223> OTHER INFORMATION: Xaa can be any naturally occurring amino acid

<400> SEQUENCE: 24

```
Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
        35                  40                  45

Val Met Thr Leu Xaa Ala Ile Thr Gly Val Arg Ile His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Val Gly Ile Arg
145                 150                 155                 160

Lys Ser Ile Ala Ser Ala Ala Asn Pro Ile Leu Leu Ser Ala Leu Ser
                165                 170                 175

Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Lys Thr Ser Glu Ile Thr Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Glu Phe Asp Thr Gln Lys Ile Arg Val Phe Glu Ile Gly Phe Ile
                245                 250                 255

Arg Arg Trp Leu Asn Asn Met Pro Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Glu Glu Val Ile Pro
                325                 330                 335

Val Ala His Pro Ser Val Glu Lys Ile His Ile Thr Asn His Arg Gly
            340                 345                 350

Phe Ile Lys Asp Ala Ile Ala Thr Trp Met Val Pro Ala Leu Val Ser
        355                 360                 365

Glu Lys Gln Glu Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400
```

```
Gly Gln Leu Pro Ser Tyr Gly Arg Leu Thr Leu Pro Leu Asp Pro Ser
                405                 410                 415

Ile Asp Leu Gln Leu Asn Ile Ser Phe Thr Tyr Gly Pro Val Ile Leu
            420                 425                 430

Asn Gly Asp Gly Met Asp Tyr Tyr Glu Ser Ser Leu Ser Asp Ser Gly
        435                 440                 445

Trp Leu Thr Ile Pro Pro Lys Asn Gly Thr Val Leu Gly Leu Ile Asn
    450                 455                 460

Lys Ala Ser Arg Gly Asp Gln Phe Thr Val Thr Pro His Val Leu Thr
465                 470                 475                 480

Ser Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Tyr Val Tyr Asp Pro Ile Arg Thr
    530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Asp Met Trp Cys His
                565                 570                 575

Gln Phe Tyr Arg Phe Glu Ala Asp Ile Thr Asn Ser Thr Thr Ser Val
            580                 585                 590

Glu Asn Leu Val Arg Ile Arg Phe Ser Cys Asn Arg Ser Lys Pro
        595                 600                 605


<210> SEQ ID NO 25
<211> LENGTH: 607
<212> TYPE: PRT
<213> ORGANISM: artificial sequence
<220> FEATURE:
<223> OTHER INFORMATION: ACS88240

<400> SEQUENCE: 25

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
        35                  40                  45

Ile Met Thr Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Ile Gly Ile Arg
145                 150                 155                 160
```

```
Gln Ser Ile Ala Ser Ala Ala Asn Pro Ile Leu Leu Ser Ala Leu Ser
                165                 170                 175

Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Val Ile Ser Lys Thr Ser Glu Ile Thr Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Glu Phe Asp Thr Gln Lys Ile Arg Val Phe Glu Ile Gly Phe Ile
                245                 250                 255

Lys Arg Trp Leu Asn Asn Met Pro Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Asn Thr Val Leu Leu
    290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Glu Glu Val Ile Pro
                325                 330                 335

Val Ala His Pro Ser Ile Glu Lys Ile His Ile Thr Asn His Arg Gly
            340                 345                 350

Phe Ile Lys Asp Ser Ile Ala Thr Trp Met Val Pro Ala Leu Val Ser
        355                 360                 365

Glu Lys Gln Glu Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Arg Gln Leu Pro Ser Tyr Gly Arg Leu Thr Leu Pro Leu Asp Pro Ser
                405                 410                 415

Met Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Pro Asp Ser Gly
        435                 440                 445

Trp Leu Thr Ile Pro Pro Lys Asn Gly Thr Val Leu Gly Leu Ile Asn
    450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Tyr Val Tyr Asp Pro Ile Arg Thr
    530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Asp Leu Trp Cys His
                565                 570                 575
```

```
Gln Phe Tyr Arg Phe Glu Ala Asp Ile Thr Asn Ser Thr Thr Ser Val
            580                 585                 590

Glu Asn Leu Val Cys Ile Arg Phe Ser Cys Asn Arg Ser Lys Pro
        595                 600                 605


<210> SEQ ID NO 26
<211> LENGTH: 607
<212> TYPE: PRT
<213> ORGANISM: artificial sequence
<220> FEATURE:
<223> OTHER INFORMATION: ABK35770

<400> SEQUENCE: 26

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
        35                  40                  45

Ile Met Thr Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Ile Gly Ile Arg
145                 150                 155                 160

Lys Ser Ile Ala Ser Ala Ala Asn Pro Ile Leu Leu Ser Ala Leu Ser
                165                 170                 175

Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Lys Thr Ser Gly Ile Thr Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Glu Phe Asp Thr Gln Lys Ile Arg Val Phe Glu Ile Gly Phe Ile
                245                 250                 255

Lys Arg Trp Leu Asn Asn Met Pro Leu Phe Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300

Tyr His Asp Ser Asn Gly Ser Gln Gly Gly Val Leu Val Val Thr Leu
305                 310                 315                 320

Gly Ile Phe Gly Ala Thr Pro Met Asp Gln Val Glu Glu Met Ile Pro
                325                 330                 335
```

-continued

```
Val Ala His Pro Ser Val Glu Lys Ile His Ile Thr Asn His Arg Gly
            340                 345                 350

Phe Ile Lys Asp Ser Ile Ala Thr Trp Met Val Pro Val Leu Val Ser
        355                 360                 365

Glu Lys Gln Glu Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Ile Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Asp Ser Gly
        435                 440                 445

Trp Leu Thr Ile Pro Pro Lys Asn Gly Thr Val Leu Gly Leu Ile Asn
    450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Tyr Val Tyr Asp Pro Ile Arg Thr
    530                 535                 540

Ile Ser Tyr Thr Tyr Pro Phe Arg Leu Thr Thr Lys Gly Arg Pro Glu
545                 550                 555                 560

Phe Leu Arg Ile Glu Cys Phe Val Trp Asp Asp Asp Leu Trp Cys His
                565                 570                 575

Gln Phe Tyr Arg Phe Glu Ala Asp Ile Thr Asn Ser Thr Ile Ser Val
            580                 585                 590

Glu Asn Leu Val His Ile Arg Phe Ser Cys Asn Arg Ser Lys Pro
        595                 600                 605


<210> SEQ ID NO 27
<211> LENGTH: 607
<212> TYPE: PRT
<213> ORGANISM: artificial sequence
<220> FEATURE:
<223> OTHER INFORMATION: ACD92997

<400> SEQUENCE: 27

Met Leu Ser Tyr Gln Asp Lys Val Gly Ala Phe Tyr Lys Asp Asn Ala
1               5                   10                  15

Arg Ala Asn Ser Ser Lys Leu Ser Ser Val Thr Glu Glu Gln Gly Gly
            20                  25                  30

Arg Arg Pro Pro Tyr Leu Leu Phe Val Leu Leu Ile Leu Leu Val Gly
        35                  40                  45

Ile Met Ala Leu Leu Ala Ile Thr Gly Val Arg Phe His Gln Val Ser
    50                  55                  60

Thr Asn Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95
```

```
Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Ile Glu Ile Arg
145                 150                 155                 160

Lys Ser Ile Ala Leu Ala Ala Asn Pro Ile Leu Leu Ser Ala Leu Ser
                165                 170                 175

Gly Gly Arg Gly Asp Ile Phe Pro Pro Tyr Ser Cys Ser Gly Ala Thr
            180                 185                 190

Thr Ser Val Gly Arg Val Phe Pro Leu Ser Val Ser Leu Ser Met Ser
        195                 200                 205

Leu Ile Ser Lys Thr Ser Glu Ile Ile Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Gly Phe Asp Thr Gln Lys Ile Arg Val Phe Glu Ile Gly Phe Ile
                245                 250                 255

Lys Arg Trp Leu Asn Asp Met Pro Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300

Tyr His Asp Ser Asp Gly Ser Gln Asp Gly Ile Leu Val Val Thr Leu
305                 310                 315                 320

Gly Ile Phe Gly Ala Thr Pro Met Asp Gln Val Glu Glu Val Ile Pro
                325                 330                 335

Val Ala His Pro Ser Val Glu Lys Ile His Ile Thr Asn His Arg Gly
            340                 345                 350

Phe Ile Lys Asp Ser Ile Ala Thr Trp Met Val Pro Ala Leu Val Ser
        355                 360                 365

Glu Lys Gln Glu Glu Gln Lys Asn Cys Leu Glu Ser Ala Cys Gln Arg
    370                 375                 380

Lys Ser Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Ile Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Asp Ser Gly
        435                 440                 445

Trp Leu Thr Ile Pro Pro Lys Asn Gly Thr Val Leu Gly Leu Ile Asn
    450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
```

-continued

```
        515                 520                 525

Arg Gly Asp His Ala Ile Val Tyr Tyr Val Tyr Asp Pro Ile Arg Ala
    530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Asp Leu Trp Cys His
                565                 570                 575

Gln Phe Tyr Arg Phe Glu Ala Asp Ser Thr Asn Ser Thr Thr Ser Val
            580                 585                 590

Glu Asn Leu Val Arg Ile Arg Phe Ser Cys Asn Arg Ser Lys Pro
        595                 600                 605


<210> SEQ ID NO 28
<211> LENGTH: 607
<212> TYPE: PRT
<213> ORGANISM: artificial sequence
<220> FEATURE:
<223> OTHER INFORMATION: ACI28389

<400> SEQUENCE: 28

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
        35                  40                  45

Ile Met Thr Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Ile Glu Ile Arg
145                 150                 155                 160

Lys Ser Ile Ala Ser Ala Ala Asn Pro Ile Leu Leu Ser Ala Leu Ser
                165                 170                 175

Gly Gly Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Arg Thr Ser Glu Ile Thr Asn Met Leu Thr Ala Ile Ser
    210                 215                 220

Asp Gly Val Tyr Gly Lys Thr Tyr Leu Leu Val Pro Asp Tyr Phe Glu
225                 230                 235                 240

Gly Glu Phe Asp Thr Gln Lys Ile Arg Val Phe Glu Ile Gly Phe Ile
                245                 250                 255

Lys Arg Trp Leu Asn Asp Met Pro Leu Leu Gln Thr Thr Asn Tyr Met
            260                 265                 270

Phe Leu Pro Glu Asn Ser Lys Ala Lys Val Cys Thr Ile Ala Val Gly
```

```
        275                 280                 285

Glu Leu Thr Leu Ala Ser Leu Cys Val Asp Glu Ser Thr Val Ser Leu
    290                 295                 300

Tyr His Asp Gly Ser Gly Ser Gln Asp Gly Ile Leu Val Val Thr Leu
305                 310                 315                 320

Gly Ile Phe Gly Ala Thr Pro Met Asp Gln Val Glu Glu Val Ile Pro
                325                 330                 335

Val Ala His Pro Ser Val Glu Lys Ile His Ile Thr Asn His Arg Gly
            340                 345                 350

Phe Ile Lys Asp Ser Ile Ala Thr Trp Met Val Pro Ala Leu Val Ser
        355                 360                 365

Glu Lys Gln Glu Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Trp Thr Leu Pro Leu Asp Pro Ser
                405                 410                 415

Ile Asp Leu Gln Leu Asn Ile Ser Val Thr Tyr Gly Pro Val Ile Leu
            420                 425                 430

Asn Gly Asp Gly Met Asp Tyr Tyr Glu Ser Pro Leu Ser Asp Ser Gly
        435                 440                 445

Trp Leu Thr Ile Pro Pro Lys Asn Gly Thr Ile Leu Gly Leu Ile Asn
    450                 455                 460

Lys Ala Ser Arg Gly Asp Gln Phe Thr Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Tyr Val Tyr Asp Pro Ile Arg Thr
    530                 535                 540

Ile Ser Tyr Thr Tyr Pro Phe Arg Leu Thr Thr Lys Gly Arg Pro Val
545                 550                 555                 560

Ser Leu Arg Ile Glu Cys Phe Val Trp Asp Asp Asp Leu Trp Cys His
                565                 570                 575

Gln Phe Tyr Gln Phe Glu Ala Asp Ile Thr Asn Ser Thr Thr Ser Val
            580                 585                 590

Glu Asn Leu Val Arg Ile Arg Phe Ser Cys Asn Arg Ser Lys Pro
        595                 600                 605


<210> SEQ ID NO 29
<211> LENGTH: 607
<212> TYPE: PRT
<213> ORGANISM: artificial sequence
<220> FEATURE:
<223> OTHER INFORMATION: ACI28390

<400> SEQUENCE: 29

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
```

-continued

```
        35                  40                  45

Ile Met Thr Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Met Asp Val Leu Thr Pro Leu Phe
                85                  90                  95

Lys Ile Ile Gly Asp Glu Val Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Ser Asn Tyr Cys Asp Thr Ile Gly Ile Arg
145                 150                 155                 160

Lys Ser Ile Ala Ser Ala Ala Asn Pro Ile Leu Leu Ser Ala Leu Ser
                165                 170                 175

Gly Gly Arg Gly Asp Ile Phe Pro Pro Tyr Arg Cys Asn Gly Ala Ala
            180                 185                 190

Thr Ser Ile Gly Arg Val Phe Pro Leu Ser Val Ser Leu Ser Met Ser
        195                 200                 205

Leu Ile Ser Arg Thr Ala Glu Ile Ile Asn Met Leu Thr Ala Ile Ser
    210                 215                 220

Asp Gly Val Asp Gly Lys Thr Tyr Leu Leu Val Pro Asp Tyr Ile Glu
225                 230                 235                 240

Gly Glu Phe Glu Thr Gln Lys Ile Arg Val Phe Glu Ile Gly Phe Ile
                245                 250                 255

Lys Arg Trp Leu Asn Asp Met Ser Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300

Tyr His Asp Ser Asn Gly Ser Gln Asp Gly Ile Leu Val Val Thr Leu
305                 310                 315                 320

Gly Ile Phe Trp Gly Thr Pro Met Asp Gln Val Glu Glu Val Ile Pro
                325                 330                 335

Val Ala His Pro Ser Val Glu Lys Ile His Ile Thr Asn His Arg Gly
            340                 345                 350

Phe Ile Lys Asp Ser Lys Ala Ile Trp Met Val Pro Ala Leu Val Ser
        355                 360                 365

Glu Lys Gln Glu Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Ile Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Asp Ser Gly
        435                 440                 445

Trp Leu Thr Ile Pro Pro Lys Asn Gly Thr Val Leu Gly Leu Met Asn
    450                 455                 460
```

```
Lys Ala Ser Arg Gly Asp Gln Phe Thr Val Ile Pro His Val Leu Thr
465                 470                 475                 480

Phe Ala Pro Arg Glu Ser Gly Gly Asn Cys Tyr Leu Pro Ile Gln Thr
                485                 490                 495

Ser Gln Ile Met Asp Lys Asp Val Leu Ala Glu Ser Asn Leu Val Val
            500                 505                 510

Leu Pro Thr Gln Asn Phe Arg Tyr Val Ile Ala Thr Tyr Asp Ile Ser
        515                 520                 525

Arg Asp Asp His Ala Ile Val Tyr Tyr Val Tyr Asp Pro Ile Arg Thr
    530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Asp Leu Trp Cys His
                565                 570                 575

Gln Phe Tyr Arg Phe Glu Ala Asp Ile Thr Asn Ser Thr Thr Ser Val
            580                 585                 590

Glu Asn Leu Val Arg Ile Arg Phe Ser Cys Asn Arg Ser Lys Pro
        595                 600                 605


<210> SEQ ID NO 30
<211> LENGTH: 607
<212> TYPE: PRT
<213> ORGANISM: artificial sequence
<220> FEATURE:
<223> OTHER INFORMATION: ACN58242

<400> SEQUENCE: 30

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Thr Gly
        35                  40                  45

Ile Leu Ala Leu Leu Ala Ile Thr Arg Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Ile Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Val Gly Val Lys
145                 150                 155                 160

Lys Ser Ile Ala Ser Ala Ala Asn Pro Ile Ile Leu Ser Ala Leu Ser
                165                 170                 175

Gly Ala Arg Gly Asp Ile Phe Pro Pro Cys Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Arg Thr Ser Glu Ile Ile Asn Met Leu Thr Ala Ile Ser
    210                 215                 220
```

```
Asp Gly Met Tyr Gly Lys Thr Tyr Leu Leu Val Pro Asp Tyr Ile Glu
225                 230                 235                 240

Gly Glu Phe Asp Ser Gln Lys Ile Arg Val Phe Glu Ile Gly Phe Ile
                245                 250                 255

Arg Arg Trp Leu Asn Asp Met Pro Leu Leu Gln Thr Thr Asn Tyr Met
            260                 265                 270

Val Leu Pro Glu Thr Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300

Tyr His Asp Ser Asn Gly Ser Gln Asn Gly Ile Leu Val Val Thr Leu
305                 310                 315                 320

Gly Ile Phe Gly Ala Thr Pro Met Asp Gln Val Glu Glu Val Ile Pro
                325                 330                 335

Ile Ala His Pro Ser Val Glu Arg Ile His Ile Thr Asn His Arg Gly
            340                 345                 350

Phe Ile Lys Asp Ser Ile Val Thr Trp Met Val Pro Val Leu Val Ser
        355                 360                 365

Glu Lys Gln Glu Glu Gln Lys Asn Cys Leu Glu Ser Ala Cys Gln Arg
    370                 375                 380

Lys Thr Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Ile Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Asp Ser Gly
        435                 440                 445

Trp Leu Thr Ile Pro Pro Lys Asn Gly Thr Val Leu Gly Leu Ile Asn
    450                 455                 460

Lys Ala Ser Arg Gly Asp Gln Phe Thr Val Thr Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Tyr Val Tyr Asp Pro Ile Arg Thr
    530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Asp Leu Trp Cys His
                565                 570                 575

Gln Phe Tyr Arg Phe Glu Ala Asn Ile Thr Asn Ser Thr Thr Ser Val
            580                 585                 590

Glu Asn Leu Val Arg Ile Arg Phe Ser Cys Asn Arg Ser Lys Pro
        595                 600                 605
```

<210> SEQ ID NO 31
<211> LENGTH: 607
<212> TYPE: PRT
<213> ORGANISM: artificial sequence
<220> FEATURE:

```
<223> OTHER INFORMATION: ABB51156
<220> FEATURE:
<221> NAME/KEY: misc_feature
<222> LOCATION: (343)..(343)
<223> OTHER INFORMATION: Xaa can be any naturally occurring amino acid

<400> SEQUENCE: 31

Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Phe Leu Leu Phe Val Leu Leu Val Leu Leu Val Gly
        35                  40                  45

Ile Met Ala Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80

Ser Glu Ala Val His His Gln Val Ile Asp Val Leu Thr Pro Leu Phe
                85                  90                  95

Lys Ile Ile Gly Asp Glu Ile Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Ile Gly Ile Arg
145                 150                 155                 160

Lys Ser Ile Ala Ser Ala Ala Asn Pro Ile Leu Leu Ser Ala Leu Ser
                165                 170                 175

Gly Gly Arg Gly Asp Ile Phe Pro Pro Tyr Lys Cys Asn Gly Ala Ala
            180                 185                 190

Thr Ser Val Gly Arg Val Phe Pro Leu Ser Val Ser Leu Ser Met Ser
        195                 200                 205

Leu Ile Ser Lys Thr Ser Gly Ile Ile Asn Met Leu Thr Ala Ile Ser
    210                 215                 220

Asp Gly Val Tyr Gly Lys Thr Tyr Leu Leu Met Pro Asp Tyr Ile Glu
225                 230                 235                 240

Gly Glu Phe Asp Thr Gln Lys Ile Arg Val Phe Glu Ile Gly Phe Ile
                245                 250                 255

Lys Arg Trp Leu Asn Asp Met Pro Leu Leu Gln Thr Thr Asn Tyr Ile
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Glu Glu Val Ile Pro
                325                 330                 335

Val Ala His Pro Ser Val Xaa Lys Ile His Ile Thr Asn His Arg Gly
            340                 345                 350

Phe Ile Lys Asp Ser Ile Ala Thr Trp Met Val Pro Ala Leu Ile Ser
        355                 360                 365

Gly Glu Gln Glu Glu Gln Lys Asn Cys Leu Glu Ser Ala Cys Gln Arg
    370                 375                 380
```

Lys Ser Tyr Pro Met Cys Asn Gln Thr Ser Trp Lys Pro Phe Gly Gly
385 390 395 400

Gly Gln Leu Pro Ser Tyr Gly Arg Leu Thr Leu Pro Leu Asp Pro Gly
405 410 415

Ile Asp Leu Gln Leu Asn Ile Ser Phe Thr Tyr Gly Pro Val Ile Leu
420 425 430

Asn Gly Asp Gly Met Asp Tyr Tyr Glu Ser Pro Leu Leu Asp Ser Gly
435 440 445

Trp Leu Thr Ile Pro Pro Lys Asn Gly Thr Ile Leu Gly Leu Ile Asn
450 455 460

Lys Ala Ser Arg Gly Asp Gln Phe Thr Val Ile Pro His Val Leu Thr
465 470 475 480

Phe Ala Pro Arg Glu Ser Ser Gly Asn Cys Tyr Leu Pro Ile Gln Thr
485 490 495

Ser Gln Ile Met Asp Lys Asp Val Leu Thr Glu Ser Asn Leu Val Val
500 505 510

Leu Pro Thr Gln Asn Phe Arg Tyr Val Ile Ala Thr Tyr Asp Ile Ser
515 520 525

Arg Asn Asp His Ala Ile Val Tyr Tyr Val Tyr Asp Pro Ile Arg Thr
530 535 540

Ile Ser Tyr Thr His Pro Phe Arg Leu Thr Thr Lys Gly Arg Pro Asp
545 550 555 560

Phe Leu Arg Ile Glu Cys Phe Val Trp Asp Asp Asp Leu Trp Cys His
565 570 575

Gln Phe Tyr Arg Phe Glu Ala Asp Ile Thr Asn Ser Ala Thr Ser Val
580 585 590

Glu Asn Leu Val Arg Ile Arg Phe Ser Cys Asn Arg Ser Lys Pro
595 600 605

<210> SEQ ID NO 32
<211> LENGTH: 607
<212> TYPE: PRT
<213> ORGANISM: artificial sequence
<220> FEATURE:
<223> OTHER INFORMATION: ABK35780

<400> SEQUENCE: 32

Met Leu Ser Tyr Gln Asp Lys Val Ser Ala Phe Tyr Lys Asp Asn Ala
1 5 10 15

Arg Ala Asn Ser Ser Lys Leu Ser Leu Val Thr Glu Glu His Gly Ser
20 25 30

Arg Arg Pro Pro Tyr Leu Leu Phe Ile Leu Leu Ile Leu Leu Val Gly
35 40 45

Ile Met Ala Leu Leu Ala Ile Thr Gly Ala Arg Phe His Gln Val Ser
50 55 60

Thr Ser Asn Met Glu Phe Ser Arg Leu Leu Lys Glu Asp Met Glu Lys
65 70 75 80

Ser Glu Ala Val His His Gln Val Ile Asp Val Leu Thr Pro Leu Phe
85 90 95

Lys Ile Ile Gly Asp Glu Ile Gly Leu Arg Leu Pro Gln Lys Leu Asn
100 105 110

Glu Ile Lys Gln Phe Ile Leu Gln Lys Thr Asn Phe Phe Asn Pro Lys
115 120 125

Arg Glu Phe Asp Phe Arg Asp Leu His Trp Cys Ile Asn Pro Pro Ser
130 135 140

-continued

```
Lys Ile Lys Val Asn Phe Thr Asn Tyr Cys Asp Thr Ile Gly Ile Arg
145                 150                 155                 160

Lys Ser Ile Ala Leu Ala Ala Asn Pro Ile Leu Leu Ser Ala Leu Ser
                165                 170                 175

Arg Gly Arg Gly Asp Ile Phe Pro Pro Tyr Arg Cys Ser Gly Ala Ala
            180                 185                 190

Thr Ser Val Gly Arg Val Phe Pro Leu Ser Val Ser Leu Ser Met Ser
        195                 200                 205

Leu Ile Ser Arg Thr Ser Glu Ile Ile Asn Met Leu Thr Ala Ile Ser
    210                 215                 220

Asp Gly Val Tyr Gly Lys Thr Tyr Leu Leu Val Pro Asp Tyr Ile Glu
225                 230                 235                 240

Gly Glu Phe Asp Thr Gln Lys Ile Arg Val Phe Glu Ile Gly Phe Ile
                245                 250                 255

Lys Arg Trp Leu Asn Asp Met Pro Leu Leu Gln Thr Thr Asn Tyr Met
            260                 265                 270

Val Leu Pro Glu Asn Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300

Tyr His Asp Ser Asn Gly Ser Gln Asp Gly Ile Leu Val Val Thr Leu
305                 310                 315                 320

Gly Ile Phe Gly Ala Thr Pro Met Asp Gln Val Glu Glu Val Ile Pro
                325                 330                 335

Val Ala His Pro Ser Val Glu Lys Ile His Ile Thr Asn His Arg Gly
            340                 345                 350

Phe Ile Lys Asp Ser Ile Ala Thr Trp Met Val Pro Val Leu Val Ser
        355                 360                 365

Glu Asn Gln Glu Glu Gln Lys Asn Cys Leu Glu Ser Ala Cys Gln Arg
    370                 375                 380

Lys Ser Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Gly
                405                 410                 415

Ile Asp Leu Gln Leu Asn Leu Ser Phe Thr Tyr Gly Pro Ile Ile Leu
            420                 425                 430

Asn Gly Asp Gly Met Asp Tyr Tyr Glu Ser Pro Leu Leu Asn Ser Gly
        435                 440                 445

Trp Leu Thr Ile Pro Pro Lys Asn Gly Thr Ile Leu Gly Leu Ile Asn
    450                 455                 460

Lys Ala Ser Arg Gly Asp Gln Phe Thr Val Thr Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Asp Asp His Ala Ile Val Tyr Tyr Val Tyr Asp Pro Ile Arg Thr
    530                 535                 540

Ile Ser Tyr Thr Tyr Pro Phe Arg Leu Thr Thr Lys Gly Arg Pro Asp
545                 550                 555                 560
```

-continued

Phe Leu Arg Ile Glu Cys Phe Val Trp Asp Tyr Asp Leu Trp Cys His
565 570 575

Gln Phe Tyr Arg Phe Glu Ala Asp Ile Thr Asn Ser Thr Thr Ser Val
580 585 590

Glu Asn Leu Val Arg Ile Arg Phe Ser Cys Asn Arg Ser Lys Pro
595 600 605

<210> SEQ ID NO 33
<211> LENGTH: 607
<212> TYPE: PRT
<213> ORGANISM: artificial sequence
<220> FEATURE:
<223> OTHER INFORMATION: ACJ46470

<400> SEQUENCE: 33

Met Leu Ser Tyr Gln Asp Lys Val Gly Ala Phe Tyr Lys Asp Asn Ala
1 5 10 15

Arg Ala Asn Ser Ser Lys Leu Ser Leu Val Thr Glu Glu Gln Gly Gly
20 25 30

Arg Arg Pro Pro Tyr Leu Phe Phe Val Leu Leu Thr Leu Leu Ile Gly
35 40 45

Ile Leu Ala Leu Leu Ala Ile Thr Gly Val Arg Phe His Gln Val Ser
50 55 60

Thr Ser Asn Met Glu Phe Ser Arg Leu Leu Lys Glu Asp Met Glu Lys
65 70 75 80

Ser Glu Ala Val His His Gln Val Ile Asp Val Leu Thr Pro Leu Phe
85 90 95

Lys Ile Ile Gly Asp Glu Ile Gly Leu Arg Leu Pro Gln Lys Leu Asn
100 105 110

Glu Ile Lys Gln Phe Ile Leu Gln Lys Thr Asn Phe Phe Asn Pro Asn
115 120 125

Arg Glu Phe Asp Phe Arg Asp Leu His Trp Cys Ile Asn Pro Pro Ser
130 135 140

Lys Ile Lys Val Asn Phe Thr Asn Tyr Cys Asp Thr Val Gly Val Lys
145 150 155 160

Lys Ser Ile Thr Ser Ala Ala Asn Pro Ile Ile Leu Ser Ala Leu Ser
165 170 175

Gly Ala Arg Gly Asp Ile Phe Pro Pro Tyr Arg Cys Ser Gly Ala Thr
180 185 190

Thr Ser Val Gly Arg Val Phe Pro Leu Ser Val Ser Leu Ser Met Ser
195 200 205

Leu Ile Ser Arg Thr Ser Glu Ile Ile Asn Met Leu Thr Ala Ile Ser
210 215 220

Asp Gly Val Tyr Gly Lys Thr Tyr Leu Leu Val Pro Asp Tyr Ile Glu
225 230 235 240

Gly Glu Phe Asp Ser Gln Lys Ile Arg Val Phe Glu Ile Gly Phe Ile
245 250 255

Lys Arg Trp Leu Asn Asp Met Pro Leu Leu Gln Thr Thr Asn Tyr Met
260 265 270

Val Leu Pro Glu Thr Ser Lys Ala Lys Val Cys Thr Ile Ala Val Gly
275 280 285

Glu Leu Thr Leu Ala Ser Leu Cys Val Asp Glu Ser Thr Val Leu Leu
290 295 300

Tyr His Asp Ser Asn Gly Ser Gln Asn Gly Ile Leu Val Val Thr Leu
305 310 315 320

```
Gly Ile Phe Gly Ala Thr Ser Met Asp Gln Val Glu Glu Val Ile Pro
                325                 330                 335

Ile Ala His Pro Ser Val Glu Arg Ile His Ile Thr Asn His Arg Gly
            340                 345                 350

Phe Ile Lys Asp Ser Ile Val Thr Trp Met Val Pro Val Leu Val Ser
        355                 360                 365

Glu Lys Gln Glu Glu Gln Lys Asn Cys Leu Glu Ser Ala Cys Gln Arg
    370                 375                 380

Lys Ser Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Ile Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Glu Ser Gly
        435                 440                 445

Trp Leu Thr Ile Pro Pro Lys Asn Gly Thr Val Leu Gly Leu Ile Asn
    450                 455                 460

Lys Ala Ser Arg Gly Asp Gln Phe Thr Ala Thr Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Tyr Val Tyr Asp Pro Ile Arg Thr
    530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Asp Leu Trp Cys His
                565                 570                 575

Gln Phe Tyr Arg Phe Glu Ala Asn Ile Thr Asn Ser Thr Thr Ser Val
            580                 585                 590

Glu Asn Leu Val Arg Ile Arg Phe Ser Cys Asn Arg Ser Lys Pro
        595                 600                 605
```

<210> SEQ ID NO 34
<211> LENGTH: 607
<212> TYPE: PRT
<213> ORGANISM: artificial sequence
<220> FEATURE:
<223> OTHER INFORMATION: ABX84040

<400> SEQUENCE: 34

```
Met Leu Ser Tyr Gln Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Ile Gly
        35                  40                  45

Ile Leu Ala Leu Leu Ala Ile Thr Gly Val Arg Phe His Gln Val Ser
    50                  55                  60

Thr Ser Asn Met Glu Phe Ser Arg Leu Leu Lys Glu Asp Met Glu Lys
65                  70                  75                  80
```

-continued

```
Ser Glu Ala Val His His Gln Val Ile Asp Val Leu Thr Pro Leu Phe
                85                  90                  95

Lys Ile Ile Gly Asp Glu Ile Gly Leu Arg Leu Pro Gln Lys Leu Asn
            100                 105                 110

Glu Ile Lys Gln Phe Ile Leu Gln Lys Thr Asn Phe Phe Asn Pro Asn
        115                 120                 125

Arg Glu Phe Asp Phe Arg Asp Leu His Trp Cys Ile Asn Pro Pro Ser
    130                 135                 140

Lys Ile Lys Val Asn Phe Thr Asn Tyr Cys Asp Thr Val Gly Val Lys
145                 150                 155                 160

Lys Ser Ile Ala Ser Ala Ala Asn Pro Ile Ile Leu Ser Ala Leu Ser
                165                 170                 175

Gly Ala Arg Gly Asp Ile Phe Pro Pro Tyr Arg Cys Ser Gly Ala Thr
            180                 185                 190

Thr Ser Val Gly Arg Val Phe Pro Leu Ser Val Ser Leu Ser Met Ser
        195                 200                 205

Leu Ile Ser Arg Thr Ser Glu Ile Ile Asn Met Leu Thr Ala Ile Ser
    210                 215                 220

Asp Gly Val Tyr Gly Lys Thr Tyr Met Leu Val Pro Asp Tyr Ile Glu
225                 230                 235                 240

Gly Glu Phe Asp Ser Gln Lys Ile Arg Val Phe Glu Ile Gly Phe Ile
                245                 250                 255

Lys Arg Trp Leu Asn Asn Met Pro Leu Leu Gln Thr Thr Asn Tyr Met
            260                 265                 270

Val Leu Pro Glu Thr Ser Lys Ala Lys Val Cys Thr Ile Ala Val Gly
        275                 280                 285

Glu Leu Thr Leu Ala Ser Leu Cys Val Asp Glu Ser Thr Val Leu Leu
    290                 295                 300

Tyr His Asp Ser Asn Gly Ser Gln Asn Gly Ile Leu Val Val Thr Leu
305                 310                 315                 320

Gly Ile Phe Gly Ala Thr Pro Met Asp Gln Val Glu Glu Val Ile Pro
                325                 330                 335

Ile Ala His Pro Ser Val Glu Arg Ile His Ile Thr Asn His Arg Gly
            340                 345                 350

Phe Ile Lys Asp Ser Val Val Thr Trp Met Val Pro Val Leu Val Ser
        355                 360                 365

Glu Lys Gln Glu Glu Gln Lys Asn Cys Leu Glu Ser Ala Cys Gln Arg
    370                 375                 380

Lys Ser Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Val Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Leu Glu Ser Gly
        435                 440                 445

Trp Leu Ala Ile Pro Pro Lys Asn Gly Thr Val Leu Gly Leu Ile Asn
    450                 455                 460

Lys Ala Ser Arg Gly Asp Gln Phe Thr Val Thr Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
```

```
            500                 505                 510

Leu Pro Thr Gln Asn Phe Arg Tyr Val Ile Ala Thr Tyr Asp Ile Ser
        515                 520                 525

Arg Gly Asp His Ala Ile Val Tyr Tyr Val Tyr Asp Pro Ile Arg Thr
    530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Asp Leu Trp Cys His
                565                 570                 575

Gln Phe Tyr Arg Phe Glu Ala Asn Ile Thr Asn Ser Thr Thr Ser Val
            580                 585                 590

Glu Asn Leu Val Arg Ile Arg Phe Ser Cys Asn Arg Ser Lys Pro
        595                 600                 605


<210> SEQ ID NO 35
<211> LENGTH: 1824
<212> TYPE: DNA
<213> ORGANISM: artificial sequence
<220> FEATURE:
<223> OTHER INFORMATION: wildtype DNA encoding CDV HA (AAQ05830)

<400> SEQUENCE: 35

atgctctcct accaagacaa ggtgggtgcc ttctataagg ataatgcaag agctaattca     60

tccaagctgt ccttagtgac agaagagcaa gggggcagga gaccacccta tttgctgttt    120

gtccttctca tccttctggt tggaatcatg accttgcttg ctatcactgg agttcgattt    180

caccaagtat caactagcaa tatggaattt agcagattgc tgaaagagga tatggagaaa    240

tcagaggccg tacatcacca agtcatagat gtcttgacac cgctcttcaa aattattgga    300

gatgaggttg ggttacggtt gccacaaaaa ctaaacgaga tcaaacaatt tatccttcaa    360

aagacaaact tcttcaatcc gaacagggaa ttcgacttcc gcgatctcca ctggtgcatt    420

aatccaccta gtaagatcaa ggtgaatttt actaattact gcgatacaat tgggatcaga    480

aaatctattg catcggcagt aaatcccatc cttttatcag cactctccgg aggcagaggt    540

gacatattcc caccatacag atgcagtgga gctactactt cagtgggcag agttttcccc    600

ctatcagtat cattgtccat gtctttgatc tcaaaaacat cagagataac caatatgcta    660

actgctatct cagacggagt gtatggtaaa acctatttgc tagtgcctga ttacattgaa    720

ggggagttcg acacgcaaaa gattcgagtc tttgagatag ggttcatcaa acggtggctg    780

aataacatgc cattactcca gacaaccaac tacatggtcc tcccggagaa ttccaaagcc    840

aaggtatgta ctatagcagt gggcgagttg acactggctt ccttgtgtgt agatgagagc    900

accgtattgt tatatcatga cagcaatggt tcacaagatg gtattctagt agtgacgctg    960

gggatatttg ggcaacacc tatggatcaa gttgaagaag tgatacctgt cgctcaccca   1020

tcagtagaaa aaatacatat aacaaatcac cgtgggttca taaaagattc aatagcaacc   1080

tggatggtgc ctgcattggt ctctgagaaa caagaggaac aaaaaaattg tctggagtcg   1140

gcttgtcaaa gaaaaaccta ccctatgtgc aaccaaacgt catgggaacc ctttggaggg   1200

ggacagttgc catcttatgg gcggttgaca ttatctctag atccaagcat tgaccttcaa   1260

cttaacatat catttacata cggtccagtt atactgaatg gagacggtat ggattattat   1320

ggaagctcac tttcggactc cggatggctt accattcctc ccaagaatgg aacagtcctt   1380

ggattgataa acaaagcaag tagaggagac cagttcactg taatccccca tgtgttgaca   1440

tttgcgccca gggaatcaag tggaaattgt tatttaccta ttcaaacatc ccagattatg   1500
```

```
gataaagatg tcctgactga gtccaattta gtggtgttgc ctacacagaa ttttagatat   1560

gtcatagcaa catatgatat atctcggggc gatcatgcaa ttgtttatta tgtttatgac   1620

ccaatccgga cgatttctta tacgtaccca tttagactaa ctaccaaggg tagacctgat   1680

ttcctaagaa ttgaatgttt tgtgtgggat gacgatttgt ggtgtcacca attttaccga   1740

tttgaggctg acatcaccaa ctctacaacc agtgttgaga atttagtccg tataagattc   1800

tcatgtgacc gttcaaaacc ttga                                          1824


<210> SEQ ID NO 36
<211> LENGTH: 1824
<212> TYPE: DNA
<213> ORGANISM: artificial sequence
<220> FEATURE:
<223> OTHER INFORMATION: AF478543 encoding CDV HA AAQ05828

<400> SEQUENCE: 36

atgctctcct accaagacaa ggtgggtgcc ttctataagg ataatgcaag agctaattca     60

tccaagctgt ccttagtgac agaagagcaa gggggcagga gaccacccta tttgctgttt    120

gtccttctca tccttctggt tggaatcatg accttgcttg ctatcactgg agttcgattt    180

caccaagtat caactagcaa tatggaattt agcagattgc tgaaagagga tatggagaaa    240

tcagaggccg tacatcacca agtcatagat gtcttgacac cgctcttcaa aattattgga    300

gatgaggttg ggttacggtt gccacaaaaa ctaaacgaga tcaaacaatt tatccttcaa    360

aagacaaact tcttcaatcc gaacagggaa ttcgacttcc gcgatctcca ctggtgcatt    420

aatccaccta gtaagatcaa ggtgaatttt actaattact gcgatacaat tgggatcaga    480

aaatctattg catcggcagt aaatcccatc cttttatcag cactctccgg aggcagaggt    540

gacatattcc caccatacag atgcagtgga gctactactt cagtgggcag agttttcccc    600

ctatcagtat cattgtccat gtctttgatc tcaaaaacat cagagataac caatatgcta    660

actgctatct cagacggagt gtatggtaaa acctatttgc tagtgcctga ttacattgaa    720

ggggagttcg acacgcaaaa gattcgagtc tttgagatag ggttcatcaa acggtggctg    780

aataacatgc cattactcca gacaaccaac tacatggtcc tcccggagaa ttccaaagcc    840

aaggtatgta ctatagcagt gggcgagttg acactggctt ccttgtgtgt agatgagagc    900

accgtattgt tatatcatga cagcaatggt tcacaagatg gtattctagt agtgacgctg    960

gggatatttg gggcaacacc tatggatcaa gttgaagaag tgatacctgt cgctcaccca   1020

tcagtagaaa aaatacatat aacaaatcac cgtgggttca taaaagattc aatagcaacc   1080

tggatggtgc ctgcattggt ctctgagaaa caagaggaac aaaaaaattg tctggagtcg   1140

gcttgtcaaa gaaaaaccta ccctatgtgc aaccaaacgt catgggaacc ctttggaggg   1200

ggacagttgc catcttatgg gcggttgaca ttatctctag atccaagcat tgaccttcaa   1260

cttaacatat catttacata cggtccagtt atactgaatg gagacggtat ggattattat   1320

ggaagctcac tttcggactc cggatggctt accattcctc ccaagaatgg aacagtcctt   1380

ggattgataa acaaagcaag tagaggagac cagttcactg taatccccca tgtgttgaca   1440

tttgcgccca gggaatcaag tggaaattgt tatttaccta ttcaaacatc ccagattatg   1500

gataaagatg tcctgactga gtccaattta gtggtgttgc ctacacagaa ttttagatat   1560

gtcatagcaa catatgatat atctcggggc gatcatgcaa ttgtttatga tgtttatgac   1620

ccaatccgga cgatttctta tacgcaccca tttagactaa ctaccaaggg tagacctgat   1680
```

```
ttcctaagaa ttgaatgttt tgtgtgggat gacgatttgt ggtgtcacca attttaccga   1740

tttgaggctg acatcaccaa ctctacaacc agtgttgaga atttagtccg tataagattc   1800

tcatgtgacc gttcaaaacc ttga                                          1824
```

<210> SEQ ID NO 37
<211> LENGTH: 1824
<212> TYPE: DNA
<213> ORGANISM: artificial sequence
<220> FEATURE:
<223> OTHER INFORMATION: DQ494318 encoding CDV HA ABF55672

<400> SEQUENCE: 37

```
atgctctcct accaagacaa ggtgggtgcc ttctataagg ataatgcaag agctaattca     60

tccaagctgt ccttagtgac agaagagcaa gggggcagga gaccacccta tttgctgttt    120

gtccttctca tccttctggt cggaatcatg accttgcttg ctatcactgg agttcgattt    180

caccaagtat caactagcaa tatggaattt agcagattgt tgaaagagga tatggagaaa    240

tcagaggccg tacatcacca agtcatagat gtcttgacac cgctcttcaa aattattgga    300

gatgaggttg ggttacggtt gccacaaaaa ctaaacgaga tcaaacaatt tatccttcaa    360

aagacaaact tcttcaatcc gaacagggaa ttcgacttcc gcgatctcca ctggtgcatt    420

aatccaccta gtaagatcaa ggtgaatttt actaattact gcgatacaat tgggatcaga    480

aaatctattg catcggcagc aaatcccatc cttttatcag cactctccgg aggcagaggt    540

gacatattcc caccatacag atgcagtgga gctactactt cagtgggcag agttttcccc    600

ctatcagtat cattgtccat gtctttgatc tcaaaaacat cagagataac caatatgcta    660

actgctatct cagacggagt gtatggtaaa acctatttgc tagtgcctga ttacattgaa    720

ggggagttcg acacgcaaat gattcgagtc tttgagatag ggttcatcaa acggtggctg    780

aataacatgc cattactcca gacaaccaac tacatggtcc tcccggagaa ttccaaagcc    840

aaggtatgta ctatagcagt gggcgagttg acactagctt ccttgtgtgt agatgagagc    900

accgtattgt tatatcatga cagcaatggt tcacaagatg gtattctagt agtgacgctg    960

gggatatttg gggcaacacc tatggatcaa gttggagaag tgatacctgt cgctcacccc   1020

tcagtagaaa aaatacatat aacaaatcac cgtgggttca taaaagattc aatagcaacc   1080

tggatggtgc ctgcattggt ctctgagaaa caagaggaac aaaaaaattg tctggagtcg   1140

gcttgtcaaa gaaaaaccta cccaatgtgc aaccaaacgt catgggaacc ctttggaggg   1200

ggacagttac catcttatgg gcggttgaca ttacctctag atccaagcat tgaccctcaa   1260

cttaacatat catttacata cggtccagtt atactgaatg gagacggtat ggattattat   1320

gaaagctcac tttcggactc tggatggctt accattcctc ccaagaacgg aacagtcctt   1380

ggattgataa acaaagcaag tagaggagac cagttcactg taatccccca tgtgttgaca   1440

tttgcgccca gggaatcaag tggaaattgt tatttaccta ttcaaacatc ccagattatg   1500

gataaagatg tcctgactga gtccaattta gtggtgttgc ctacacagaa ttttagatat   1560

gtcatagcaa catatgatat atctcggggc gatcatgcca ttgtttatta tgtttatgac   1620

ccaatccgga cgatttctta tacgtaccca tttagactga ctaccaaggg tagacctgat   1680

ttcctaagaa ttgaatgttt tgtgtgggat gacgatttgt ggtgtcacca attttaccga   1740

tttgaggctg acatcaccaa ctctacaacc agtgttgaga atttagtccg tataagattc   1800

tcatgtaatc gttcaaaacc ttga                                          1824
```

<210> SEQ ID NO 38
<211> LENGTH: 1824
<212> TYPE: DNA
<213> ORGANISM: artificial sequence
<220> FEATURE:
<223> OTHER INFORMATION: AY386316

<400> SEQUENCE: 38

```
atgctctcct accaagacaa ggtgggtgcc ttctataagg ataatgcaag agctaattca     60
tccaagctgt ccttagtgac agaagagcaa gggggcagga gaccacccta tttgctgttt    120
gtccttctca tccttctggt tggaatcatg accttgcttg ctatcactgg agttcgattt    180
caccaagtat caactagcaa tatggaattt agcagattgc tgaaagagga tatggagaaa    240
tcagaggccg tacatcacca agtcatagat gtcttgacac cgctcttcaa aattattgga    300
gatgaggttg ggttacagtt gccacaaaaa ctaaacgaga tcaaacaatt tatccttcaa    360
aagacaaact tcttcaatcc gaacagggaa ttcgacttcc gcgatctcca ctggtgcatt    420
aatccaccta gtaagatcaa ggtgaatttt actaattact gcgatacaat tgggatcaaa    480
aagtctattg catcggcagc aaatcccatc cttttatcag cactctccgg aggcagaggt    540
gacatattcc caccatacag atgcagtgga gctactactt cagtgggcag agttttcccc    600
ctatcagtat cattgtccat gtctttgatc tcaaaaacat cagagataac cagtatgcta    660
actgctatct cagacggagt gtatggtaaa acctatttgc tagtgcctga ttacattgaa    720
ggggagttcg acacgcaaaa gattcgagtc tttgagatag ggttcatcaa acggtggctg    780
aataacatgc cattactcca gacaaccaac tacatggtcc tcccggagaa ttccaaagcc    840
aaggtatgta ctatagcagt gggcgagttg acactggctt ccttgtgtgt agatgagagc    900
accgtattgt tatatcatga cagcaatggt tcacaagatg gtattctagt agtgacgctg    960
gggatatttg gagcaacacc tatggatcaa gttgaagaag tgatacctgt cgctcaccca   1020
tcagtagaaa aaatacatat aacaaatcac cgtgggttca taaaagattc aatagcaacc   1080
tggatggtgc ctgcattggt ctctgagaaa caagaggaac aaaaaaattg tctggagtcg   1140
gcttgtcaaa gaaaaactta ccctatgtgc aaccaaacgt catgggaacc ctttggaggg   1200
ggacagttgc catcttatgg gcggttgaca ttacctctag atccaagcat tgaccttcaa   1260
cttaacatat catttacata cggtccggtt atactgaatg gagacggtat ggattattat   1320
gaaagcccac tttcggactc cggatggctt accattcctc ccaggaacgg aacagtcctt   1380
ggattgataa acaaagcaag tagaggagac cagttcactg taatccccca tgtgttgaca   1440
tttgcgccca gggaatcaag tggaaattgt tatttaccta ttcaaacatc ccagattatg   1500
gataaagatg tccttactga gtccaattta gtggtgttgc ctacacagaa ttttagatat   1560
gtcatagcaa catatgatat atcccggggc gatcatgcaa ttgtttatta tgtttatgac   1620
ccaatccgga cgatttctta tacgcaccca tttagactaa ccaccaaggg tagacctgat   1680
ttcctaagga ttgaatgttt tgtgtgggat gacgatttgt ggtgtcacca attttaccga   1740
tttgaggctg acatcaccaa ctctacaacc agtgttgaga atttagtccg tataagattc   1800
tcatgtaacc gttcaaaacc ttga                                          1824
```

<210> SEQ ID NO 39
<211> LENGTH: 1824
<212> TYPE: DNA
<213> ORGANISM: artificial sequence
<220> FEATURE:
<223> OTHER INFORMATION: DQ494317 encoding CDV HA ABF55671
<220> FEATURE:

<221> NAME/KEY: misc_feature
<222> LOCATION: (158)..(158)
<223> OTHER INFORMATION: n is a, c, g, or t

<400> SEQUENCE: 39

```
atgctctcct accaagacaa ggtgggtgcc ttctataagg ataatgcaag agctaattca      60
tccaagctgt ccttagtgac agaagagcaa gggggcagga gaccacccta tttgctgttt     120
gtccttctca tccttctggt tggagtcatg accttgcntg ctatcactgg agttcgaatt     180
caccaagtat caactagcaa tatggaattt agcagattgc tgaaagagga tatggagaaa     240
tcagaggccg tacatcacca agtcatagat gtcttgacac cgctcttcaa aattattgga     300
gatgaggttg ggttacggtt gccacaaaaa ctaaacgaga tcaaacaatt tatccttcaa     360
aagacaaact tcttcaatcc gaacagggaa ttcgacttcc gcgatctcca ctggtgcatt     420
aatccaccta gtaagatcaa ggtgaatttt actaattact gcgatacagt tgggatcaga     480
aaatctattg catcggcagc aaatcccatc cttttatcag cactctccgg aggcagaggt     540
gacatattcc caccatacag atgcagtgga gctactactt cagtgggcag agtttttcccc     600
ctatcagtat cattgtccat gtctttgatc tcaaaaacat cagagataac caatatgcta     660
actgctatct cagacggagt gtatggtaaa acctatttgc tagtgcctga ttacattgaa     720
ggggagttcg acacgcaaaa gattcgagtc tttgagattg ggttcatcag acggtggctg     780
aataacatgc cattactcca gacaaccaac tacatggtcc tcccggagaa ttccaaagcc     840
aaggtatgta ctatagcagt gggcgagttg acactggctt ccttgtgtgt agatgagagc     900
accgtattgt tatatcatga cagcaatggt tcacaagatg gtattctagt agtgacgctg     960
gggatatttg ggcaacaccc tatggatcaa gttgaagaag tgatacctgt cgctcaccca    1020
tcagtagaaa aaatacatat aacaaatcac cgtgggttca taaaagatgc aatagcaacc    1080
tggatggtgc ctgcattggt ctctgagaaa caagaggaac aaaaaaattg tctggagtcg    1140
gcttgtcaaa gaaaaaccta tcctatgtgc aaccaaacgt catgggaacc ctttggagga    1200
ggacagttgc catcttatgg gcggttgaca ttacctctag atccaagcat tgaccttcaa    1260
cttaacatat catttacata cggtccagtt atactgaatg gagacggtat ggattattat    1320
gaaagctcac tttcggactc cggatggctt accattcctc ccaagaacgg aacagtcctt    1380
ggattgataa acaaagcaag tagaggagac cagttcactg taaccccccca tgtgttgaca    1440
tctgcgccca gggaatcaag tggaaattgt tatttaccta ttcaaacatc ccagattatg    1500
gataaagatg tcctgactga gtccaattta gtggtgttgc ctacacagaa ttttagatat    1560
gtcatagcaa catatgatat atctcggggc gatcatgcaa ttgtttatta tgtttatgac    1620
ccaatccgga cgatttctta tacgtaccca tttagactaa ctaccaaggg tagacctgat    1680
ttcctaagaa ttgaatgttt tgtgtgggat gacgatatgt ggtgtcacca attttaccga    1740
tttgaggctg acatcaccaa ctctacaacc agtgttgaga atttagtccg tataagattc    1800
tcatgtaacc gttcaaaacc ttga                                           1824
```

<210> SEQ ID NO 40
<211> LENGTH: 1824
<212> TYPE: DNA
<213> ORGANISM: artificial sequence
<220> FEATURE:
<223> OTHER INFORMATION: GQ214376 encoding CDV HA ACS88240

<400> SEQUENCE: 40

```
atgctctcct accaagacaa ggtgggtgcc ttctataagg ataatgcaag agctaattca      60
```

```
tccaagctgt ccttagtgac agaagagcaa gggggcagga gaccacccta tttgctgttt    120

gtccttctca tccttctggt tggaatcatg accttgcttg ctatcactgg agttcgattt    180

caccaagtat caactagcaa tatggaattt agcagattgc tgaaagagga tatggagaaa    240

tcagaggccg tacatcacca agtcatagat gtcttgacac cgctcttcaa aattattgga    300

gatgaggttg ggttacggtt gccacaaaaa ctaaacgaga tcaaacaatt tatccttcaa    360

aagacaaact tcttcaatcc gaacagggaa ttcgacttcc gcgatctcca ctggtgcatt    420

aatccaccta gtaagatcaa ggtgaatttt actaattact gcgatacaat tgggatcaga    480

caatctattg catcggcagc aaatcccatc cttttatcag cactctccgg aggcagaggt    540

gacatattcc caccatacag atgcagtgga gctactactt cagtgggcag agtttcccc     600

ctgtcagtat cattgtccat gtctgtgatc tcaaaaacat cagagataac caatatgcta    660

actgctatct cagacggagt gtatggtaaa acctatttgc tagtgcctga ttacattgaa    720

ggggagttcg acacgcaaaa gattcgagtc tttgagatag ggttcatcaa acggtggctg    780

aataacatgc cattactcca gacaaccaac tatatggtcc tcccggagaa ttccaaagcc    840

aaggtatgta ctatagcagt gggcgagttg acactggctt ccttgtgtgt agatgagaac    900

accgtattgt tatatcatga cagcaatggt tcacaagatg gtattctagt agtgacgctg    960

gggatatttg gggcaacacc tatggatcaa gttgaagaag tgatacctgt cgcccaccca   1020

tcaatagaaa aaatacatat aacaaatcac cgtgggttca taaaagattc aatagcaacc   1080

tggatggtgc ctgcattggt ctctgagaaa caagaggaac aaaaaaattg tctggagtcg   1140

gcttgtcaaa gaaaaaccta ccctatgtgc aaccaaacgt catgggaacc ctttggaggg   1200

agacagttgc catcttatgg gcggttgaca ttacctctag atccaagtat ggaccttcaa   1260

cttaacatat catttacata cggtccagtt atactgaatg gagacggtat ggattattat   1320

gaaagcccac ttccggactc cggatggctt accattccac ccaagaacgg aacagtcctt   1380

ggactgataa acaaagcaag tagaggagac cagttcactg taatccccca tgtgttgaca   1440

tttgcgccca gggaatcaag tggaaattgt tatttaccta ttcaaacatc ccagattatg   1500

gataaagatg tccttactga gtccaattta gtggtgttgc ctacacagaa ttttagatat   1560

gtcatagcaa catatgatat atcccggggt gatcatgcaa ttgtttatta tgtttatgac   1620

ccaatccgga cgatttctta tacgtaccca tttagactaa ctaccaaggg tagacctgat   1680

ttcctaagga ttgaatgttt tgtgtgggat gacgatttgt ggtgtcacca attttatcga   1740

tttgaggctg acatcaccaa ctctacaacc agtgttgaga atttagtctg tataagattc   1800

tcatgtaacc gttcaaaacc ttga                                          1824
```

<210> SEQ ID NO 41
<211> LENGTH: 1824
<212> TYPE: DNA
<213> ORGANISM: artificial sequence
<220> FEATURE:
<223> OTHER INFORMATION: DQ889177 encoding CDV HA ABK35770

<400> SEQUENCE: 41

```
atgctctcct accaagacaa ggtgggtgcc ttctataagg ataatgcaag agctaattca     60

tccaagctgt ccttagtgac agaagagcaa gggggcagga gaccacccta tttgctgttt    120

gtccttctca tccttctggt tggaatcatg accttgcttg ctatcactgg agttcgattt    180

caccaagtat caactagcaa tatggaattt agcagattac tgaaagagga tatggagaaa    240
```

-continued

```
tcagaggccg tacatcacca agtcatagat gtcttgacac cgctcttcaa aattattgga    300

gatgaggttg ggttacggtt gccacaaaaa ctaaacgaga tcaaacaatt tatccttcaa    360

aagacaaact tcttcaatcc gaacagggaa ttcgacttcc gcgatctcca ctggtgcatt    420

aatccaccta gtaagatcaa ggtgaatttt actaattact gcgatacaat tgggatcaga    480

aaatctattg catcggcagc aaatcccatc cttttatcag cactctcggg aggcagaggt    540

gacatattcc caccatacag atgcagtgga gctactactt cagtgggcag agttttcccc    600

ctatcagtat cattgtccat gtctttgatt tcaaaaacat cagggataac caatatgcta    660

actgccatct cagacggagt gtatggtaaa acctatttgc tagtgcctga ttacattgaa    720

ggggagttcg acacgcaaaa gattcgagtc tttgagatag ggttcattaa acggtggctg    780

aataacatgc cattattcca gacaaccaac tacatggtcc tcccggagaa ttccaaagcc    840

aaggtatgta ctatagcagt gggcgaattg acactagctt ccttgtgtgt agatgagagc    900

accgtattgt tatatcatga tagcaatggt tcacaaggtg gtgttctagt agtgacgctg    960

gggatatttg ggcaacacc tatggatcaa gttgaagaaa tgatacctgt cgctcaccca   1020

tcagtagaaa aaatacatat aacaaatcac cgtgggttca taaaagattc aatagcaacc   1080

tggatggtgc ctgtattggt ctctgagaaa caagaggaac aaaaaaattg tctggagtcg   1140

gcttgtcaaa gaaaaaccta ccctatgtgc aaccaaacgt catgggaacc ctttggaggg   1200

ggacagttgc catcttatgg gcggttgaca ttacctctag atccgagcat tgaccttcaa   1260

cttaacatat catttacata cggtccagtt atactgaatg gagacggtat ggattactat   1320

gaaagcccac ttttggactc tgggtggctt accattcctc ccaagaacgg aacagtcctt   1380

ggattgataa acaaagcaag tagaggagac cagttcactg taatccccca tgtgttaaca   1440

tttgcgccca gggaatcaag tggaaattgt tatttaccta ttcaaacatc ccagattatg   1500

gataaagatg tccttactga gtccaattta gtggtgttgc ctacacagaa ttttagatat   1560

gtcatagcaa catatgatat atcccggggc gatcatgcaa ttgtttatta tgtttatgac   1620

ccaatccgga cgatatccta tacgtaccca tttagactaa ctaccaaggg tagacctgaa   1680

ttcctaagga ttgaatgttt tgtgtgggat gacgatttgt ggtgtcacca attttaccga   1740

tttgaggctg acatcaccaa ctctacaatc agtgttgaga atttagtcca tataagattc   1800

tcatgtaacc gttcaaaacc ttga                                           1824
```

<210> SEQ ID NO 42
<211> LENGTH: 1824
<212> TYPE: DNA
<213> ORGANISM: artificial sequence
<220> FEATURE:
<223> OTHER INFORMATION: EU716337 encoding CDV HA ACD92997

<400> SEQUENCE: 42

```
atgctctcct accaagacaa ggtgggtgcc ttctataagg ataatgcaag agctaattca     60

tccaagctgt cctcagtgac agaagagcaa gggggcagga gaccacccta tttgctgttt    120

gtccttctca tcctactggt tggaatcatg gccttgcttg ctatcactgg agttcgattt    180

caccaagtat caactaacaa tatggaattt agcagattgc tgaaagagga tatggagaag    240

tcagaggccg tacatcacca agtcatagat gtcttgacac cgctcttcaa gattattgga    300

gatgaggttg ggttacggtt gccacaaaaa ctaaacgaga tcaaacaatt tatccttcaa    360

aagacaaact tcttcaatcc gaacagggag ttcgatttcc gcgatctcca ctggtgcatt    420

aacccaccta gtaagatcaa agtgaatttt actaattact gcgatacaat tgagatcaga    480
```

```
aaatctattg cattggcagc aaatcccatc cttttatcag cactctccgg tggcagaggt    540
gacatattcc caccatacag ttgcagtgga gctactactt cagtaggcag agttttccct    600
ctatcagtat cattgtccat gtctttgatc tcaaaaacat cagagataat caatatgcta    660
accgctatct cagacggggt gtatggtaaa acttatttgc tagttcctga ttatattgaa    720
gggggttcg acacgcaaaa gattcgagtc tttgagatag ggttcatcaa acggtggctg    780
aatgacatgc cattactcca gacaaccaac tatatggtcc tcccggagaa ttccaaagcc    840
aaggtatgta ctatagcggt gggcgagttg acactggctt ccttgtgtgt agatgagagc    900
accgtattgt tatatcatga cagcgatggt tcacaagatg gtattctagt ggtgacgctg    960
ggaatatttg gggcaacacc tatggatcaa gttgaagagg tgatacctgt tgctcaccca   1020
tcagtagaaa aaatacatat aacaaatcac cgtgggttca taaaagattc aatagcaacc   1080
tggatggtgc ctgcattggt atctgagaaa caagaggaac aaaaaaattg tctggagtcg   1140
gcttgtcaaa gaaaatccta ccctatgtgc aaccaaacgt catgggaacc ctttggagga   1200
ggacagttgc catcttatgg gcggttgaca ttacctctag atccaagcat tgaccttcaa   1260
cttaacatct cgtttacata cggtccggtt atactgaatg gagacggtat ggattattat   1320
gaaagcccac ttttggactc cggatggctt accattcccc ccaagaacgg aacagtcctt   1380
ggattgataa acaaagcaag tagaggagac caattcactg taatccccca tgtgttgaca   1440
tttgcgccca gggaatcaag tggaaattgt tatttaccta ttcaaacatc ccagattatg   1500
gataaagatg tccttactga gtccaattta gtggtgttgc ctacacagaa ttttagatat   1560
gtcatagcaa catatgatat atcccggggc gatcatgcga ttgtttatta tgtttatgac   1620
ccaatccggg cgatttctta tacgtaccca tttagactaa ctaccaaggg tagacctgat   1680
ttcctaagga ttgaatgttt tgtgtgggat gacgatttgt ggtgtcacca attttaccga   1740
ttcgaggctg acagcaccaa ctctacaacc agtgttgaga atttagtccg tataagattc   1800
tcatgtaatc gttcaaaacc ttga                                          1824
```

<210> SEQ ID NO 43
<211> LENGTH: 1821
<212> TYPE: DNA
<213> ORGANISM: artificial sequence
<220> FEATURE:
<223> OTHER INFORMATION: FJ011004 encoding CDV HA ACI28389

<400> SEQUENCE: 43

```
atgctctcct accaagacaa ggtgggtgcc ttctataagg ataatgcaag agctaattca     60
tccaagctgt ccttagtgac agaagagcaa gggggccgga gaccacccta tttgctgttt    120
gtccttctca tccttctggt tggaatcatg accttgcttg ctatcactgg agttcgattt    180
caccaagtat caactagcaa tatggaattt agcagattgc tgaaagagga tatggagaaa    240
tcagaggccg tacatcacca agtcatagat gtcttgacac cgctcttcaa aattattgga    300
gatgaggttg ggttacggtt gccacagaaa ctaaacgaga tcaagcaatt tatccttcaa    360
aagacaaact tcttcaatcc gaacagggaa ttcgacttcc gcgatctcca ctggtgcatt    420
aatccaccta gtaagatcaa ggtgaatttt actaattact gtgatacaat tgagatcaga    480
aaatctattg catcggcagc aaatcccatc cttttatcag cactctccgg aggcagaggt    540
gacatattcc caccatacag atgcagtgga gctactactt cagtgggcag agttttcccc    600
ctatcagtat cattgtccat gtctttgatc tcaagaacat cagagataac caatatgcta    660
```

-continued

```
actgctatct cagacggagt gtatggtaaa acctatttgc tagtgcctga ttactttgaa    720

ggggagttcg acacgcaaaa gattcgggtc tttgagatag ggttcatcaa acggtggctg    780

aatgacatgc cattactcca gacaaccaac tacatgttcc tcccggagaa ttccaaagcc    840

aaggtatgta ctatagcagt gggcgagttg acactggctt ccttgtgtgt agatgagagc    900

accgtatcgt tatatcatga cggcagtggt tcacaagatg gtattctagt agtgacgctg    960

gggatatttg gggcaacacc tatggatcaa gttgaagagg tgatacctgt cgctcaccca   1020

tcagtagaga aaatacatat aaccaatcac cgtggattca taaaagattc aatcgcaacc   1080

tggatggtgc ctgcattggt ctctgagaaa caagaggaac aaaaaaattg tctggagtcg   1140

gcttgtcaaa gaaaaaccta ccctatgtgc aaccaaacgt catgggaacc ctttggagga   1200

ggacagttgc catcttatgg gcggtggaca ttacctctag atccaagcat tgaccttcaa   1260

cttaacatat cagttacata cggtccagtt atactgaatg gagacggtat ggattattat   1320

gaaagcccac tttcagactc cggatggctt accattcctc ccaagaacgg aacaatcctt   1380

ggattgataa acaaagcaag tagaggagac cagttcactg taatccccca tgtgttgaca   1440

tttgcgccca gggaatcaag tggaaattgt tatttaccta ttcaaacatc ccagattatg   1500

gataaagatg tccttactga gtccaattta gtggtgttgc ctacacagaa ttttagatat   1560

gtcatagcaa catatgatat atcccggggc gatcatgcaa ttgtttatta tgtttatgac   1620

ccaatccgga cgatttctta tacttaccca tttagactaa ctaccaaggg tagacctgtt   1680

tccctaagga ttgaatgttt tgtgtgggat gacgatttgt ggtgtcacca attttaccaa   1740

tttgaggcag acatcaccaa ctctaccacc agtgttgaga atttagtccg tataagattc   1800

tcatgtaacc gttcaaaacc t                                             1821
```

<210> SEQ ID NO 44
<211> LENGTH: 1821
<212> TYPE: DNA
<213> ORGANISM: artificial sequence
<220> FEATURE:
<223> OTHER INFORMATION: FJ011005 encoding CDV HA ACI28390

<400> SEQUENCE: 44

```
atgctctcct accaagacaa ggtgggtgcc ttttataagg ataatgcaag agccaattca     60

tccaagctgt ctctagtgac agaagagcaa gggggtagga gaccacccta tctgctgttt    120

gtccttctca tcctactggt tggaatcatg accttgcttg ctatcaccgg agttcgattt    180

caccaggtat caactagcaa tatggaattc agcagattgc tgaaagagga tatggagaaa    240

tcagaggccg tacaccacca agtcatggat gtcttgacac cgctcttcaa aattattgga    300

gatgaggttg ggttacggtt gccacaaaaa ctgaacgaga tcaaacaatt tatccttcaa    360

aagacaaact tcttcaatcc gaacagggaa ttcgacttcc gcgatctcca ctggtgcatt    420

aacccaccta gtaagatcaa ggtgaatttt tctaattact gtgatacaat tgggatcaga    480

aaatctattg catcagcagc aaatcctatc cttttatcag cactctccgg aggcagaggt    540

gacatattcc ctccatacag atgcaatgga gctgctactt caataggcag agttttccct    600

ctatctgtgt cattgtccat gtccttgatc tccagaacag cagagataat caatatgcta    660

accgctatct cagacggagt tgatggtaaa acttacttgc tagtgcctga ttatattgaa    720

ggggagttcg aaacgcagaa gattcgagtc tttgagatcg ggttcatcaa acggtggctg    780

aatgacatgt cattactcca gacaaccaac tatatggtcc tcccggagaa ttccaaagcc    840

aaggtatgta ctatagcagt gggcgagttg acactggctt ccttgtgtgt agatgagagc    900
```

actgtattgt tatatcatga cagcaatggt tcacaagatg gtattctagt agtgacgctg 960
ggaatatttt ggggcacacc tatggatcaa gttgaagagg tgatacctgt cgctcaccca 1020
tcagtagaaa aaatacatat aacaaatcac cgtgggttca taaaagattc aaaagcaatc 1080
tggatggtgc ctgcattggt ctctgagaaa caagaggaac aaaaaaattg tctggagtcg 1140
gcttgtcaaa gaaaaaccta ccctatgtgc aaccaaacgt catgggaacc ctttgggga 1200 ggacaattgc catcctatgg gcggctgaca ttacctctag atccaagtat tgaccttcaa 1260
cttaacatat cgtttacata cggtccggtt atactgaatg gagacggtat ggattattat 1320
gaaagcccac ttttggactc cggatggctt accattcctc ccaaaaacgg aacagttctt 1380
ggattgatga acaaagcaag tagaggagac cagttcactg taatccccca tgtgttgaca 1440
tttgcgccta gggaatcagg tggaaattgt tatttaccta ttcaaacctc ccagattatg 1500
gataaagatg tccttgctga gtccaattta gtggtgttgc ctacacagaa ttttagatat 1560
gtcatagcaa catatgatat atcccgggac gatcatgcga ttgtttatta tgtttatgat 1620
ccaatccgga cgatttctta tacgtaccca tttagactaa ctaccaaggg tagacctgat 1680
ttcctaagaa ttgaatgttt tgtatgggat gacgatttgt ggtgtcatca attttaccga 1740
ttcgaggctg acatcactaa ctctacaacc agtgttgaga atttagtccg tataagattc 1800
tcatgtaacc gttcaaaacc t 1821

<210> SEQ ID NO 45
<211> LENGTH: 1824
<212> TYPE: DNA
<213> ORGANISM: artificial sequence
<220> FEATURE:
<223> OTHER INFORMATION: FJ705233 encoding CDV HA ACN58242

<400> SEQUENCE: 45
atgctctcct accaagacaa ggtgggtgcc ttctataagg ataatgcaag agctaattca 60
tccaagctgt ccttagtgac agaagagcaa gggggaagga gaccacccta tttgctgttt 120
gtccttctca tcctactgac tggaatcctg gccttgcttg ccatcactag agttcgattt 180
caccaagtat caactagcaa tatggaattt agcagattgc tgaaagagga tatggagaaa 240
tcagaggccg tacatcacca agtcatagat gtcttgacgc cgctcttcaa aattattgga 300
gatgagattg ggttacggtt gccacaaaaa ctaaacgaga tcaaacaatt tatccttcaa 360
aagacaaact tcttcaatcc gaacagggaa ttcgacttcc gcgatctcca ctggtgcatt 420
aacccaccta gcaagatcaa ggtgaatttt actaattact gtgatacagt tggggtcaaa 480
aaatctattg catcggcagc aaatcccatc attttatcag cactctccgg agccagaggt 540
gacatattcc cgccgtgcag atgcagtgga gctactactt cagtaggcag agtattcccc 600
ctatccgtat cattatccat gtctttgata tcaagaacat cagagataat caatatgcta 660
accgctatct cagacggaat gtatggtaaa acttatttgc tagtgcctga ttatattgaa 720
ggggagttcg actcgcaaaa gattcgagtc tttgagatag ggtttatcag acggtggctg 780
aatgacatgc ctttactcca gacaaccaac tatatggtcc ttccggaaac ttccaaagcc 840
aaggtatgta ctatagcagt gggcgagctg acactagctt ccttgtgtgt agatgagagc 900
accgtattgt tatatcatga cagcaatggt tcacaaaatg gtattctagt agtgacattg 960
ggaatatttg ggcaacacc tatggatcaa gttgaagagg tgatacctat cgctcaccca 1020
tcagtggaga gaatacatat aacaaatcac cgtgggttca taaaagattc aatagtaacc 1080

-continued

```
tggatggtgc ctgtattggt ctcagagaaa caagaggagc aaaaaaactg tctggagtct   1140

gcttgtcaaa gaaaaaccta tcctatgtgc aaccaaacgt catgggaacc ctttggagga   1200

ggacagttgc cctcttatgg gcggttgaca ttacctctag atccaagcat tgaccttcag   1260

cttaacatat catttacata tggtccggtt atactgaacg gagacggtat ggattattat   1320

gaaagcccgc ttttggactc cggatggctt accatacctc ctaagaacgg aacagtcctt   1380

ggattgataa acaaagcaag tagaggagac cagttcactg tgaccccccca tgtgttgaca   1440

tttgcgccca gggaatcaag tggaaattgt tatttgccta ttcaaacatc ccagattatg   1500

gataaagatg tccttactga gtccaattta gtagtgttac ctacacagaa ttttaggtat   1560

gtcatagcaa catatgatat atcccggggc gatcatgcaa ttgtttatta tgtttatgac   1620

ccaatccgga cgatttctta tacataccca tttagactaa ctaccaaggg tagacctgat   1680

ttcctaagga ttgaatgttt tgtgtgggat gacgatttgt ggtgtcatca attttaccga   1740

ttcgaggcta acattactaa ctctacaacc agtgttgaga atttagtccg tataagattc   1800

tcatgtaacc gttcaaaacc ttga                                          1824
```

<210> SEQ ID NO 46
<211> LENGTH: 1824
<212> TYPE: DNA
<213> ORGANISM: artificial sequence
<220> FEATURE:
<223> OTHER INFORMATION: DQ228166 encoding CDV HA ABB51156
<220> FEATURE:
<221> NAME/KEY: misc_feature
<222> LOCATION: (1027)..(1027)
<223> OTHER INFORMATION: n is a, c, g, or t

<400> SEQUENCE: 46

```
atgctctcct accaagacaa ggtgggtgcc ttctataaag ataatgcaag agccaattca     60

tccaagctgt ccttagtgac agaagagcaa gggggtagaa gaccaccctt tttgctgttt    120

gtccttctcg tcctactggt tggaatcatg gccttgcttg ctatcactgg agttcgattt    180

catcaagtat caaccagcaa tatggaattt agtagattgc tgaaagagga tatggagaaa    240

tctgaggccg tacatcatca agtcatagat gttttgacac cgctcttcaa aatcatcgga    300

gatgagattg ggttacggtt gccacaaaaa ctaaacgaga ttaaacaatt tatccttcaa    360

aagacaaact tcttcaatcc gaacagggaa ttcgacttcc gcgatctcca ctggtgcatt    420

aacccaccta gtaagatcaa ggtgaatttt actaattact gcgatacaat tgggatcaga    480

aaatctattg catcggcagc aaatcctatc cttttatcag cactttctgg aggcagaggt    540

gacatattcc caccatacaa gtgcaatgga gctgctactt cagtaggcag agttttcccc    600

ctttcagtat cattgtccat gtctttgatc tcaaaaacat cagggataat caatatgcta    660

accgctatct cagacggagt gtatggtaaa acttacttgc taatgcctga ttatattgaa    720

ggggagttcg acacgcaaaa gattcgagtc tttgagatag ggttcatcaa acggtggctg    780

aatgacatgc cattactcca gacaaccaac tatattgtcc tcccggagaa ttccaaagcc    840

aaggtatgta ctatagcagt gggtgagttg acactggctt ccttgtgtgt agatgagagc    900

accgtattgt tatatcatga cagcaatggt tcacaagatg gtattctagt agtgacactg    960

ggaatattcg gggcaacacc tatggatcaa gttgaagagg tgatacctgt cgctcaccca   1020

tcagtanaaa aaatacatat aacaaatcac cgtgggttca taaaagattc aatagcaacc   1080

tggatggtgc ctgcattgat ctctggggaa caagaggaac aaaaaaattg tctggagtcg   1140

gcttgtcaaa gaaaatccta ccctatgtgc aaccaaacgt catggaaacc ctttggagga   1200
```

ggacagttgc catcttatgg gcggttgaca ttacctctag atccaggcat tgaccttcaa 1260
cttaacatat catttacata cggtccggtt atactgaatg gagacggtat ggattattat 1320
gaaagcccac ttttggactc cggatggctt accattcctc ccaagaacgg aacaattctt 1380
ggattgataa acaaggcaag tagaggagac cagttcactg taatccccca tgtgttgaca 1440
tttgcgccca gggaatcaag tgggaattgt tatttaccta ttcaaacatc tcagattatg 1500
gataaagatg tccttactga gtccaattta gtggtattgc ctacacagaa ttttagatat 1560
gtcatagcaa catatgatat atcccggaac gatcatgcga ttgtttatta tgtttatgac 1620
ccaatccgga ctatttctta tacgcaccca tttagactaa ctactaaggg tagacctgat 1680
ttcctaagga ttgaatgttt tgtgtgggat gatgatttgt ggtgtcacca attttaccgg 1740
ttcgaggctg acatcaccaa ctctgcaacc agtgttgaga atttggtccg tataagattc 1800
tcatgtaacc gttcaaaacc ttga 1824

<210> SEQ ID NO 47
<211> LENGTH: 1824
<212> TYPE: DNA
<213> ORGANISM: artificial sequence
<220> FEATURE:
<223> OTHER INFORMATION: DQ889187 encoding CDV HA ABK35780

<400> SEQUENCE: 47
atgctctcct accaagacaa ggtgagtgcc ttctataagg ataatgcaag agccaattca 60
tccaaactgt ccttagtgac agaagaacat gggagcagga gaccacccta tttgctgttt 120
atccttctca tcctactggt tggaatcatg gccttgcttg ctatcactgg agctcgattt 180
caccaagtat caactagcaa tatggaattt agcagattgc tgaaagagga tatggagaaa 240
tcagaggccg tacatcacca agtcatagat gtcttgacac cgctctttaa aattattggt 300
gatgagattg ggttacggtt gccacaaaaa ctaaacgaga tcaaacagtt tatccttcaa 360
aagacaaact tcttcaatcc gaaaagggaa ttcgacttcc gcgacctcca ctggtgcatt 420
aacccaccta gtaagatcaa ggtgaatttt actaattact gcgatacaat tgggatcaga 480
aaatctattg cattggcagc aaatcccatc cttttgtcgg cactctccag aggcaggggt 540
gacatattcc caccatacag atgtagtgga gctgctactt cagtaggcag agttttcccc 600
ctctcagtat cattgtccat gtctttgatc tcaagaacat cagagataat caatatgcta 660
accgctatct cagatggagt gtatggtaaa acttacttgc tagtgcctga ttatattgaa 720
ggggaattcg acacacaaaa gattcgagtc tttgagatag ggttcatcaa acggtggctg 780
aatgacatgc cattactcca gacaaccaac tatatggtcc tcccggagaa ttccaaagcc 840
aaggtatgta ctatagcagt gggcgagttg acactggctt ccttgtgtgt agatgagagc 900
actgtattac tatatcatga cagcaatggt tcacaagatg gtattctagt agtgacgctg 960
ggaatatttg ggcaacaccc tatggatcaa gttgaagagg tgatacctgt cgctcatcca 1020
tcagtagaaa aaatacatat aacaaatcac cgtgggttca taaaagattc aatagcaacc 1080
tggatggtgc ctgtattggt ctctgagaac caagaggaac aaaaaaattg tctggagtcg 1140
gcttgtcaaa gaaaatccta ccctatgtgc aaccaaacgt catgggaacc ctttggagga 1200
ggacagctgc catcttatgg gcggttgaca ttacctctag atccaggcat tgaccttcaa 1260
cttaatctat cgtttacata cggtccgatt atactgaatg gagacggtat ggattattat 1320
gaaagcccac ttttgaactc cggatggctt accattcctc ccaagaacgg gacaattctt 1380

-continued ggattgataa acaaagcaag tagaggagac cagttcactg taacccccca tgtgttgaca 1440
tttgcgccta gggaatcaag tgggaattgt tatttaccta ttcaaacatc tcagattatg 1500
gataaagatg tccttactga gtccaatttg gtggtgttgc ctacacagaa ttttagatat 1560
gtcatagcaa catatgatat atcccgggat gatcatgcga ttgtttatta tgtttatgac 1620
ccaatccgga cgatttctta tacgtaccca tttagactaa ctaccaaggg tagacctgat 1680
ttcctaagga ttgaatgttt tgtgtgggat tacgatttgt ggtgtcacca attttaccga 1740
ttcgaggctg acatcaccaa ctctacaacc agtgttgaga atttagtccg tataagattc 1800
tcatgtaacc gttcaaaacc ttga 1824

<210> SEQ ID NO 48
<211> LENGTH: 1824
<212> TYPE: DNA
<213> ORGANISM: artificial sequence
<220> FEATURE:
<223> OTHER INFORMATION: FJ423608 encoding CDV HA ACJ46470

<400> SEQUENCE: 48
atgctctctt accaagacaa ggtgggtgcc ttctataagg ataatgcaag agctaattca 60
tccaagctgt ccttagtgac agaagagcaa gggggaagga gaccacccta cttgtttttt 120
gtccttctca ccctactgat tggaatcctg gccttgcttg ccatcactgg agttcgattt 180
caccaagtat caactagcaa tatggaattt agcagattgc tgaaagagga tatggagaaa 240
tcagaggccg tacatcacca agtcatagat gtcttgacac cgctcttcaa aattattgga 300
gatgagattg ggttacggtt gccacaaaaa ctaaacgaga tcaaacaatt tatccttcaa 360
aagacaaact tcttcaatcc gaacagggaa ttcgacttcc gcgatctcca ctggtgcatt 420
aacccaccta gcaagatcaa ggtgaatttt actaattact gtgatacagt tggggtcaaa 480
aaatctatta catcggcagc aaatcccatc attttatcag cactctccgg agccagaggt 540
gacatattcc cgccgtacag atgcagtgga gctactactt cagtaggcag agtattcccc 600
ctatctgtat cattatccat gtctttgata tcaagaacat cagagataat caatatgcta 660
accgctatct cagacggagt gtatggtaaa acttatttgc tagtgcctga ttatattgaa 720
ggggagttcg actcgcaaaa gattcgagtc tttgagatag ggtttatcaa acggtggctg 780
aatgacatgc ctttactcca gacaaccaac tatatggttc tcccggaaac ttccaaagcc 840
aaggtatgta ctatagcagt gggcgagctg acactagctt ccttgtgtgt agatgagagc 900
actgtattat tatatcatga cagcaatggt tcacaaaatg gtattctagt agtgacattg 960
ggaatatttg ggcaacatct tatggatcaa gttgaagagg tgatacctat cgctcaccca 1020
tcagtggaga gaatacatat aacaaatcac cgtgggttca taaaagattc aatagtaacc 1080
tggatggtgc ctgtattggt ctctgagaaa caagaggagc aaaaaaactg tctggagtct 1140
gcttgtcaaa gaaaatccta ccctatgtgc aaccaaacgt catgggaacc ctttggagga 1200
ggacagttgc cttcttatgg gcggttgaca ttacctctag atccaagcat tgaccttcaa 1260
cttaacatat catttacata tggtccggtt atactgaacg gggacggtat ggattattat 1320
gaaagcccac ttttggaatc cggatggctt accatacccc ctaagaacgg aacagtcctt 1380
ggattgataa acaaagcaag tagaggagac cagttcactg cgaccccccca tgtgttgaca 1440 tttgcgccca gggaatcaag tggaaattgt tatttgccta ttcaaacatc ccagattatg 1500
gataaagatg tccttactga gtccaattta gtggtgttac ctacacagaa ttttagatat 1560
gtcatagcaa catatgatat atcccggggc gatcatgcaa ttgtttatta tgtttatgac 1620

```
cctatccgga cgatttctta tacataccca tttagactaa ctaccaaagg tagacctgat   1680

ttcctaagga ttgaatgttt tgtgtgggat gacgatttgt ggtgtcatca attttaccga   1740

ttcgaggcta acatcactaa ctctacaacc agtgttgaga atttagtccg tataagattc   1800

tcatgtaacc gttcaaaacc ttga                                          1824
```

<210> SEQ ID NO 49
<211> LENGTH: 1824
<212> TYPE: DNA
<213> ORGANISM: artificial sequence
<220> FEATURE:
<223> OTHER INFORMATION: EU325730 encoding CDV HA ABX84040

<400> SEQUENCE: 49

```
atgctctctt accaagacaa ggtgggtgcc ttctataagg acaatgcaag agctaattca     60

tccaagctgt ccttagtgac agaagagcaa gggggaagga gaccacccta tttgctgttt    120

gtccttctca tcctactgat tggaatcctg gccttgcttg ccatcactgg agttcgattt    180

caccaagtat caactagcaa tatggaattt agcagattgc tgaaagagga tatggagaaa    240

tcagaggccg tacatcacca agtcatagat gtcttgacac cgctcttcaa aattattgga    300

gatgagattg ggttgcggtt gccacaaaaa ctaaacgaga tcaaacaatt tatccttcaa    360

aagacaaact tcttcaatcc gaacagggaa ttcgacttcc gcgatctcca ctggtgcatt    420

aacccaccta gcaagatcaa ggtgaatttt actaattact gtgatacagt tggggtcaaa    480

aaatctattg catcggcagc aaatcccatc attttatcag cactctccgg agccagaggc    540

gacatattcc cgccgtacag atgcagtgga gctactactt cagtaggcag agtattcccc    600

ctatccgtat cattatccat gtctttgata tcaagaacat cagagataat caatatgcta    660

accgctatct cagacggagt gtatggtaaa acttatatgc tagtgcctga ttatattgaa    720

ggggagttcg actcgcaaaa gattcgagtc tttgagatag ggtttatcaa acggtggctg    780

aataacatgc ctttactcca gacaaccaac tatatggtcc tcccggaaac ttccaaagcc    840

aaggtatgta ctatagcagt gggcgagctg acactagctt ccttgtgtgt agatgagagc    900

accgtattgt tatatcatga cagcaatggt tcacaaaatg gtattctagt agtgacattg    960

ggaatatttg ggcaacacc tatggatcaa gttgaagagg tgatacctat cgctcaccca   1020

tcagtggaga gaatacatat aacaaatcac cgtgggttca taaaagattc agtagtaacc   1080

tggatggtgc ctgtattggt ctctgagaaa caagaggagc aaaaaaactg tctggagtct   1140

gcttgtcaaa gaaaatccta cccgatgtgc aaccaaacgt catgggaacc ctttggagga   1200

ggacagttgc cttcttatgg gcggttgaca ttacctctag atccaagcgt tgaccttcaa   1260

cttaacatat catttacata tggtccggtt atactgaacg gagacggtat ggattattat   1320

gaaagcccac ttttggaatc cggatggctt gccatacccc ctaagaacgg aacagtcctt   1380

ggattgataa acaaagcaag tagaggagac cagttcactg tgacccccca tgtgttgaca   1440

tttgcgccca gggaatcaag tgggaattgt tatttgccta ttcaaacatc ccagattatg   1500

gataaagatg tccttactga gtccaattta gtggtgttac ctacacagaa ttttagatat   1560

gtcatagcaa catatgatat atcccggggc gatcatgcaa ttgtttatta tgtttatgac   1620

cctatccgga cgatttctta tacataccca tttagactaa ctaccaaggg tagacctgat   1680

ttcctaagga ttgaatgttt tgtgtgggat gacgatttgt ggtgtcatca attttaccga   1740

ttcgaggcta acatcactaa ctctacaacc agtgttgaga atttagtccg tataagattc   1800
```

tcatgtaacc gttcaaaacc ttga 1824

<210> SEQ ID NO 50
<211> LENGTH: 4178
<212> TYPE: DNA
<213> ORGANISM: artificial sequence
<220> FEATURE:
<223> OTHER INFORMATION: vCP2392 part containing C3 arms, H6 promoter and GM-CSF
<220> FEATURE:
<221> NAME/KEY: misc_feature
<222> LOCATION: (1)..(2586)
<223> OTHER INFORMATION: this is the C3 arm region
<220> FEATURE:
<221> NAME/KEY: promoter
<222> LOCATION: (2587)..(2772)
<223> OTHER INFORMATION: this is the H6 promoter region
<220> FEATURE:
<221> NAME/KEY: CDS
<222> LOCATION: (2773)..(3207)
<223> OTHER INFORMATION: this is the caGM-CSF coding region
<220> FEATURE:
<221> NAME/KEY: misc_feature
<222> LOCATION: (3208)..(4178)
<223> OTHER INFORMATION: this is the C3 arm region

<400> SEQUENCE: 50
ctttatacta ctgggttaca acagctggtg ataacagaat gtaaatcatt attacttaat 60
agttccatta ttatatgttt gatatctata ggtaacctac ctattattcc tagattctta 120
ctctctttta cagctttaac tattagctga tgtctatgaa aagctaatga tttatttttc 180
cgtattaatt ccctatatat acgtatacat gcaggtatct tattaactct aggattagtt 240
acgaacttta ccataagatc tatgttattg tcaagaaaga tattaaaaga atatatagaa 300
tttaacttta tatgtgttat aacatctagt tctttttcgc atgattcttt tatagatagt 360
agtcttttat tactgtttat atgttccatg tttactataa aaccttctga attagctatt 420
tcaggatttt tagatatttc taacatcatt ttagatatta tcataatagc tatcttgtca 480
tctaaaaagc taacacaagt tagaggcgta ttaccgtgat tatttagaga attatagtcg 540
gcgttataag ataaaagtaa ttttatatta ttaaaactat tagataacat agctttatgt 600
aaaggagtat ttccagataa cttagcttta gcatttacgt aagcaccgtg gtcaagtaag 660
agtttaacaa attctgtttt catagaacta actgccatgt atagaggagt gaaaccttta 720
tgattataga cgtttacata gcaaccatat aataagatcg cattcagtat attaatatct 780
ttcatttcta tagctatgtg aataacatgt ttatctaatc ctaccaactt tgtatcagta 840
ccgtacttca gtaataagtt tactatagtt ttgtttttag atgcaacagc tatatttaga 900
acggtatcta tatgattatt aaccacatta acattagatc ctctttctaa aagtgtcttt 960
gttgtttcga tatcgttacg tgaaacagcg taatgtaagg gactgcccat acagtcatct 1020
attacgttta tatcagctcc tagatttaac agaagtgctg ttacatcttt tcttctatta 1080
attaccgaat gatgtaatgg ggttttacct aaatcatctt gttcgtttat aggcactccg 1140
tgatttataa gtaacgctat tatatcgtaa ctacaattat ttttaagtgc ctttatgaga 1200
tactgtttat gcaaaaataa acttttatct attttaatac tattatctaa caatatccta 1260
attaaatcta tattcttata ctttatagcg taatgtaacg gagtttcaaa atttctagtt 1320
tgtatattaa gatcaatatt aaaatctata aatattttat acatatcatc agatatctta 1380
tcatacagta catcgtaata atttagaaag aatctattac aattaacacc ttttttttaat 1440 aaatatctag ttaatgactt attgtttcta tatacagaaa tatataacgg actatttcca 1500

-continued

```
gaatgtatct gttctatgtc agcgccagaa tctattagta gtttagcaat ttctgtatta   1560
tctaaactag cagctttatg aagaggagga tttttacatt ttaaaatatc ggcaccgtgt   1620
tctagtaata attttaccat ttctatatca gaaatactta cggctaaata caaagacgtt   1680
gatagtatat ttacgttatt gtatttgcat tttttaagta tataccttac taaatttata   1740
tctctatacc ttatagcttt atgcagttca tttataagtc ttccattact catttctggt   1800
aatgaagtat tatatatcat tatgatatta tctctatttt attctaataa aaaccgttat   1860
catgttattt attatttgtt ataattatac tatttaataa attataccaa atacttagat   1920
acttattaat accatcctag aacttgtatt tcttgccccc taaacttgga catgcactcc   1980
attaggcgtt tcttgttttc gacatcgtcc tccttaacat atcctactgt tatgtgagga   2040
ttccacggat tatctactgt gatatcacca aacacgtcct tcgaacaggg taccgcattc   2100
agcagaacat ttcttagggc tctaagttca tcagatacct ccagtttcat aactacagcg   2160
catcctttcg ctcccaactg tttagaggcg ttactctgag gaaaacacat ctcttcttta   2220
cagactatag aaatagtctg taaatcttga tcagttattt gctttttgaa attttcaaat   2280
ctatcacatt gatccatatt tgctattcca agagttatat gaggaaaaat atcacatcct   2340
gtcatgtatt ttattgtaac attattataa tctgtaacat cagtatctaa cctaacgtcg   2400
taaaagttaa cagatgccca gttactataa tcccaaggaa ccttaacatc taatcccatt   2460
aaaatagtat cctttctact atttttttca ttggcaagta tgtggcttag tttacacaaa   2520
attcctgcca ttttgtaacg atagcgaagc aatagcttgt atgcttttta tttgattaac   2580
taggggttaa ttaattagtc atcaggcagg gcgagaacga gactatctgc tcgttaatta   2640
attagagctt ctttattcta tacttaaaaa gtgaaaataa atacaaaggt tcttgagggt   2700
tgtgttaaat tgaaagcgag aaataatcat aaattatttc attatcgcga tatccgttaa   2760
gtttgtatcg taatgtggct gcagaacctg ctgttcctgg gcaccgtggt gtgcagcatc   2820
agcgccccca ccagatcccc caccctggtg acccggccca gccagcacgt ggacgccatc   2880
caggaagccc tgagcctgct gaacaacagc aacgacgtga ccgccgtgat gaacaaggcc   2940
gtgaaggtgg tgtccgaggt gttcgacccc gagggcccca cctgcctgga aacccggctg   3000
cagctgtaca aagagggcct gcagggcagc ctgaccagcc tgaagaaccc cctgaccatg   3060
atggccaacc actacaagca gcactgcccc cccacccccg agagcccttg cgccacccag   3120
aacatcaact tcaagagctt caaagagaac ctgaaggact tcctgttcaa catccccttc   3180
gactgctgga agcccgtgaa gaagtgatga ctcgagtttt tattgactag ggtttttat    3240
agctaattag tcaaatgtga gttaatatta gtatactaca ttactaattt attacatatt   3300
catttatatc aatctagtag catttagctt ttataaaaca atataactga atagtacata   3360
ctttactaat aagttataaa taagagatac atatttatag tattttactt tctacactga   3420
atataataat ataattatac aaatataatt tttaatacta tatagtatat aactgaaata   3480
aaataccagt gtaatatagt tattatacat ttataccaca tcaaagatga gttataacat   3540
cagtgtcact gttagcaaca gtagttatac gatgagtagt tactctcgta tggcgttagt   3600
atgtatgtat cttctagttt tcttagtagg cattatagga aacgtcaagc ttataaggtt   3660
attaatggta tctagaaata tatctattat accgtttctc aacttgggaa tagccgattt   3720
gctgtttgtg atattcatac ctttatacat tatatacata ctaagtaatt tccattggca   3780
ttttggtaaa gcactttgta aaattagttc tttcttttt acttctaaca tgtttgcaag    3840
tatattttta ataactgtaa taagcgtata tagatatgta aaaattaccc ttcctggatt   3900
```

-continued

```
tacctataaa tatgttaaca ttagaaatat gtacattact atatttttca tatggattat   3960

ttctattata ctagggattc ctgctcttta ctttagaaat actatcgtaa caaaaaataa   4020

cgacacgctg tgtattaatc attatcatga taatagagaa attgctgaat tgatttacaa   4080

agttattatc tgtatcagat ttattttagg atacctacta cctacgataa ttatactcgt   4140

atgctatacg ttactgatct acagaactaa caatgcat                           4178


<210> SEQ ID NO 51
<211> LENGTH: 621
<212> TYPE: DNA
<213> ORGANISM: artificial sequence
<220> FEATURE:
<223> OTHER INFORMATION: vCP2392 part seq containing H6 promoter +
      caGM-CSF
<220> FEATURE:
<221> NAME/KEY: promoter
<222> LOCATION: (1)..(186)
<223> OTHER INFORMATION: this is the H6 promoter region
<220> FEATURE:
<221> NAME/KEY: CDS
<222> LOCATION: (187)..(621)
<223> OTHER INFORMATION: this is the caGM-CSF coding region

<400> SEQUENCE: 51

ttaattaatt agtcatcagg cagggcgaga acgagactat ctgctcgtta attaattaga     60

gcttctttat tctatactta aaaagtgaaa ataaatacaa aggttcttga gggttgtgtt    120

aaattgaaag cgagaaataa tcataaatta tttcattatc gcgatatccg ttaagtttgt    180

atcgtaatgt ggctgcagaa cctgctgttc ctgggcaccg tggtgtgcag catcagcgcc    240

cccaccagat cccccaccct ggtgacccgg cccagccagc acgtggacgc catccaggaa    300

gccctgagcc tgctgaacaa cagcaacgac gtgaccgccg tgatgaacaa ggccgtgaag    360

gtggtgtccg aggtgttcga ccccgagggc cccacctgcc tggaaacccg gctgcagctg    420

tacaaagagg gcctgcaggg cagcctgacc agcctgaaga accccctgac catgatggcc    480

aaccactaca agcagcactg cccccccacc cccgagagcc cttgcgccac ccagaacatc    540

aacttcaaga gcttcaaaga gaacctgaag gacttcctgt tcaacatccc cttcgactgc    600

tggaagcccg tgaagaagtg a                                              621
```

RECOMBINANT CDV COMPOSITIONS AND USES THEREOF

CROSS-REFERENCE TO RELATED APPLICATIONS

This application is a continuation application of U.S. application Ser. No. 13/035,904 filed on Feb. 25, 2011 which claims benefit of U.S. provisional application Ser. No. 61/308,620 filed Feb. 26, 2010.

FIELD OF THE INVENTION

The present invention relates to formulations for combating canine distemper virus and other canine virus infections in animals. Specifically, the present invention provides vectors that contain and express in vivo or in vitro CDV HA that elicit an immune response in animals against canine distemper virus, including compositions comprising said vectors, methods of vaccination against canine distemper virus, and kits for use with such methods and compositions. The present invention also provides vectors that contain and express in vivo or in vitro CDV HA and GM-CSF that elicit an immune response in animals against canine distemper virus and other canine virus, and compositions comprising said vectors.

BACKGROUND OF THE INVENTION

Canine distemper (CD) is a highly infectious, febrile disease of dogs and other carnivores (Fenner, et al., 1987, Veterinary Virology, Academic Press, Inc., pp. 485-503). The mortality rate is high, ranging between 30 and 80 percent. Dogs survived often have permanent central nerve system damage (Fenner, et al., 1987). The established etiology of CD is infection by a member of the Paramyxovirus family, morbillivirus genus known as CD virus (CDV). In general, Paramyxoviruses are enveloped viruses containing an 18-20 kb single stranded RNA genome of negative polarity. The genome encodes 5 to 7 structural proteins including a fusion (F) and either a hemagglutinin-neuraminidase (HN) or hemagglutinin (HA) glycoprotein. The membrane glycoprotein hemagglutinin (HA) is responsible for hemagglutination and attachment of the virus to the host cell, and the fusion glycoprotein (F) causes membrane fusion between the virus and the infected cell or between the infected and adjacent uninfected cells (Graves et al., 1978, Virology 86:254-263). For CDV, both F and HA glycoproteins are found present in the viral envelope and on the surface of infected cells. By inference from analyses with other morbillivirus members, the CDV F and HA glycoproteins appear important for CDV infection and its immunobiology (Diallo A., 1990, Vet. Micro. 23: 155-163). Poxvirus based recombinant CDV vaccines have been developed to protect and treat dogs (U.S. Pat. No. 5,756,102). U.S. Pat. No. 6,228,846 disclosed DNA plasmid based vaccines expressing CDV antigens.

Granulocyte-macrophage colony-stimulating factor (GM-CSF) was first discovered in 1977 (Burgess et al., 1977, J. Biol. Chem. 252:1998-2003). GM-CSF has many physiological roles. In particular, GM-CSF stimulates the production, the development and the formation of colonies of granulocyes, macrophages, eosinophils and megakaryocytes. (Dy M., in "les Cytokines" Cavailon 1995 ed. Masson, Paris, France, 43-56). GM-CSF induces in particular a macrophagic cytotoxocity, stimulates antibody-dependent cytotoxic activity (ADCC) and the recruitment of leukocytes at the level of the sites of inflammation.

The sizes of the nucleotide sequences encoding the known GM-CSFs from various species vary from 381 to 432 nucleotides. The human and murine nucleotide sequences have a degree of homology of 69%. The degree of homology is 54% at the level of the amino acid sequence (Cantrell et al., 1985, Proc. Natl. Acad. Sci. USA 82:6250-6254). An equine GM-CSF was identified which has a size of 144 amino acids (U.S. Pat. No. 7,250,161). Two canine GM-CSFs were identified in U.S. Pat. No. 5,702,919 and U.S. Pat. No. 5,606,024, which have 127 amino acids and 174 amino acids respectively.

The administration of heterologous GM-CSF does not make it possible to obtain an optimum adjuvant effect, in particular a stimulation of the activity of the haematopoietic cells and a substantial increase in the immune response.

There is thus a general need for an improvement in efficacy and safety of the CDV vaccines and for more effective protection in field conditions.

The invention provides a solution for optimizing the immunological effect of caGM-CSF while retaining high safety for the vaccinated dogs.

SUMMARY OF THE INVENTION

An object of this invention can be any one or all of providing recombinant vectors or viruses as well as methods for making such viruses, and providing compositions and/or vaccines as well as methods for treatment and prophylaxis of infection by CDV and other canine virus.

The invention provides a recombinant vector, such as a recombinant virus, that contains and expresses at least one exogenous nucleic acid molecule and, the at least one exogenous nucleic acid molecule may comprise a nucleic acid molecule encoding an immunogen or epitope of interest from CDV, such as CDV HA.

The invention provides a recombinant vector, such as a recombinant poxvirus that contains a first polynucleotide encoding a CDV HA polypeptide and/or variant or fragment thereof and a second polynucleotide encoding a canine GM-CSF polypeptide and/or variant or fragment thereof.

The invention further provides compositions or vaccines comprising such an expression vector or the expression product(s) of such an expression vector.

The invention further provides methods for inducing an immunological (or immunogenic) or protective response against CDV and other canine virus, as well as methods for preventing or treating CDV and other canine virus or disease state(s) caused by CDV and other canine virus, comprising administering the expression vector or an expression product of the expression vector, or a composition comprising the expression vector, or a composition comprising an expression product of the expression vector.

The invention also relates to expression products from the virus as well as antibodies generated from the expression products or the expression thereof in vivo and uses for such products and antibodies, e.g., in diagnostic applications.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIGS. 1A-1B provide a table identifying the SEQ ID NO assigned to the polynucleotide and protein sequence.

FIG. 2 provides sequence alignment between SEQ ID NO:2 and SEQ ID NO:5.

FIG. 3 depicts the plasmid maps of pCXL1557.1 and pJSY2218.1.

FIGS. 13A-13F provide the sequence alignment of CDV HA proteins and sequence identity percentage at the amino acid level.

FIGS. 14A-14C provide the sequence alignment of codon-optimized CDV HA DNA and wild-type CDV HA DNA.

FIGS. 15A-15N provide the sequence alignment of CDV HA DNA and sequence identity percentage at the DNA level.

FIG. 16 provides the result of cellular immune response.

FIG. 17 provides CPV2 ELISA result.

DETAILED DESCRIPTION

Figure 4:
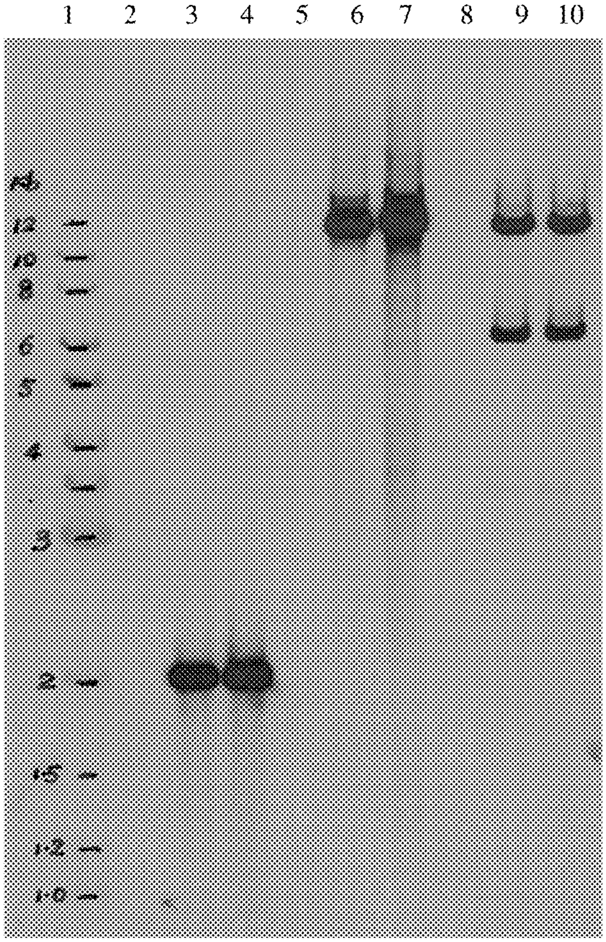
FIG. 4 shows the Southern blot of vCP2263.

Compositions comprising an expression vector comprising a polynucleotide encoding a CDV polypeptide and fragments and variants thereof that elicit an immunogenic response in an animal are provided. The expression vector comprising the polynucleotide encoding CDV polypeptide or fragments or variants may be formulated into vaccines or pharmaceutical compositions and used to elicit or stimulate a protective response in an animal. In one embodiment the CDV polypeptide is a CDV hemagglutinin (HA) polypeptide or active fragment or variant thereof.

Compositions comprising an expression vector comprising a polynucleotide encoding a CDV HA polypeptide or active fragments or variants thereof and a polynucleotide encoding a GM-CSF polypeptide or active fragments or variants thereof are provided.

It is recognized that the polypeptides of the invention may be full length polypeptides or active fragments or variants thereof. By "active fragments" or "active variants" is intended that the fragments or variants retain the antigenic nature of the polypeptide. Thus, the present invention encompasses any CDV polypeptide, antigen, epitope or immunogen that elicits an immunogenic response in an animal. The CDV polypeptide, antigen, epitope or immunogen may be any CDV polypeptide, antigen, epitope or immunogen, such as, but not limited to, a protein, peptide or fragment or variant thereof, that elicits, induces or stimulates a response in an animal.

A particular CDV polypeptide of interest is CDV hemagglutinin (HA). CDV HA refers to a type of hemagglutinin found on the surface of the CDV. It is an antigenic glycoprotein and is responsible for binding the virus to the cell that is being infected. There are different HA antigens, associated with the different CDV strains which circulate in the field, any of which can be used in the practice of the invention. However, there are different antigens, such as the Fusion (F) glycoprotein and Nucleoprotein (NP), any of which can be used in the practice of the invention. It is further recognized that precursors of any of these antigens can be used. The antigenic polypeptides of the invention are capable of protecting against CDV. That is, they are capable of stimulating an immune response in an animal.

The term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "CDV HA polypeptide or polynucleotide" refers to any native or optimized CDV HA polypeptide or polynucleotide, and their derivatives and variants.

The term "GM-CSF polypeptide or polynucleotide" refers to any native or optimized GM-CSF polypeptide or polynucleotide, and their derivatives and variants.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Compositions

The present invention relates to a CDV vaccine or composition which may comprise a recombinant or expression vector comprising a polynucleotide encoding a CDV polypeptide, antigen, epitope or immunogen and a pharmaceutically or veterinarily acceptable carrier, excipient, adjuvant, or vehicle. The CDV polypeptide, antigen, epitope or immunogen may be any CDV polypeptide, antigen, epitope or immunogen, such as, but not limited to, a protein, peptide or fragment thereof, that elicits, induces or stimulates a response in an animal.

The present invention relates to a CDV vaccine or composition which may comprise a recombinant or expression vector comprising a polynucleotide encoding a CDV HA polypeptide and a pharmaceutically or veterinarily acceptable carrier, excipient, adjuvant, or vehicle. In one embodiment, the expression vector may further comprise a polynucleotide encoding a GM-CSF polypeptide.

In another embodiment, the pharmaceutically or veterinarily acceptable carrier, excipient, adjuvant, or vehicle may be a water-in-oil emulsion. In yet another embodiment, the water-in-oil emulsion may be a water/oil/water (W/O/W) triple emulsion. In yet another embodiment, the pharmaceutically or veterinarily acceptable carrier, excipient, adjuvant, or vehicle may be an oil-in-water emulsion.

In an embodiment, the CDV polypeptide, antigen or fragment or variant thereof may be a CDV HA polypeptide or fragment or variant thereof. In an aspect of this embodiment, the CDV HA polypeptide or fragment or variant thereof is a recombinant polypeptide produced by a CDV HA gene. In another aspect of this embodiment, the CDV HA gene has at least 70% identity to the sequence as set forth in SEQ ID NO: 1, 35, 36, 37, 38, 39, 40, 41, 42, 43, 44, 45, 46, 47, 48, or 49. In another aspect of this embodiment, the CDV HA polypeptide or fragment or variant thereof has at least 80% identity to the sequence as set forth in SEQ ID NO: 2, 5, 20, 21, 22, 23, 24, 25, 26, 27, 28, 29, 30, 31, 32, 33, or 34.

In another embodiment, the GM-CSF polypeptide, antigen or fragment or variant is a recombinant polypeptide produced by a GM-CSF gene. In another aspect of this embodiment, the GM-CSF gene has at least 70% identity to the sequence as set forth in SEQ ID NO: 3. In another aspect of this embodiment, the GM-CSF polypeptide or fragment or variant thereof has at least 80% identity to the sequence as set forth in SEQ ID NO: 4.

Synthetic antigens are also included within the definition, for example, polyepitopes, flanking epitopes, and other recombinant or synthetically derived antigens. See, e.g., Bergmann et al., 1993; Bergmann et al., 1996; Suhrbier, 1997; Gardner et al., 1998. Immunogenic fragments, for purposes of the present invention, will usually include at least about 3 amino acids, at least about 5 amino acids, at least about 10-15 amino acids, or about 15-25 amino acids or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides encoding an epitope or antigenic determinant of a CDV polypeptide. A polynucleotide encoding a fragment of a CDV polypeptide may comprise or consist essentially of or consist of a minimum of 15 nucleotides, about 30-45 nucleotides, about 45-75, or at least 75, 87 or 150 consecutive or contiguous nucleotides of the sequence encoding the polypeptide. Epitope determination procedures, such as, generating overlapping peptide libraries (Hemmer et al., 1998), Pepscan (Geysen et al., 1984; Geysen et al., 1985; Van der Zee R. et al., 1989; Geysen, 1990; Multipin® Peptide Synthesis Kits de Chiron) and algorithms (De Groot et al., 1999; PCT/US2004/022605) can be used in the practice of the invention.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

The invention further comprises a complementary strand to a polynucleotide encoding a CDV antigen, epitope or immunogen or to a polynucleotide encoding a GM-CSF antigen, epitope or immunogen. The complementary strand can be polymeric and of any length, and can contain deoxyribonucleotides, ribonucleotides, and analogs in any combination.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a partially purified polypeptide preparation is one in which the polypeptide is more enriched than the polypeptide is in its natural environment. That is the polypeptide is separated from cellular components. By "substantially purified" is intended that at least 60%, at least 70%, at least 80%, at least 90%, at least 95%, or at least 98%, or more of the cellular components or materials have been removed. Likewise, a polypeptide may be partially purified. By "partially purified" is intended that less than 60% of the cellular components or material is removed. The same applies to polynucleotides. The polypeptides disclosed herein can be purified by any of the means known in the art.

Moreover, homologs of CDV HA polypeptides and homologs of GM-CSF polypeptides are intended to be within the scope of the present invention. As used herein, the term "homologs" includes orthologs, analogs and paralogs. The tem "anologs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. For example, analogs, orthologs, and paralogs of a wild-type CDV polypeptide can differ from the wild-type CDV polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type CDV polypeptide or polynucleotide sequences, and will exhibit a similar function.

In one embodiment, the present invention provides an expression vector comprising one or more polynucleotides encoding one or more polypeptides having at least 70%, at least 75%, at least 80%, at least 85%, at least 90%, at least 95%, 96%, 97%, 98% or 99% sequence identity to a polypeptide having a sequence as set forth in SEQ ID NO: 2, 4, 5, 20, 21, 22, 23, 24, 25, 26, 27, 28, 29, 30, 31, 32, 33, or 34. In another embodiment, the present invention provides fragments and variants of the CDV polypeptides or GM-CSF identified above (SEQ ID NO: 2, 4, 5, 20, 21, 22, 23, 24, 25, 26, 27, 28, 29, 30, 31, 32, 33, or 34) which may readily be prepared by one of skill in the art using well-known molecular biology techniques. Variants are homologous polypeptides having amino acid sequences at least 75%, 80%, 85%, 90%, 95%, 96%, 97%, 98%, or 99% identity to the amino acid sequences as set forth in SEQ ID NO: 2, 4, 5, 20, 21, 22, 23, 24, 25, 26, 27, 28, 29, 30, 31, 32, 33, or 34.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the CDV polypeptide or GM-CSF primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein.

An immunogenic fragment of a CDV polypeptide or GM-CSF polypeptide includes at least 8, 10, 13, 14, 15, or 20 consecutive amino acids, at least 21 amino acids, at least 23 amino acids, at least 25 amino acids, or at least 30 amino acids of a CDV HA polypeptide having a sequence as set forth in SEQ ID NO: 2, 5, 20, 21, 22, 23, 24, 25, 26, 27, 28, 29, 30, 31, 32, 33, or 34 or variants thereof, or of a GM-CSF polypeptide having a sequence as set forth in SEQ ID NO:4 or variants thereof.

In another aspect, the present invention provides an expression vector comprising a polynucleotide encoding a CDV HA polypeptide, such as a polynucleotide encoding a polypeptide having a sequence as set forth in SEQ ID NO: 2, 5, 20, 21, 22, 23, 24, 25, 26, 27, 28, 29, 30, 31, 32, 33, or 34. In yet another aspect, the present invention provides an expression vector comprising a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 2, 5, 20, 21, 22, 23, 24, 25, 26, 27, 28, 29, 30, 31, 32, 33, or 34, or a conservative variant, an allelic variant, a homolog or an immunogenic fragment comprising at least eight or at east ten consecutive amino acids of one of these polypeptides, or a combination of these polypeptides.

In yet another aspect, the present invention provides an expression vector comprising a polynucleotide encoding a GM-CSF polypeptide, such as a polynucleotide encoding a polypeptide having a sequence as set forth in SEQ ID NO: 4. In yet another aspect, the present invention provides an expression vector comprising a polynucleotide encoding a polypeptide having at least 70%, at least 75%, at least 80%, at least 85%, at least 90%, at least 95%, 96%, 97%, 98% or 99% sequence identity to a polypeptide having a sequence as set forth in SEQ ID NO: 4, or a conservative variant, an allelic variant, a homolog or an immunogenic fragment comprising at least eight or at east ten consecutive amino acids of one of these polypeptides, or a combination of these polypeptides.

In one embodiment the polynucleotide of the present invention includes a polynucleotide having a nucleotide sequence as set forth in SEQ ID NO: 1, 3, 6, 7, 8, 9, 14, 19, 35, 36, 37, 38, 39, 40, 41, 42, 43, 44, 45, 46, 47, 48, or 49, or a variant thereof. In another embodiment, the polynucleotide of the present invention includes a polynucleotide having at least 70%, at least 75%, at least 80%, at least 85%, at least 90%, at least 95%, at least 95%, 96%, 97%, 98% or 99% sequence identity to one of a polynucleotide having a sequence as set forth in SEQ ID NO: 1, 3, 6, 7, 8, 9, 14, 19, 35, 36, 37, 38, 39, 40, 41, 42, 43, 44, 45, 46, 47, 48, or 49, or a variant thereof.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for CDV HA polypeptides or GM-CSF polypeptides, the DNA sequence of the CDV HA gene or GM-CSF gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of CDV HA protein or GM-CSF protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the CDV HA polypeptide or the GM-CSF polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.).

The "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

The following documents provide algorithms for comparing the relative identity or homology of sequences, and additionally or alternatively with respect to the foregoing, the teachings in these references can be used for determining percent homology or identity: Needleman S B and Wunsch C D; Smith T F and Waterman M S; Smith T F, Waterman M S and Sadler J R; Feng D F and Dolittle R F; Higgins D G and Sharp P M; Thompson J D, Higgins D G and Gibson T J; and, Devereux J, Haeberlie P and Smithies O. And, without undue experimentation, the skilled artisan can consult with many other programs or references for determining percent homology.

Hybridization reactions can be performed under conditions of different "stringency." Conditions that increase stringency of a hybridization reaction are well known. See for example, "Molecular Cloning: A Laboratory Manual", second edition (Sambrook et al., 1989).

The invention encompasses the CDV polynucleotide or GM-CSF polynucleotide or both contained in a vector molecule or an expression vector and operably linked to a promoter element and optionally to an enhancer.

The present invention further encompasses a canine vaccine or composition which may comprise an aforementioned recombinant vector comprising a polynucleotide encoding a CDV HA polypeptide or antigen and a polynucleotide encoding a GM-CSF polypeptide or antigen, a pharmaceutically or veterinarily acceptable carrier, excipient, adjuvant, or vehicle, and additionally one or more antigens from canine. The present invention further relates to a canine vaccine or composition which may comprise an aforementioned recombinant or expression vector comprising a polynucleotide encoding a GM-CSF polypeptide, a pharmaceutically or veterinarily acceptable carrier, excipient, adjuvant, or vehicle, and additionally one or more antigens from canine. The antigen may be canine antigen selected from the group consisting of rabies, canine parvovirus, canine coronavirus, canine influenza, canine distemper, infectious canine hepatitis, canine herpesvirus, pseudorabies, canine minute virus, *Leptospira, Neospora caninum, Borrelia burgdorferi, Ehrlichia canis, Rickettsia rickettsii, Bordetella bronchiseptica, Blastomyces dermatitidis, Histoplasma capsulatum, Coccidioides immitis, Cryptococcus neoformans, Microsporum canis, Sporothrix schenckii, Aspergillus fumigatus*, and *P. insidiosum*. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

The term "recombinant" means a polynucleotide with semisynthetic or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of a CDV HA polypeptide, antigen, epitope or immunogen or a GM-CSF polypeptide are present in an inventive vector. In minimum manner, this comprises an initiation codon (ATG), a stop codon and a promoter, and optionally also a polyadenylation sequence for certain vectors such as plasmid and certain viral vectors, e.g., viral vectors other than poxviruses. When the polynucleotide encodes a polypeptide fragment, e.g. a CDV HA polypeptide, in the vector, an ATG is placed at 5' of the reading frame and a stop codon is placed at 3'. Other elements for controlling expression may be present, such as enhancer sequences, stabilizing sequences, such as intron and signal sequences permitting the secretion of the protein.

The present invention also relates to compositions or vaccines comprising vectors. The composition or vaccine can comprise one or more vectors, e.g., expression vectors, such as in vivo expression vectors, comprising and expressing one or more CDV HA or GM-CSF polypeptides, antigens, epitopes or immunogens. In one embodiment, the vector contains and expresses a polynucleotide that comprises a polynucleotide coding for and/or expressing a CDV HA antigen, epitope or immunogen, in a pharmaceutically or veterinarily acceptable carrier, excipient, adjuvant, or vehicle. Thus, according to an embodiment of the invention, the other vector or vectors in the preparation comprises, consists essentially of or consists of a polynucleotide that encodes, and under appropriate circumstances the vector expresses one or more other proteins of a CDV HA polypeptide, antigen, epitope or immunogen (e.g., hemagglutinin, neuraminidase, nucleoprotein) or a fragment thereof.

According to another embodiment, the vector or vectors in the composition or vaccine comprise, or consist essentially of, or consist of polynucleotide(s) encoding one or more proteins or fragment(s) of a CDV HA polypeptide, antigen, epitope or immunogen, or a GM-CSF polypeptide, antigen, epitope or immunogen, or a combination thereof. In another embodiment, the composition or vaccine comprises one, two, or more vectors comprising polynucleotides encoding and expressing, advantageously in vivo, a CDV HA polypeptide, antigen, fusion protein or an epitope thereof. The invention is also directed at mixtures of vectors that comprise polynucleotides encoding and expressing different CDV HA polypeptides, antigens, epitopes, fusion protein, or immunogens, e.g., a CDV HA polypeptide, antigen, epitope or immunogen from different species such as, but not limited to, humans, pigs, cows or cattle, dogs, cats, and avian.

In the present invention a recombinant viral vector is used to express a CDV coding sequence or fragments thereof encoding a CDV polypeptide or fragment or variant thereof. Specifically, the viral vector can express a CDV sequence, more specifically a CDV HA gene or fragment thereof that encodes an antigenic polypeptide. Viral vector contemplated herein includes, but not limited to, poxvirus [e.g., vaccinia virus or attenuated vaccinia virus, avipox virus or attenuated avipox virus (e.g., canarypox, fowlpox, dovepox, pigeonpox, quailpox, ALVAC, TROVAC; see e.g., U.S. Pat. No. 5,505,941, U.S. Pat. No. 5,494,8070), raccoonpox virus, swinepox virus, etc.], adenovirus (e.g., human adenovirus, canine adenovirus), herpesvirus (e.g. canine herpesvirus, feline herpesvirus, bovine herpesvirus, swine herpesvirus), baculovirus, retrovirus, etc. In another embodiment, the avipox expression vector may be a canarypox vector, such as, ALVAC. In yet another embodiment, the avipox expression vector may be a fowlpox vector, such as, TROVAC. The CDV polypeptide, antigen, epitope or immunogen may be a CDV HA. For example, the poxvirus vectors comprising the CDV HA may be vectors as described in U.S. Pat. No. 5,756,102. The CDV HA polypeptide or antigen of the invention to be expressed is inserted under the control of a specific poxvirus promoter, e.g., the vaccinia promoter 7.5 kDa (Cochran et al., 1985), the vaccinia promoter I3L (Riviere et al., 1992), the vaccinia promoter HA (Shida, 1986), the cowpox promoter ATI (Funahashi et al., 1988), the vaccinia promoter H6 (Taylor et al., 1988b; Guo et al., 1989; Perkus et al., 1989), inter alia.

According to a yet further embodiment of the invention, the expression vector is a plasmid vector, in particular an in vivo expression vector. In a specific, non-limiting example, the pVR1020 or 1012 plasmid (VICAL Inc.; Luke et al., 1997; Hartikka et al., 1996, see, e.g., U.S. Pat. Nos. 5,846, 946 and 6,451,769) can be utilized as a vector for the insertion of a polynucleotide sequence. The pVR1020 plasmid is derived from pVR1012 and contains the human tPA signal sequence. In one embodiment the human tPA signal comprises from amino acid M(1) to amino acid S(23) of GenBank accession number HUMTPA14. In another specific, non-limiting example, the plasmid utilized as a vector for the insertion of a polynucleotide sequence can contain the signal peptide sequence of equine IGF1 from amino acid M(24) to amino acid A(48) of GenBank accession number U28070. Additional information on DNA plasmids which may be consulted or employed in the practice are found, for example, in U.S. Pat. Nos. 6,852,705; 6,818,628; 6,586,412; 6,576,243; 6,558,674; 6,464,984; 6,451,770; 6,376,473 and 6,221,362. The DNA plasmid based vaccines expressing CDV antigens may be found in U.S. patent application Ser. No. 09/587,964.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding a CDV HA polypeptide, antigen, epitope or immunogen, optionally fused with a heterologous peptide sequence, variant, analog or fragment, operably linked to a promoter or under the control of a promoter or dependent upon a promoter. In general, it is advantageous to employ a strong promoter functional in eukaryotic cells. The strong promoter may be, but not limited to, the immediate early cytomegalovirus promoter (CMV-IE) of human or murine origin, or optionally having another origin such as the rat or guinea pig.

In more general terms, the promoter has either a viral, or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa et al., 2000), or the actin promoter (Miyazaki et al., 1989).

As to the polyadenylation signal (polyA) for the plasmids and viral vectors other than poxviruses, use can be made of the poly(A) signal of the bovine growth hormone (bGH) gene (see U.S. Pat. No. 5,122,458), or the poly(A) signal of the rabbit β-globin gene or the poly(A) signal of the SV40 virus.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Methods of Use and Article of Manufacture

The present invention includes the following method embodiments. In an embodiment, a method of vaccinating an animal comprising administering composition comprising a vector comprising a polynucleotide encoding a CDV HA polypeptide or fragment or variant thereof and a pharmaceutical or veterinarily acceptable carrier, excipient, vehicle, or adjuvant to an animal is disclosed. In one aspect of this embodiment, the animal is an avian, an equine, a canine, a feline, a ferret, a seal, or a porcine.

In another embodiment, a method of vaccinating an animal comprising a composition comprising a vector comprising a polynucleotide encoding a CDV HA polypeptide and a polynucleotide encoding a GM-CSF polypeptide and a pharmaceutical or veterinarily acceptable carrier, excipient, vehicle, or adjuvant and one or more compositions comprising canine antigens is disclosed.

In yet another embodiment, a method of vaccinating an animal comprising a composition comprising a vector comprising a polynucleotide encoding a GM-CSF polypeptide and a pharmaceutical or veterinarily acceptable carrier, excipient, vehicle, or adjuvant and one or more compositions comprising canine antigens is disclosed.

In one embodiment of the invention, a prime-boost regime can be employed, which is comprised of at least one primary administration and at least one booster administration using at least one common polypeptide, antigen, epitope or immunogen. The administration may comprise one, two, or more vaccines or compositions comprising same or different antigens. Typically the immunological composition(s) or vaccine(s) used in primary administration is different in nature from those used as a booster. However, it is noted that the same composition(s) can be used as the primary administration and the booster administration. This administration protocol is called "prime-boost".

A prime-boost regimen comprises at least one prime-administration and at least one boost administration using at least one common polypeptide and/or variants or fragments thereof. The prime-administration may comprise one or more administrations. Similarly, the boost administration may comprise one or more administrations. The prime-administration may comprise one or more antigens and the boost administration may comprise one or more antigens.

In one aspect of the prime-boost protocol or regime of the invention, a prime-boost protocol may comprise the administration of a composition comprising a recombinant viral vector that contains and expresses a CDV HA polypeptide, antigen and/or variants or fragments thereof in vivo followed by the administration of a recombinant CDV HA polypeptide or antigen, or an inactivated viral composition or vaccine comprising the CDV HA polypeptide or antigen, or a DNA plasmid-based composition or vaccine expressing the CDV HA polypeptide or antigen. Likewise, a prime-boost protocol may comprise the administration of a composition comprising a recombinant CDV HA antigen, or an inactivated viral composition or vaccine comprising the CDV HA polypeptide or antigen, or a DNA plasmid-based composition or vaccine expressing the CDV HA polypeptide or antigen followed by the administration of a recombinant viral vector that contains and expresses a CDV HA polypeptide or antigen and/or variants or fragments thereof in vivo. It is further noted that both the primary and the secondary administrations may comprise the recombinant viral vector that contains and expresses a CDV HA polypeptide of the invention. Thus, the recombinant CDV viral vector of the invention may be administered in any order with a recombinant CDV antigen, an inactivated viral composition or vaccine comprising the CDV antigen, or a DNA plasmid-based composition or vaccine expressing the CDV antigen, or alternatively may be used alone as both the primary and secondary compositions.

The dose volume of compositions for target species that are mammals, e.g., the dose volume of dog compositions, based on viral vectors, e.g., non-poxvirus-viral-vector-based compositions, is generally between about 0.1 to about 2.0 ml, between about 0.1 to about 1.0 ml, and between about 0.5 ml to about 1.0 ml.

The efficacy of the vaccines may be tested about 2 to 4 weeks after the last immunization by challenging animals, such as dog, with a virulent strain of CDV. Both homologous and heterologous strains are used for challenge to test the efficacy of the vaccine. The animal may be challenged orally, by IV injection or by IC inoculation. For each different challenge strain and each route of administration used, the virus is at a sufficiently high titre to induce clinical symptoms in unvaccinated animals. The volume of challenge virus is about 0.5 to 2.0 ml. Animals may be observed for 21 to 42 days following challenge for clinical signs such as conjunctivitis, rhinitis, diarrhoea, vomiting, depression, dehydration, hyperthermia, pneumonia, ataxia, myoclonus, hyperesthesia, paralysis, paresis, seizures, eye symptoms (such as keratoconjunctivitis, chorioretinitis) and optic neuritis. During the challenge the animals may be blood sampled for complete blood counts and serology study (presence of CDV specific antibodies). In addition PCR may be carried out on samples of urine, tears, saliva, faeces and blood.

The compositions comprising the recombinant antigenic polypeptides of the invention used in the prime-boost protocols are contained in a pharmaceutically or veterinary acceptable vehicle, adjuvant, diluent or excipient. The protocols of the invention protect the animal from CDV and/or prevent disease progression in an infected animal.

The various administrations are preferably carried out 1 to 6 weeks apart. Preferred time interval is 3 to 5 weeks, and optimally 4 weeks According to one embodiment, an annual booster is also envisioned. The animals, for examples dogs, may be at least 8 weeks of age at the time of the first administration.

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

The present invention contemplates at least one administration to an animal of an efficient amount of the therapeutic composition made according to the invention. The animal may be male, female, pregnant female and newborn. This administration may be via various routes including, but not limited to, intramuscular (IM), intradermal (ID) or subcutaneous (SC) injection or via intranasal or oral administration. The therapeutic composition according to the invention can also be administered by a needleless apparatus (as, for example with a Pigjet, Dermojet, Biojector, Avijet (Merial, Ga., USA), Vetjet or Vitajet apparatus (Bioject, Oregon, USA)). Another approach to administering plasmid compositions is to use electroporation (see, e.g. Tollefsen et al., 2002; Tollefsen et al., 2003; Babiuk et al., 2002; PCT Application No. WO99/01158). In another embodiment, the therapeutic composition is delivered to the animal by gene gun or gold particle bombardment. In an advantageous embodiment, the animal is a dog, ferret or seal.

In one embodiment, the invention provides for the administration of a therapeutically effective amount of a formulation for the delivery and expression of a CDV antigen or epitope in a target cell. Determination of the therapeutically effective amount is routine experimentation for one of ordinary skill in the art. In one embodiment, the formulation comprises an expression vector comprising a polynucleotide that expresses a CDV antigen or epitope and a pharmaceutically or veterinarily acceptable carrier, vehicle, adjuvant, or excipient. In another embodiment, the pharmaceutically or veterinarily acceptable carrier, vehicle, adjuvant, or excipient facilitates transfection or infection and/or improves preservation of the vector or protein in a host.

In one embodiment, the invention provides for the administration of a therapeutically effective amount of a composition for the delivery and expression of a CDV HA polypeptide or antigen or epitope in a target cell. Determination of the therapeutically effective amount is routine experimentation for one of ordinary skill in the art. In one embodiment, the composition comprises an expression vector comprising a polynucleotide that expresses a CDV HA polypeptide or antigen or epitope and a pharmaceutically or veterinarily acceptable carrier, adjuvant, vehicle or excipient. In another embodiment, the pharmaceutically or veterinarily acceptable carrier, vehicle, adjuvant, or excipient facilitates transfection or infection and/or improves preservation of the vector or protein.

The pharmaceutically or veterinarily acceptable carriers or vehicles or excipients or adjuvants are well known to the one skilled in the art. For example, a pharmaceutically or veterinarily acceptable carrier or vehicle or excipient or adjuvant can be a 0.9% NaCl (e.g., saline) solution or a phosphate buffer. Other pharmaceutically or veterinarily acceptable carrier or vehicle or excipient or adjuvant that can be used for methods of this invention include, but are not limited to, poly-(L-glutamate) or polyvinylpyrrolidone. The pharmaceutically or veterinarily acceptable carrier or vehicle or excipient or adjuvant may be any compound or combination of compounds facilitating the administration of the vector (or protein expressed from an inventive vector in vitro); advantageously, the carrier, vehicle or excipient or adjuvant may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are those having the following formula:

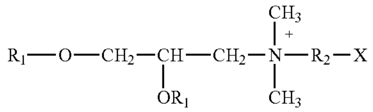

in which R1 is a saturated or unsaturated straight-chain aliphatic radical having 12 to 18 carbon atoms, R2 is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr, 1994), to form DMRIE-DOPE.

When DOPE is present, the DMRIE:DOPE molar ratio is advantageously about 95:about 5 to about 5:about 95, more advantageously about 1:about 1, e.g., 1:1.

In another embodiment, pharmaceutically or veterinarily acceptable carrier, excipient, vehicle or adjuvant may be a water-in-oil emulsion. Examples of suitable water-in-oil emulsions include oil-based water-in-oil vaccinal emulsions which are stable and fluid at 4° C. containing: from 6 to 50 v/v % of an antigen-containing aqueous phase, preferably from 12 to 25 v/v %, from 50 to 94 v/v % of an oil phase containing in total or in part a non-metabolizable oil (e.g., mineral oil such as paraffin oil) and/or metabolizable oil (e.g., vegetable oil, or fatty acid, polyol or alcohol esters), from 0.2 to 20 p/v % of surfactants, preferably from 3 to 8 p/v %, the latter being in total or in part, or in a mixture either polyglycerol esters, said polyglycerol esters being preferably polyglycerol (poly)ricinoleates, or polyoxyethylene ricin oils or else hydrogenated polyoxyethylene ricin oils. Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084. In some embodiments, the antigen-containing aqueous phase comprises a saline solution comprising one or more buffering agents. An example of a suitable buffering solution is phosphate buffered saline. In one embodiment, the water-in-oil emulsion may be a water/oil/water (W/O/W) triple emulsion (U.S. Pat. No. 6,358,500). Examples of other suitable emulsions are described in U.S. Pat. No. 7,371,395.

The immunological compositions and vaccines according to the invention may comprise or consist essentially of one or more pharmaceutically or veterinarily acceptable carriers, excipients, vehicles or adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether.

With regard to structure, the acrylic or methacrylic acid polymers and EMA are preferably formed by basic units having the following formula:

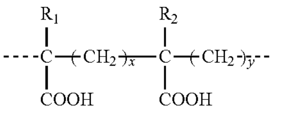

in which:

R1 and R2, which can be the same or different, represent H or CH3 x=0 or 1, preferably x=1 y=1 or 2, with x+y=2.

For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between about 0.01 to about 1.5% w/v, about 0.05 to about 1% w/v, and about 0.1 to about 0.4% w/v.

The cytokine or cytokines (5) can be in protein form in the immunological or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector thereof.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFNα), interferon β (IFNβ), interferon γ, (IFNγ), interleukin-1α(IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a canine cytokine for preparations to be administered to canine).

The invention will now be further described by way of the following non-limiting examples.

EXAMPLES

Without further elaboration, it is believed that one skilled in the art can, using the preceding descriptions, practice the present invention to its fullest extent. The following detailed examples are to be construed as merely illustrative, and not limitations of the preceding disclosure in any way whatsoever. Those skilled in the art will promptly recognize appropriate variations from the procedures both as to reactants and as to reaction conditions and techniques.

Construction of DNA inserts, plasmids and recombinant viral or plant vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989).

Example 1 Construction of Plasmid Containing CDV HA—pC5 H6 CDV HA, pCXL1557.1

The plasmid containing codon-optimized CDV HA gene (SEQ ID NO:1) (from Danish CDV strain) was digested with EcoRV and XhoI. The 1849 bp fragment containing 3' sequence of vaccinia H6 promoter and full-length codon-optimized CDV HA gene was gel purified. Plasmid pCXL148.2 (pC5 donor plasmid, Merial proprietary material) was digested with EcoRV and Xho I to generate a 49851 bp vector containing 5' sequence of H6 promoter. The 1849 bp insert was ligated to the 49851 bp vector to generate the pC5 H6 CDV HA (pCXL1557.1). The construct was sequenced to confirm the correct sequence. FIG. 3 displays plasmid pCXL1557.1 map.

Example 2 Construction of Plasmid Containing Canine GM-CSF-pC3 H6p Canine GM-CSF, pJSY2218.1

The plasmid containing the codon-optimized canine GM-CSF gene was digested with NruI/XhoI. The resulting canine GM-CSF DNA fragment was isolated and ligated to NruI/XhoI digested pJY19131.1 (Merial proprietary material) to create a C3 donor plasmid pJSY2218.1, which contains the expression cassette H6p (vaccinia H6 promoter)-canine GM-CSF in an opposite orientation against C3 arms. Plasmid pJSY2218.1 was sequenced and confirmed to have the correct sequence. FIG. 3 displays plasmid pJSY2218.1 map.

Example 3 Generation and Characterization of ALVAC Recombinant Containing CDV Synthetic HA Gene in C5 Loci of ALVAC (vCP2263)

A. Generation of vCP2263

The donor plasmid pCXL1557.1 contains codon-optimized canine CDV HA gene (SEQ ID NO:1). Primary chicken embryo fibroblast (1° CEF) cells were used for in vitro recombination. 1° CEF cells were grown in 10% FBS (JRH: γ-irradiated #12107-500M), DMEM (BRL/Gibco#11960-051 or 11960-044) supplemented with 4 mM Glutamine (BRL/Gibco#25030-081) and 1 mM Sodium Pyruvate (BRL/Gibco#11360-070) in the presence of 1× antibiotics/antimycotics (P/S/A/A, BRL/Gibco#15240-062). Plaque hybridization with horseradish peroxidase (HRP)-labeled CDV synthetic HA specific probe was used for recombinant selection.

The IVR (in vitro recombinant) was performed by transfection of 1° CEF cells with 12 μg of Not I-linearized donor plasmid pCXL1557.1 using FuGENE-6® reagent (Roche). The transfected cells were subsequently infected with ALVAC as rescue virus at MOI (multiplicity of infection) of 10 (ALVAC Stock, $6.3\times10^9$ pfu/ml). After 24 hours, the transfected-infected cells were harvested, sonicated and used for recombinant virus screening. Recombinant plaques were screened based on the plaque lift hybridization method using a 1232 bp synthetic HA specific probe labeled with horse radish peroxidase (HRP) according to the manufacturer's protocol (Amersham Cat# RPN3001,). After four sequential rounds of plaque purification, the recombinants designated as vCP2263.1.2.1.1 and vCP2263.6.1.1.1 were generated and confirmed by hybridization as 100% positive for the HA insert and 100% negative for the empty C5 site. Single plaques were selected from the 4th round of plaque purification, and expanded to obtain P1 (1×T25 flask per sister), P2 (1×T75 flask per sister) and P3 (4× roller bottles for vCP2263.1.2.1.1.) stocks to amplify vCP2263. The infected cell culture fluid from the roller bottles was harvested and concentrated to produce the virus stock.

B. Genomic Analysis

Genomic DNA from vCP2263.1.2.1.1 and vCP2263.6.1.1.1 was extracted, digested with BamHI, HindIII or Pst I and run on 0.8% agarose gel. The results revealed the correct insertion of CDV synthetic HA sequence.

Southern blot: The gel with BamHI, HindIII or PstI digested genomic DNA was transferred to nylon membrane and Southern blot analysis was performed by probing with a synthetic CDV HA specific probe. Single or double bands from all three digests were observed at the expected sizes: 1984 bp BamHI, 12294 bp HindIII and 6465 and 12119 bp PstI (see FIG. 4), indicating the correct insertion of CDV synthetic HA into the C5 loci.

Primers for amplifying the synthetic CDV HA probe:

```
13220CXL:
                                    (SEQ ID NO: 10)
5' AGGTGTCCACCTCCAACATGGAGT 3'

13225CXL:
                                    (SEQ ID NO: 11)
5' GAACTGGTCGCCCCTGGAGGCCTT 3'
```

C. Expression Analysis

Figure 5:
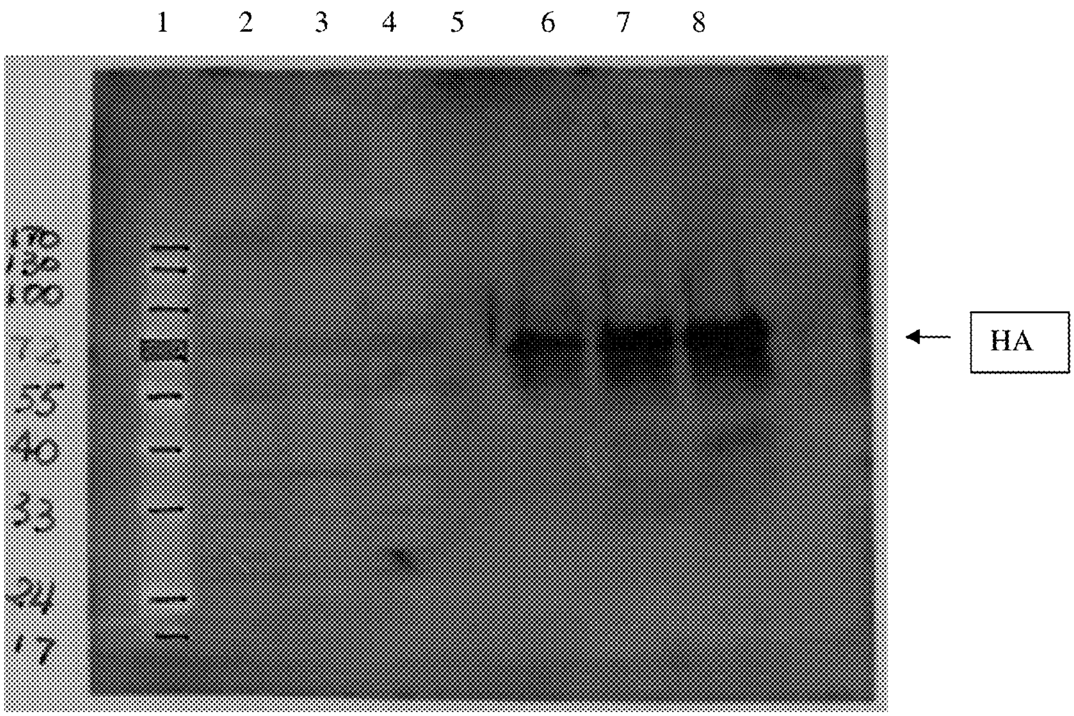
FIG. 5 shows the Western blot of vCP2263.

Western blot: 1° CEF cells were infected with the P2 stock at a MOI of 10 and incubated at 37° C. for 25 hrs. The cells and culture supernatant were then harvested. Sample proteins were separated on a 10% SDS-PAGE gel, transferred to Immobilon nylon membrane, and probed with rabbit anti-CDV polyclonal antibody (pool sera from rabbit A151, and 152 at 1 in 100 dilution). Peroxidase-conjugated Donkey anti-rabbit antiserum was used as a secondary antibody and the bands were visualized using luminol reagents. vCP2263.1211 showed a very weak single band at 73 kDa in the cell supernatant fraction, but no CDV specific band was detected in the cell pellet fraction (see FIG. 5).

Figure 6:
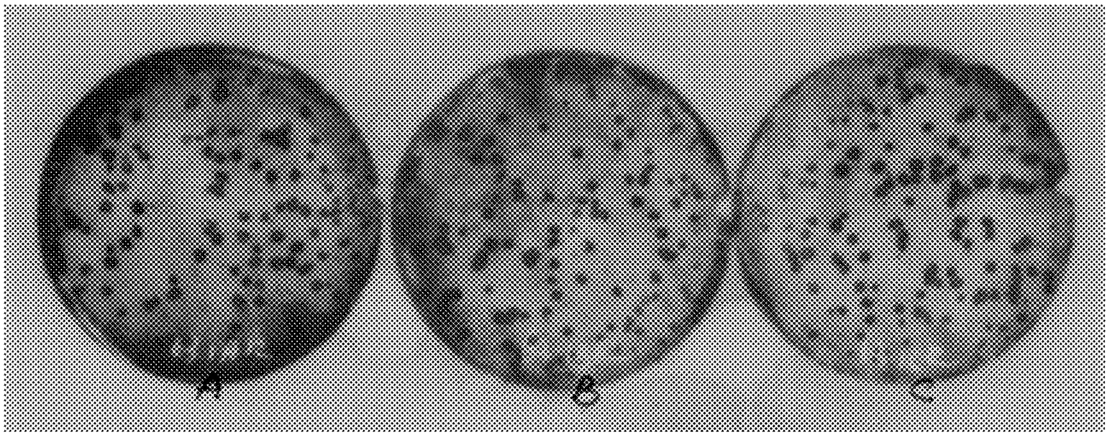
FIG. 6 shows the immunoplaque assay of vCP2263.

Immunoplaque: The homogeneity of the population was 100% for vCP2263.1.2.1.1, as evidenced by an immunoplaque assay, using the Rabbit anti-CDV antibody (see FIG. 6).

D. Sequence Analysis

A more detailed analysis of the P3 stock genomic DNA was performed by PCR amplification and sequence analysis of the flanking arms of the C5 locus and the CDV synthetic HA insert. Primers 7931DC and 7932DC, located beyond the arms of the C5 locus in the ALVAC genome, were used to amplify the entire C5L-CDV synthetic HA-C5R fragment. The results showed that the sequences of the CDV synthetic HA and C5L and C5R of ALVAC are correct.

Primers for PCR Amplification:

```
7931DC:
                                    (SEQ ID NO: 12)
5' GAATCTGTTAGTTAGTTACTTGGAT 3'
```

-continued

```
7932DC:
                                    (SEQ ID NO: 13)
5' TGATTATAGCTATTATCACAGACTC 3'
```

The DNA sequence flanked by primers 7931DC and 7932DC containing C5 arms, H6 promoter, and CDV synthetic HA is designated SEQ ID NO:14.

Example 4 Generation and Characterization of ALVAC Recombinant Containing H6p Synthetic Codon Optimized Canine GM-CSF Gene Inserted at C3 Locus of ALVAC—vCP2391

A. Generation of vCP2391

The donor plasmid pJSY2218.1 contains codon-optimized canine GM-CSF gene (SEQ ID NO:3). Primary chicken embryo fibroblast cells (1° CEF) were used for in vitro recombination. Plaque hybridization with horseradish peroxidase (HRP)-labeled Canine GM-CSF specific probe was used for recombinant selection.

The IVR was performed by transfection of 1° CEF cells with 10 μg of Not I-linearized donor plasmid pJSY2218.1 using FuGENE-6® reagent (Roche). The transfected cells were subsequently infected with ALVAC as rescue virus at MOI of 10. After 24 hours, the transfected-infected cells were harvested, sonicated and used for recombinant virus screening. Recombinant plaques were screened based on the plaque lift hybridization method using a 382 base canine GM-CSF specific probe labeled with horse radish peroxidase (HRP) according to the manufacturer's protocol (Amersham Cat# RPN3001). After two sequential rounds of plaque purification, the recombinant designated as vCP2391.4.4 was generated and confirmed by hybridization as 100% positive for the canine GM-CSF insert and 100% negative for the C3 ORF. Single plaque was selected from the 2nd round of plaque purification, and expanded to obtain P1 (1×T25 flask), P2 (1×T75 flask) and P3 (6× roller bottles).

B. Genomic Analysis—Southern Blot

Genomic DNA from vCP2391 was extracted, digested with BamHI, HindIII or Pst I and run on 0.8% agarose gel. The gel with BamHI, HindIII or PstI digested genomic DNA was transferred to a nylon membrane and Southern blot analysis was performed by probing with the 382 base caGM-CSF probe. Multiple bands were observed at the expected sizes, indicating the correct insertion of the caGM-CSF gene into the C3 locus.

| Restriction enzyme | Fragment (bp) | | |
|---|---|---|---|
| Bam HI | 7598 | 16674 | |
| Hind III | 16344 | | |
| Pst I | 219 | 1696 | 11293 |

Primers for amplifying the Canine GM-CSF probe

```
18071BK:
                                    (SEQ ID NO: 15)
5' GATGTTGAACAGGAAGTCCTTCAGGT 3'

18073BK:
                                    (SEQ ID NO: 16)
5' GTTCCTGGGCACCGTGGTGTGCAGCA 3'
```

C. Expression Analysis

Figure 7:
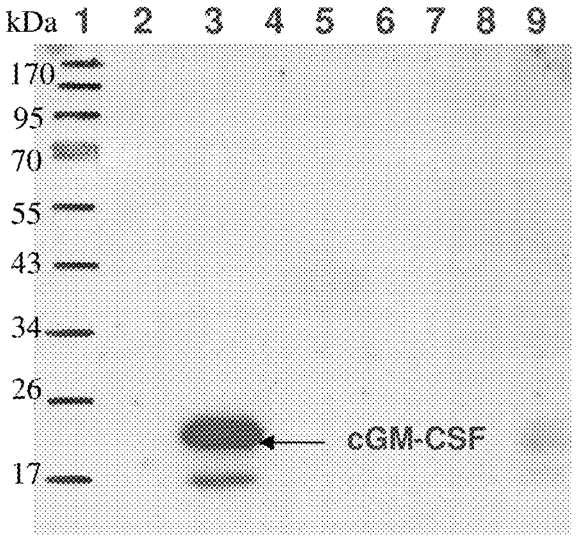
FIG. 7 shows the western blot of vCP2391.
Figure 9:
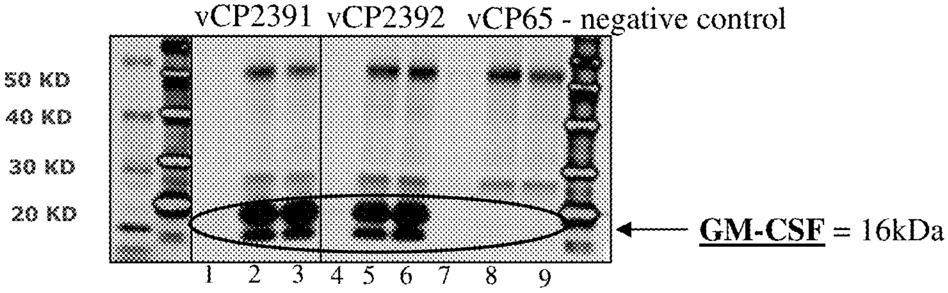
FIG. 9 shows the western blot of vCP2391 and vCP2392 for GM-CSF.

Western blot: Primary CEF cells were infected with the P3 stock of vCP2391.4.4 at MOI of 10 and incubated at 37° C.

for 24 hrs. All the culture supernatant and cells were then harvested. Cell pellet was lysed with Reporter Gene Assay Lysis Buffer manufactured by Roche (Cat. 1 897 675). Both supernatant and cell lysate were prepared with the NuPage® System with addition of antioxidant. Proteins were separated on a NuPage® 10% Bis-Tris Pre-cast gel, and then transferred to a PVDF membrane. Purified goat anti-canine GM-CSF IgG (R&D Systems, Cat AF1546) was used as primary antibody. Western blot detected a major protein of ~20 kDa and a minor protein of ~17 kDa secreted from the supernatant of vCP2391.4.4 (see FIGS. 7 and 9). FIG. 9 showed good expression of GM-CSF in crude and supernatant.

D. Sequence Analysis

A more detailed analysis of the P3 stock genomic DNA of vCP2391.4.4 was performed by PCR amplification and sequence analysis of the flanking arms of the C3 locus and the canine GM-CSF insert. Primers 8103JY and 8104JY, located beyond the arms of the C3 locus in the ALVAC genome were used to amplify the entire C3L-caGM-CSF-C3R fragment. The results showed that the sequences of the canine GM-CSF insert and C3L and C3R of ALVAC are correct (SEQ ID NO: 19).

Primers for PCR amplification of C3L-Canine GM-CSF-C3R cassette:

```
8103JY:
                                        (SEQ ID NO: 17)
5' GAGGCATCCAACATATAAAGAAGACTAAAG 3'

8104JY:
                                        (SEQ ID NO: 18)
5' TAGTTAAATACTCATAACTCATATCTG 3'
```

Example 5 Generation and Characterization of ALVAC Recombinant Containing H6p Synthetic Codon Optimized Canine GM-CSF Gene Inserted at C3 Locus of vCP2263vCP2392

ALVAC C5 H6p CDV (vCP2263.1.2.1.1) was used as a parental virus. pJSY2218.1 containing the codon-optimized canine GM-CSF gene was used as a donor plasmid. Primary chicken embryo fibroblast cells (1° CEF) were used for in vitro recombination. Plaque hybridization with horseradish peroxidase (HRP)-labeled Canine GM-CSF specific probe was used for recombinant selection.

The IVR was performed by transfection of 1° CEF cells with 10 ug of Not I-linearized donor plasmid pJSY2218.1 using FuGENE-6® reagent (Roche). The transfected cells were subsequently infected with vCP2263.1.2.1.1 as rescue virus at MOI of 10. After 24 hours, the transfected-infected cells were harvested, sonicated and used for recombinant virus screening. Recombinant plaques were screened based on the plaque lift hybridization method using a 382 base canine GM-CSF specific probe (example 4) labeled with horse radish peroxidase (HRP) according to the manufacturer's protocol (Amersham Cat# RPN3001). After four sequential rounds of plaque purification, the recombinant designated as vCP2392.5.3.1.1 was generated and confirmed by hybridization as 100% positive for the canine GM-CSF insert and 100% negative for the C3 ORF. Single plaque was selected from the 4th round of plaque purification, and expanded to obtain P1 (1×T25 flask), P2 (1×T75 flask) and P3 (6× roller bottles).

A. Genomic Analysis—Southern Blot

Genomic DNA from vCP2392 was extracted, digested with BamHI, HindIII or Pst I and run on 0.8% agarose gel. The gel with BamHI, HindIII or PstI digested genomic DNA was transferred to a nylon membrane and Southern blot analysis was performed by probing with the 382 base canine GM-CSF probe (example 4). Multiple bands were observed at the expected sizes, indicating the correct insertion of the canine GM-CSF gene into the C3 locus.

| Restriction enzyme | Fragment (bp) | | |
|---|---|---|---|
| Bam HI | 7598 | 16674 | |
| Hind III | 16344 | | |
| Pst I | 219 | 1696 | 11293 |

B. Expression Analysis

Figure 8:
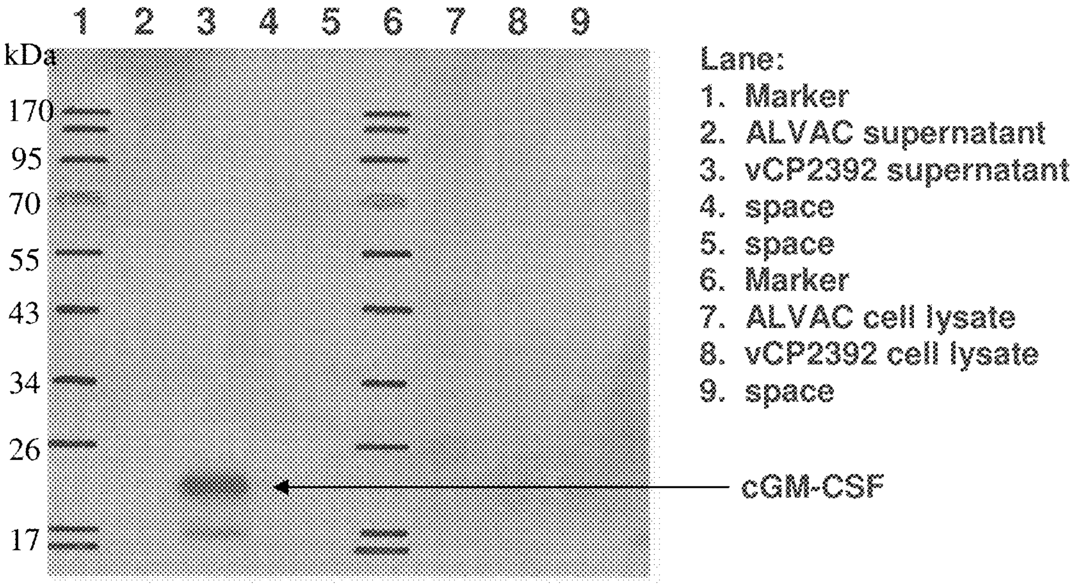
FIG. 8 shows the western blot of vCP2392.
Figure 10:
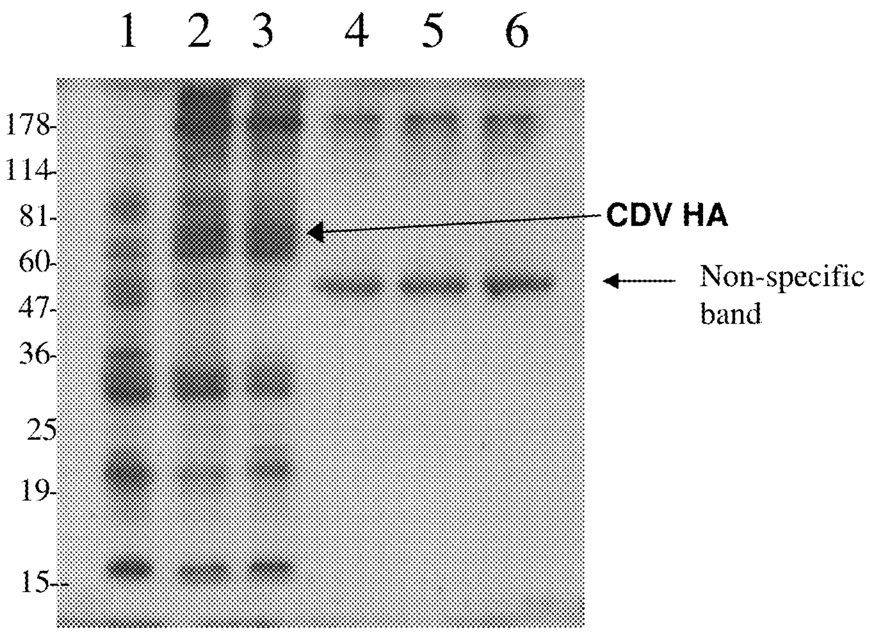
FIG. 10 shows the western blot of vCP2392 for CDV HA protein.

Western blot: Primary CEF cells were infected with the P3 stock of vCP2392.5.3.1.1 at MOI of 10 and incubated at 37° C. for 24 hrs. All the culture supernatant and cells were then harvested. Cell pellet was lysed with Reporter Gene Assay Lysis Buffer manufactured by Roche (Cat. 1 897 675). Both supernatant and cell lysate were prepared with the NuPage® System with addition of antioxidant. Proteins were separated on a NuPage® 10% Bis-Tris Pre-cast gel, and then transferred to a PVDF membrane. Purified goat anti-canine GM-CSF IgG (R&D Systems, Cat AF1546) was used as primary antibody. Western blot detected a major protein of ~20 kDa and a minor protein of ~17 kDa secreted from the supernatant of vCP2392.5.3.1.1. (see FIGS. 8 and 9). The result of CDV HA expression is shown in FIG. 10. The result showed good expression of CDV HA protein with vCP2392.

C. Sequence Analysis

A more detailed analysis of the P3 stock genomic DNA of vCP2392.5.3.1.1 was performed by PCR amplification and sequence analysis of the flanking arms of the C3 locus and the canine GM-CSF insert. Primers 8103JY and 8104JY (see example 4), located beyond the arms of the C3 locus in the ALVAC genome, were used to amplify the entire C3L-caGM-CSF-C3R fragment. The results showed that the sequences of the canine GM-CSF insert and C3L and C3R of ALVAC are correct.

Example 6 Comparison of the Efficacy of the Recombinant Canarypox-Canine CDV HA and Canine GM-CSF (vCP2392) and the Recombinant Canarypox-Canine CDV HA (vCP2263) by Challenge in Dogs Eighteen CDV specific pathogen free dogs were used. The 4 month old male and female dogs were grouped into three groups, and were vaccinated and sampled as shown in Table 1 below.

TABLE 1

| Group (n = 6) | Antigen (titre in $log_{10}$ $TCID_{50}$/ml) | Vaccination | Post vaccination clinical examinations | Monitoring of Serological and CMI responses |
|---|---|---|---|---|
| A | vCP2392 CDV + GM-CSF (6.21) | D0 & D28, 1 ml by the SQ route | General and local clinical signs | Serology: CDV SN CDV SN on Vero SLAM cells GM-CSF ELISA |
| B | vCP2263 CDV (6.38) | — | | |
| C | Not Vaccinated | | | |

TABLE 1-continued

| Group (n = 6) | Antigen (titre in $log_{10}$ $TCID_{50}$/ml) | Vaccination | Post vaccination clinical examinations | Monitoring of Serological and CMI responses |
|---|---|---|---|---|
| | | | | CMI: T-cell responses |

SN: seroneutralization test
SLAM: signaling lymphocyte-activation molecule
CMI: cell mediated immunity Clinical examinations were performed on days: (V1) 0, 0+4/5 h, 1, 2, (V2) 28, 28+4/5 h, 29, 30, or until all symptoms had disappeared. Clinical monitoring included monitoring general condition of the dogs, such as rectal temperature, pain on palpation of injection site, local swelling, local heat, pruritus and local hair loss.

Figure 11:
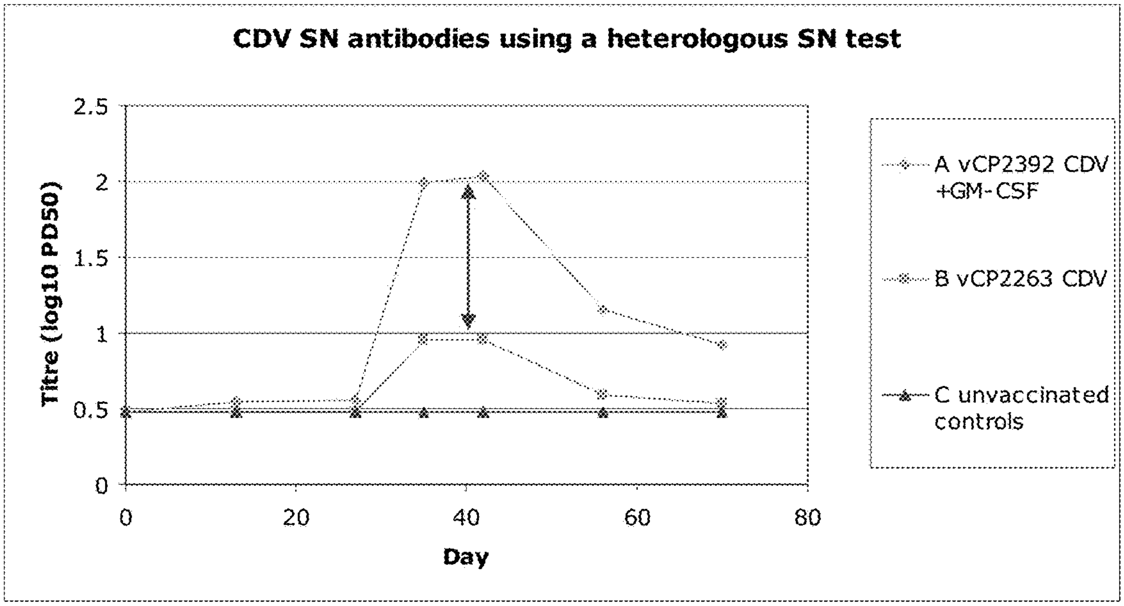
FIG. 11 provides the serology results of vCP2392 and vCP2263 using a heterologous SN test.
Figure 12:
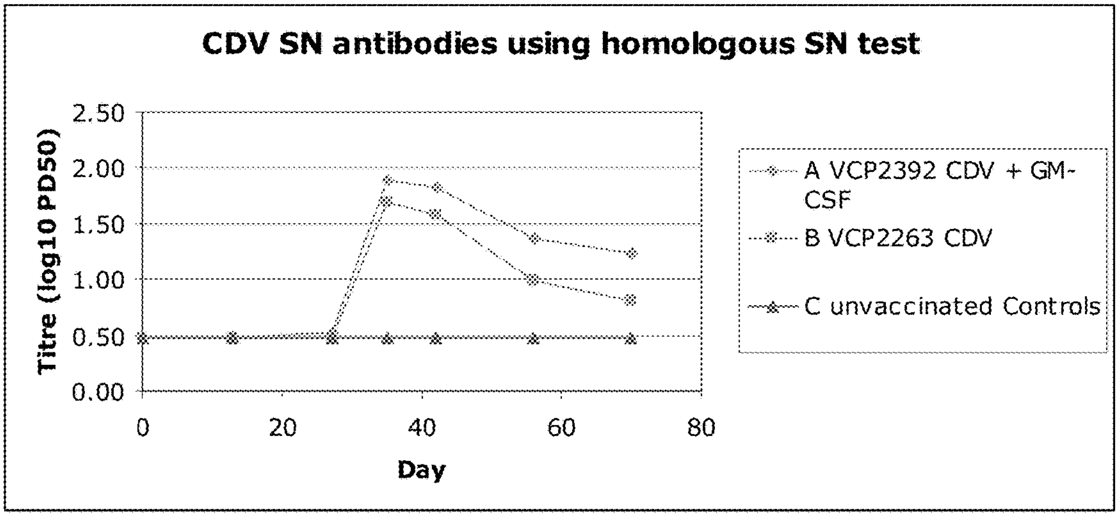
FIG. 12 provides the serology results of vCP2392 and vCP2263 using a homologous SN test.

Sampling in plain tubes for serology was performed on days: 0, 13, 27, 35, 42, 56, and 70. Two types of SN were performed. CDV strain (BA5) which is heterologous to the CDV HA insert in vCP2392 and vCP2263 was used. The result is shown in FIG. 11. The result showed that the titre in group A is higher than the titre in group B (1 log 10), p=0.009, p=0.019 and p=0.03 at D35, D42 and D70 respectively. In group B on D42, there were 3 dogs with titre <0.8 log 10PD50. The second type of SN using vero SLAM cells and CDV strain 5804-GFP which is homologous to the CDV HA insert in vCP2392 and vCP2263 was performed. The result is shown in FIG. 12. The result showed that group A titres are higher than group B titres. The result also showed that there were two dogs in group B that have attire of 0.48 on D70 while in group A all dogs had serological titres of 0.72 or more.

Sampling in heparinated tubes for monitoring of CMI was performed on days: 13, 42, and 70. The production of IFNγ was monitored using ELIspot assay upon PBMCs (peripheral blood mononuclear cells) re-stimulation with PBMCs nucleofected. The frequency of antigen specific IFNγ producing cells was calculated. The data is shown in FIG. 16.

In summary: vCP2392 (CDV HA+canine GM-CSF) induces significantly higher serology responses compared to vCP2263 (CDV HA).

Example 7 Effect of vCP2392 on the Immunogenicity of Other Vaccine Antigens

This study was designed to investigate whether vCP2392 (co-expressing CDV HA and canine GM-CSF) has a positive impact on the immunogenicity of other vaccine antigens.

A modified live canine parvovirus vaccine was used at a dose (2.6 $log_{10}$ TCID50) which is well below the normal commercial dose. Twelve SPF (specific pathogen free) male and female beagle puppies (2-3 month old) were randomly assigned into two groups and vaccinated as shown in Table 2 below.

TABLE 2

| | *Vaccination D0 & D28 | | | | | |
|---|---|---|---|---|---|---|
| | CDV antigen | | CPV2 antigen | | CDV & | |
| Group N = 6 | vCP | Dose ($log_{10}$ $TCID_{50}$/ml) | MLV** | Dose ($log_{10}$ $TCID_{50}$/ml) | CPV2 Serology | Clinical monitoring |
| A | 2392 (CDV HA + GM-CSF) | 6.75 | CPV2 | 2.6 | D0, D7, D14, D28, D35, D42, D56 | D0, D0 + 4-5 h, D1 & D2 D28, D28 + 4-5 h, D29 & D30 |
| B | 2263 (CDV HA) | 6.91 | CPV2 | 2.6 | | |

*2 ml (vCP + MLV-CPV2 in PBS) by the SC route on the right shoulder (D0) then on the left shoulder (D28)
**modified live virus - canine parvovirus type 2 (MLV-CPV2)

Clinical monitoring included general condition, rectal temperature, pain on palpation of injection site, local swelling, local heat and pruritus. The vaccines received were well tolerated by dogs in both groups A and B. vCP2392 (CDV HA+GM-CSF) and vCP2263 (CDV HA) in combination with MLV-CPV2 was considered safe based on the clinical study result.

Sera were titrated for antibodies against CPV2 and CDV (using homologous and heterologous CDV in seroneutralization test).

FIG. 17 shows the CVP2 ELISA result. None of the animals in groups A and B had antibodies against CPV2 at the start of the study. In group B, only one dog mounted an antibody response following vaccination. This response was detected from D28 onwards. In group A, 4 out of 6 dogs showed high antibody responses and responses were detected as early as D7 in some of the dogs. None of the dogs showed a booster response after the second injection on D28. Statistical analyses on the incidence of responders showed that the groups were significantly different (p=0.046). The result indicated that the GM-CSF insert included in vCP2392 had a positive effect on CPV2 serology.

Figure 18:
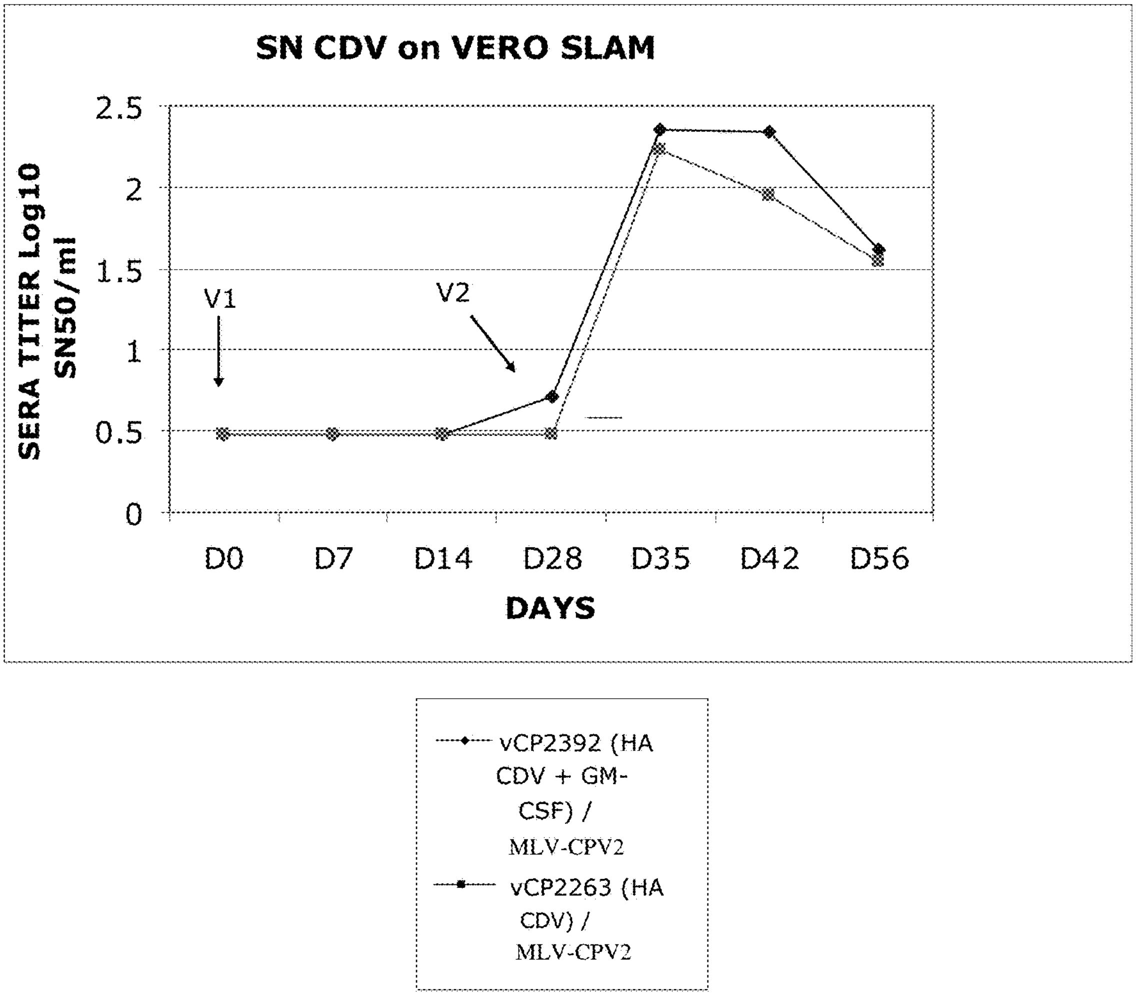
FIG. 18 depicts the homologous SN test result of CDV SN antibodies.

FIG. 18 shows the result of CDV homologous SN (seroneutralization) test. Before vaccination, none of the animals had antibodies against CDV. Group A and B titres were similar on D35 and D56. However 5/6 dogs from group A had antibodies on D28 while none of the dogs in group B had antibodies on D28. On D42 serological titres were significantly higher in group A (Student t-test, p=0.01).

Figure 19:
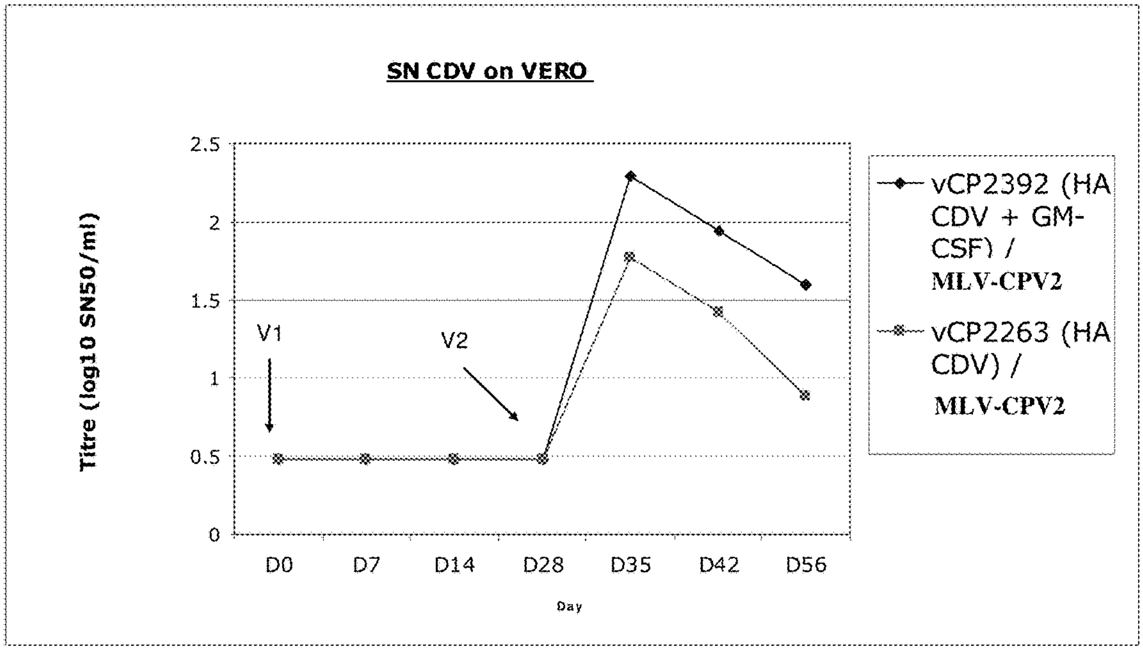
FIG. 19 depicts the heterologous SN test result of CDV SN antibodies.

FIG. 19 shows the result of CDV heterologous SN test. Before vaccination, none of the animals had antibodies against CDV. Antibody titres in group A tended to be higher than group B titres on days 35, 42 and 56. On D56, antibody titres in group A were significantly higher than in group B (Wilcoxon, p=0.016).

The study results showed that a dose of 2.6 $\log_{10}$ TCID50 of MLV-CPV2 per dog was under the minimum dose that can confer seroconversion, as shown in group B's result. Interestingly and surprisingly, the inclusion of GM-CSF in canarypox vector (vCP2392) induced different antibody response, as shown in group A's result. The results demonstrated that the presence of caGM-CSF in canarypox vector can have an effect on the immunogenicity of another vaccine component injected into the same site.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

All documents cited or referenced in the application cited documents, and all documents cited or referenced herein (herein cited documents), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What is claimed is:

1. A composition comprising a vCP2392 canarypox vector and a veterinary acceptable vehicle, wherein the vCP2392 canarypox vector comprises SEQ ID NO: 14.

2. The composition of claim 1, further comprising an additional antigen.

3. The composition of claim 2, wherein the additional antigen is associated with a pathogen selected from the group consisting of rabies, canine parvovirus, canine coronavirus, canine influenza, infectious canine hepatitis, canine herpesvirus, pseudorabies, canine minute virus, *Leptospira*, and *Neospora caninum.*

4. A method of inducing an immune response in an animal comprising at least one administration of an effective amount of the composition of claim 1.

5. The method of claim 4, wherein the method comprises a prime-boost administration protocol.

6. The composition of claim 1, wherein the composition further comprises a veterinary acceptable adjuvant.

* * * * *